United States Patent
Miller et al.

(10) Patent No.: US 7,579,589 B2
(45) Date of Patent: Aug. 25, 2009

(54) ULTRA COMPACT ION MOBILITY BASED ANALYZER APPARATUS, METHOD, AND SYSTEM

(75) Inventors: Raanan A. Miller, Chestnut Hill, MA (US); Stephen Coy, Wayland, MA (US); Stephen D. Kendig, Carisle, MA (US); C. James Morris, Norfolk, MA (US); John A. Wright, Billerica, MA (US); Erkinjon G. Nazarov, Lexington, MA (US)

(73) Assignee: Sionex Corporation, Bedford, MA (US)

( * ) Notice: Subject to any disclaimer, the term of this patent is extended or adjusted under 35 U.S.C. 154(b) by 191 days.

(21) Appl. No.: 11/494,053

(22) Filed: Jul. 26, 2006

(65) Prior Publication Data
US 2009/0189064 A1 Jul. 30, 2009

Related U.S. Application Data

(60) Provisional application No. 60/750,546, filed on Dec. 15, 2005, provisional application No. 60/702,376, filed on Jul. 26, 2005, provisional application No. 60/710,634, filed on Aug. 23, 2005, provisional application No. 60/723,641, filed on Oct. 5, 2005, provisional application No. 60/753,300, filed on Dec. 21, 2005.

(51) Int. Cl.
*B01D 59/44* (2006.01)
*H01J 49/00* (2006.01)
*H01J 49/40* (2006.01)
*H01J 49/28* (2006.01)

(52) U.S. Cl. .................. 250/292; 250/281; 250/282; 250/290; 250/293; 250/288

(58) Field of Classification Search .......... 250/281, 250/282, 299, 293, 286, 287, 288
See application file for complete search history.

(56) References Cited

U.S. PATENT DOCUMENTS

| | | | |
|---|---|---|---|
| 2,615,135 | A | 10/1952 | Glenn |
| 2,818,507 | A | 12/1957 | Britten |
| 2,919,348 | A | 12/1959 | Bierman |
| 3,511,986 | A | 5/1970 | Llewellyn |
| 3,619,605 | A | 11/1971 | Cook et al. |
| 3,621,240 | A | 11/1971 | Cohen et al. |
| 3,648,046 | A | 3/1972 | Denison et al. |
| 3,931,589 | A | 1/1976 | Aisenberg et al. |
| 4,019,989 | A | 4/1977 | Hazewindus et al. |
| 4,025,818 | A | 5/1977 | Giguere et al. |

(Continued)

FOREIGN PATENT DOCUMENTS

DE 41342112 4/1993

(Continued)

OTHER PUBLICATIONS

Zampolli et al. "Selectivity enhancement of metal oxide gas sensors using a micromachined gas chromatographic column" Sensors and Actuators B, Elsevier Sequoia S.A., Lausanne, Ch, vol. 105, No. 2, Mar. 28, 2005, p. 400-406.

(Continued)

*Primary Examiner*—David A Vanore
*Assistant Examiner*—Brooke Purinton
(74) *Attorney, Agent, or Firm*—Ropes & Gray LLP

(57) ABSTRACT

An ultra compact ion mobility based analyzer in a multilayered chip assembly employing various features such as a ion flow generator to propel ions through an ion mobility based filter and, thereby, reduce analyzer size, cost, and power requirements.

26 Claims, 41 Drawing Sheets

U.S. PATENT DOCUMENTS

| | | | |
|---|---|---|---|
| 4,136,280 A | 1/1979 | Hunt et al. |
| 4,163,151 A | 7/1979 | Bayless et al. |
| 4,167,668 A | 9/1979 | Mourier |
| 4,201,921 A | 5/1980 | McCorkle |
| 4,315,153 A | 2/1982 | Vahrenkamp |
| 4,517,462 A | 5/1985 | Boyer et al. |
| 4,761,545 A | 8/1988 | Marshall et al. |
| 4,885,500 A | 12/1989 | Hansen et al. |
| 4,931,640 A | 6/1990 | Marshall et al. |
| 5,019,706 A | 5/1991 | Allemann et al. |
| 5,047,723 A | 9/1991 | Puumalainen |
| 5,144,127 A | 9/1992 | Williams et al. |
| 5,218,203 A | 6/1993 | Eisele et al. |
| 5,298,745 A | 3/1994 | Kernan et al. |
| 5,373,157 A | 12/1994 | Hiroki et al. |
| 5,420,424 A | 5/1995 | Carnahan et al. |
| 5,455,417 A | 10/1995 | Sacristan |
| 5,479,815 A | 1/1996 | White et al. |
| 5,492,867 A | 2/1996 | Kotvas et al. |
| 5,508,204 A | 4/1996 | Norman |
| 5,536,939 A | 7/1996 | Freidhoff et al. |
| 5,541,408 A | 7/1996 | Sittler |
| 5,644,131 A | 7/1997 | Hansen |
| 5,654,544 A | 8/1997 | Dresch |
| 5,723,861 A | 3/1998 | Carnahan et al. |
| 5,736,739 A | 4/1998 | Uber et al. |
| 5,763,876 A | 6/1998 | Pertinarides et al. |
| 5,789,745 A | 8/1998 | Martin et al. |
| 5,801,379 A | 9/1998 | Kouznetsov |
| 5,811,059 A | 9/1998 | Genovese et al. |
| 5,834,771 A | 11/1998 | Yoon et al. |
| 5,838,003 A | 11/1998 | Bertsch et al. |
| 5,852,302 A | 12/1998 | Hiraishi et al. |
| 5,869,344 A | 2/1999 | Linforth et al. |
| 5,965,882 A | 10/1999 | Megerle et al. |
| 5,998,788 A | 12/1999 | Breit |
| 6,049,052 A | 4/2000 | Chutjian et al. |
| 6,051,832 A | 4/2000 | Bradshaw |
| 6,055,151 A | 4/2000 | Tormey et al. |
| 6,066,848 A | 5/2000 | Kassel et al. |
| 6,107,624 A | 8/2000 | Doring et al. |
| 6,107,628 A | 8/2000 | Smith et al. |
| 6,124,592 A | 9/2000 | Spangler |
| 6,157,029 A | 12/2000 | Chutjian et al. |
| 6,157,031 A | 12/2000 | Prestage |
| 6,180,414 B1 | 1/2001 | Katzman |
| 6,188,067 B1 | 2/2001 | Chutjian et al. |
| 6,200,539 B1 | 3/2001 | Sherman et al. |
| 6,262,416 B1 | 7/2001 | Chutjian et al. |
| 6,281,494 B1 | 8/2001 | Chutjian et al. |
| 6,323,482 B1 | 11/2001 | Clemmer et al. |
| 6,479,815 B1 | 11/2002 | Goebel et al. |
| 6,495,823 B1 | 12/2002 | Miller et al. |
| 6,498,342 B1 | 12/2002 | Clemmer et al. |
| 6,504,149 B2 | 1/2003 | Guevremont et al. |
| 6,509,562 B1 | 1/2003 | Yang et al. |
| 6,512,224 B1 | 1/2003 | Miller et al. |
| 6,512,226 B1 | 1/2003 | Loboda et al. |
| 6,540,691 B1 | 4/2003 | Phillips |
| 6,618,712 B1 | 9/2003 | Parker et al. |
| 6,621,077 B1 | 9/2003 | Guevremont et al. |
| 6,639,212 B1 | 10/2003 | Guevremont |
| 6,653,627 B2 | 11/2003 | Guevremont |
| 6,690,004 B2 | 2/2004 | Miller et al. |
| 6,703,609 B2 | 3/2004 | Guevremont |
| 6,713,758 B2 | 3/2004 | Guevremont |
| 6,727,496 B2 | 4/2004 | Miller et al. |
| 6,744,043 B2 | 6/2004 | Loboda |
| 6,753,522 B2 | 6/2004 | Guevremont |
| 6,770,875 B1 | 8/2004 | Guevremont |
| 6,774,360 B2 | 8/2004 | Guevremont |
| 6,787,765 B2 | 9/2004 | Guevremont |
| 6,799,355 B2 | 10/2004 | Guevremont |
| 6,806,463 B2 | 10/2004 | Miller et al. |
| 6,806,466 B2 | 10/2004 | Guevremont |
| 6,815,668 B2 * | 11/2004 | Miller et al. ............... 250/286 |
| 6,815,669 B1 | 11/2004 | Miller et al. |
| 6,822,224 B2 | 11/2004 | Guevremont et al. |
| 6,825,461 B2 | 11/2004 | Guevremont et al. |
| 2001/0030285 A1 | 10/2001 | Miller et al. |
| 2002/0070338 A1 | 6/2002 | Loboda |
| 2002/0134932 A1 | 9/2002 | Guevremont et al. |
| 2003/0020012 A1 | 1/2003 | Guevremont |
| 2003/0038235 A1 | 2/2003 | Guevremont et al. |
| 2003/0052263 A1 | 3/2003 | Kaufman et al. |
| 2003/0070913 A1 | 4/2003 | Miller et al. |
| 2003/0089847 A1 | 5/2003 | Guevremont et al. |
| 2003/0132380 A1 | 7/2003 | Miller et al. |
| 2003/0146377 A1 | 8/2003 | Miller et al. |
| 2004/0094704 A1 | 5/2004 | Miller et al. |
| 2004/0136872 A1 | 7/2004 | Miller et al. |
| 2004/0232326 A1 | 11/2004 | Guevremont et al. |
| 2005/0029449 A1 | 2/2005 | Miller et al. |
| 2005/0040330 A1 | 2/2005 | Miller et al. |
| 2005/0051719 A1 | 3/2005 | Miller et al. |
| 2005/0056780 A1* | 3/2005 | Miller et al. ............... 250/288 |
| 2005/0121607 A1 | 6/2005 | Miller et al. |
| 2005/0133716 A1 | 6/2005 | Miller et al. |
| 2005/0139762 A1 | 6/2005 | Miller et al. |
| 2005/0167583 A1 | 8/2005 | Miller et al. |
| 2005/0173629 A1 | 8/2005 | Miller et al. |
| 2005/0194527 A1 | 9/2005 | Guevremont et al. |
| 2005/0194532 A1 | 9/2005 | Guevremont et al. |
| 2008/0054174 A1* | 3/2008 | Boyle et al. ............... 250/286 |

FOREIGN PATENT DOCUMENTS

| | | |
|---|---|---|
| SU | 966583 A | 10/1982 |
| SU | 1337934 | 9/1987 |
| SU | 1627984 A2 | 2/1991 |
| SU | 1405489 | 6/1998 |
| SU | 1412447 A1 | 6/1998 |
| SU | 1485808 A1 | 6/1998 |
| WO | WO 96/19822 A1 | 6/1996 |
| WO | WO 97/38302 | 10/1997 |
| WO | WO 99/21212 | 4/1999 |
| WO | WO 00/08454 | 2/2000 |
| WO | WO 00/08455 | 2/2000 |
| WO | WO 00/08456 | 2/2000 |
| WO | WO 00/08457 | 2/2000 |
| WO | WO 01/08197 | 2/2001 |
| WO | WO 01/08197 A1 | 2/2001 |
| WO | WO 01/22049 A2 | 3/2001 |
| WO | WO 01/35441 A1 | 5/2001 |
| WO | WO 01/69217 | 9/2001 |
| WO | WO 01/69217 A2 | 9/2001 |
| WO | WO 01/69647 A2 | 9/2001 |
| WO | WO 01/69920 A2 | 9/2001 |
| WO | WO 02/071053 A2 | 9/2002 |
| WO | W0 02/083276 | 10/2002 |
| WO | WO 03/005016 | 1/2003 |
| WO | WO 03/015120 | 2/2003 |
| WO | WO 03/067237 | 8/2003 |
| WO | WO 03/067242 | 8/2003 |
| WO | WO 03/067243 | 8/2003 |
| WO | WO 03/067625 | 8/2003 |
| WO | WO 2004/029603 | 4/2004 |
| WO | WO 2004/029614 | 4/2004 |
| WO | WO 2004/030022 | 4/2004 |
| WO | WO 2004/030023 | 4/2004 |
| WO | WO 2004/030129 | 4/2004 |
| WO | WO 2006/013396 | 2/2006 |
| WO | WO 2006/046077 | 5/2006 |
| WO | WO 2007/034239 | 3/2007 |

| WO | WO 2007/035825 | 3/2007 |
| WO | WO 2007/0342339 | 3/2007 |
| WO | WO 2007/041550 | 4/2007 |
| WO | WO 2007/041551 | 4/2007 |

OTHER PUBLICATIONS

Kolesar et al. "Review and Summary of a Silicon Micromachined Gas Chromatography System" IEEE Transactions on Components, Packaging and Manufacturing Technology. Part B: Advanced Packaging, IEEE Service Center, Piscataway, NJ, US, vol. 21, No. 4, Nov. 1998.

Kolesar et al. "Silicon micromachined gas chromatography system" 1997 Proceedings of the 2nd Annual IEEE International Conference on Innovative Systems in Silicon. ISIS '97. Austin, TX, Proceedings of the Annual IEEE International Conference on Innovative Systems in Silicon, New York, NY: IEEE, US, Oct. 8, 1997, pp. 117-125.

Sasaki et al. "Gas chromatography with Fourier transform infared and mass spectral definition" Journal of Chromatography A, Elsevier, Amsterdam, NL, vol. 842, No. 1-2, May 21, 1999, pp. 341-349.

Buryakov et al., "Separation of ions according to mobility in a strong AC electric field," Letters to Journal of Technical Physics 17:11-12 (1991).

Guevremont et al., "Atmospheric pressure ion focusing in a high-field asymmetric waveform ion mobility spectrometer," Review of Scientific Instruments 70:2:1370-1383.

Buryakov et al., "A new method of separation of multi-atomic ions by mobility at atmospheric pressure using a high-frequency amplitude-asymmetric strong electric field," Inter. J. of Mass Spectrometry and Ion Processes, Elsevier Scientific Pub. Co., Amsterdam, NL, 128:143-148 XP000865595 ISSN:-168-1176 absract (1993).

Miller, R.A., et al., "A Novel Micromachined High-Field Asymmetric Waveform-Ion Mobility Spectrometer," Sensors and Actuators B, B67(3):300-306 (2000).

Buryakov, I.A., et al., Device and Method for Gas Electrophoresis, Chemical Analysis of Environment, edit. Prof. V. V. Malakhov, Novosibirsk: Nauka, (1991) 113-127.

Carnahan, B., et al., "Field Ion Spectrometry—A New Analytical Technology for Trace Gas Analysis," ISA Paper 96-009:87-96 (1996).

Handy, R., et al., "Determination of nonomolar levels of perchlorate in water by ESI-FAIMS-MS," JAAS, 15:907-911 (2000).

Guevremont et al., "High Field Asymmetric Waveform Ion Mobility Spectrometry-Mass Spectrometry: An Investigation of Leucine Enkephalin Ions Produced by Electrospray Ionization," J. Am. Soc. Mass. Spectrom. 10:492-501 (1999).

Krylov, "A Method of Reducing Diffusion Losses in a Drift Spectrometer," Technical Physics, 44(1):113-116.

Riegner et al., "Qualitative Evaluation of Field Ion Spectrometry for Chemical Warfare Agent Detection," Proceedings of the ASMS Conference on Mass Spectrometry and allied Topics, pp. 473A-473B (1997).

Carnahan et al., "Field Ion Spectrometry—A New Technology for Cocaine Heroin Detection," SPIE, 2937:106-109 (1997).

Barnet et al., "Isotope Separation Using High-Filed Asymmetric Waveform Ion Mobility Spectrometry," Nuclear Instruments & Methods in Physics Research, 450(1):179-185 (2000).

Guevremont et al., "Calculation of Ion Mobilities from Electrospray Ionization High Field Asymmetric Waveform Ion Mobility Spectrometry Mass Spectrometry," Journal of Chemical Physics, 114(23):10270-10277 (2001).

Pilzecker et al., "On-Site Investigations of Gas Insulated Substations Using Ion Mobility Spectrometry for Remote Sensing of SF6 Decomposition," IEEE, pp. 400-403 (2000).

"A Micromachined Field Driven Radio Frequencey-Ion Mobility Spectrometer for Trace Level Chemical Detection," A Draper Laboratory Proposal Against the "Advanced Cross-Enterprise Technology Development for NASA Missions," Solicitation, NASA NRA 99-OSS-05.

Eiceman et al., "Miniature radio-frequency mobility analyzer as a gas chromatogrphic detector for oxygen-containing volatile organic compounds, pheromones and other insect attractants," Journal of Chromatography, vol. 917, pp. 205-217 (2001).

Miller et al., "A MEMS Radio-Frequency Ion Mobility Spectrometer for Chemical Agent Detection," Proceedings of the 2000 SolidState Sensors and Actuators Workshop (Hilton Head, SC, Jun. 2000).

Miller et al., "A MEMS radio-frequency ion mobility spectrometer for chemical vapor detection," Sensors and Actuators, vol. 91, pp. 301-312 (2001).

Schneider et al., "High Sensitivity GC-FIS for Simultaneous Detection for Chemical Warfare Agents," Journal of Process Analytical Chemistry, vol. 5, Nos. 3, 4, pp. 124-136 (2000).

Phillips, M., "Method for the Collection and Assay of Volatile Organic Compounds in Breath," Analytical Biochemistry, 247:272-278 (1997).

Shute et al., "Curie-point Pyrolysis Mass Spectrometry Applied to Characterization and Indentification of Selected *Bacillus* Species," J. Gen. Microbiology, 130:343-355 (1984).

Krylov, E.V., "Comparison of the Planar and Coaxial Field Asymmetrical Waveform Ion Mobility Spectrometer (FAIMS)," International Journal of Mass Spectrometry, 225, (2003) pp. 39-51.

\* cited by examiner

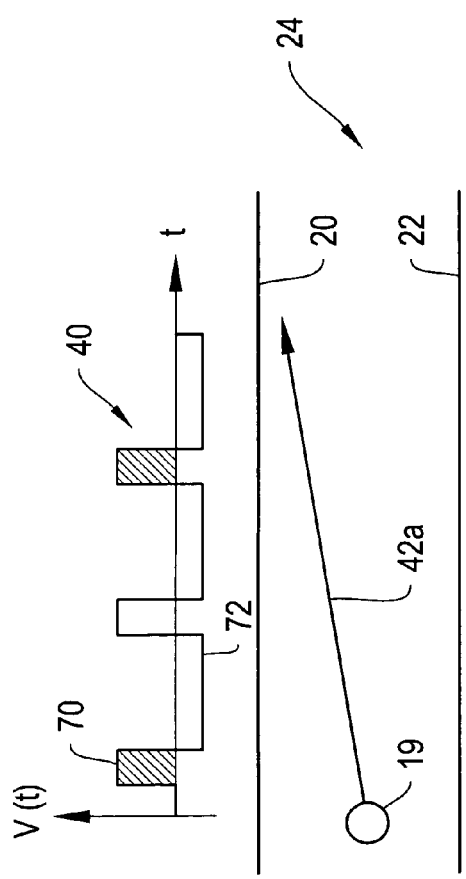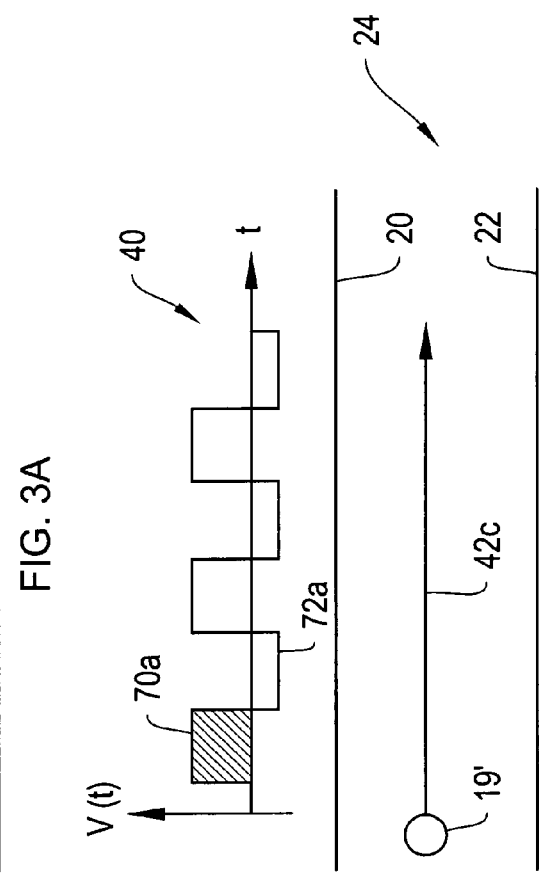
FIG. 3A
FIG. 3B

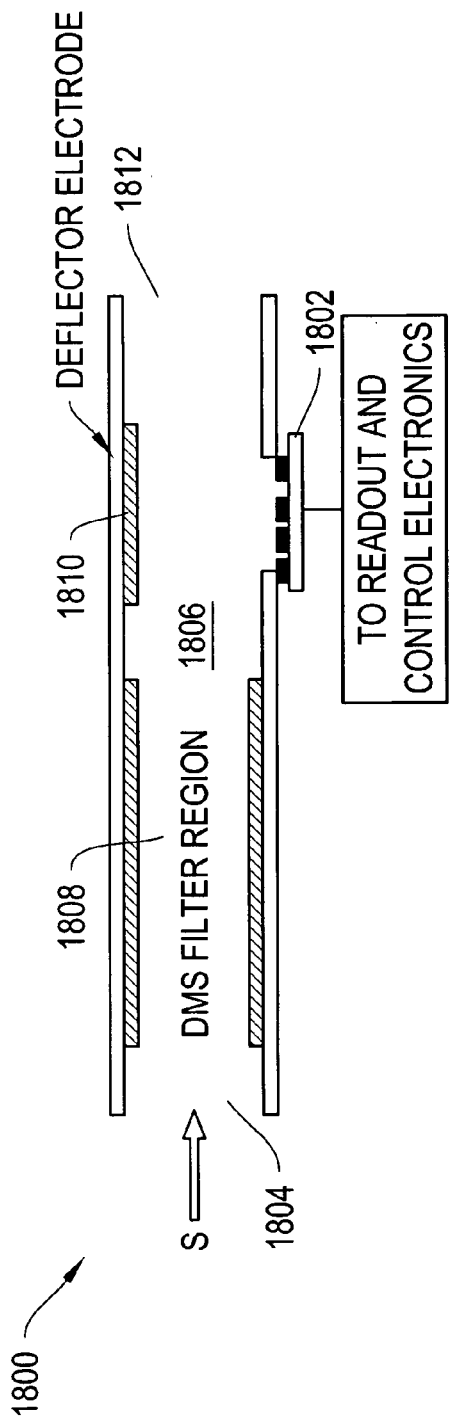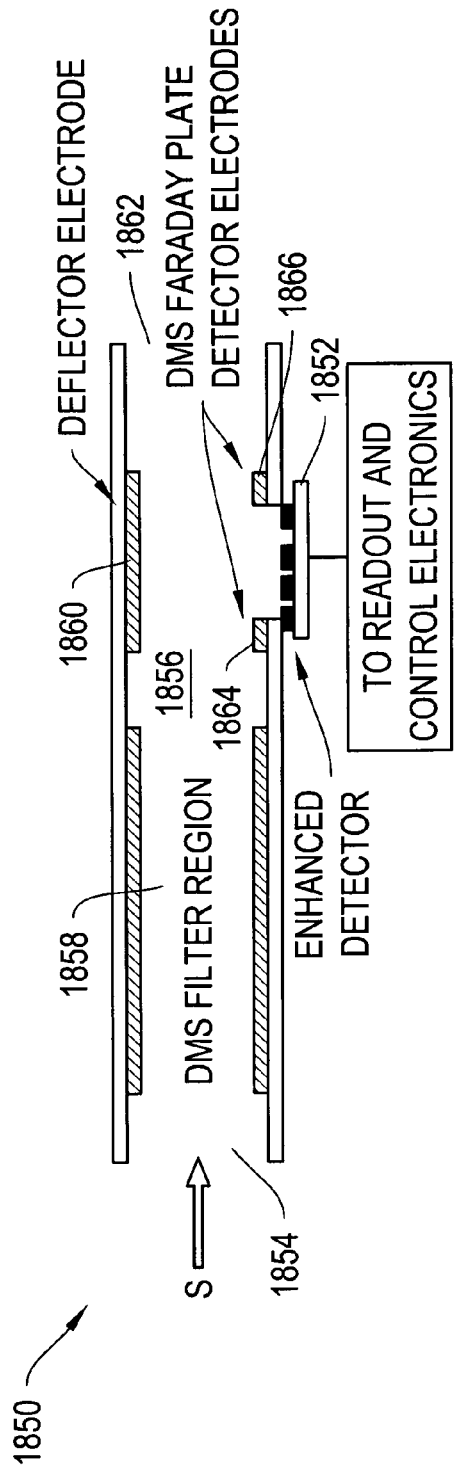

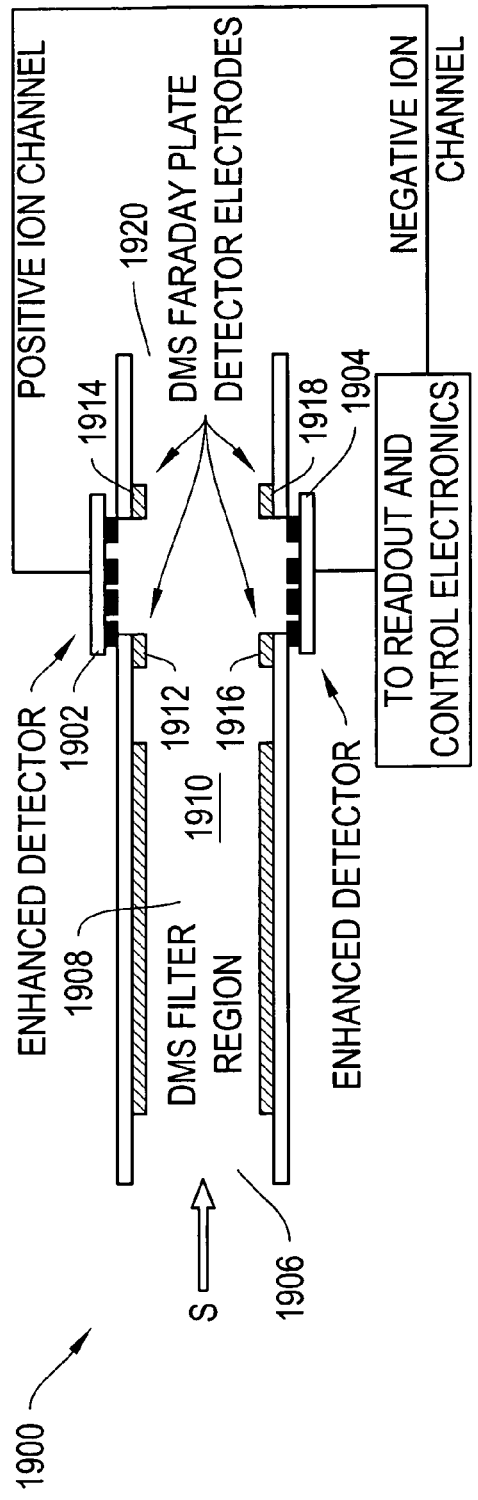
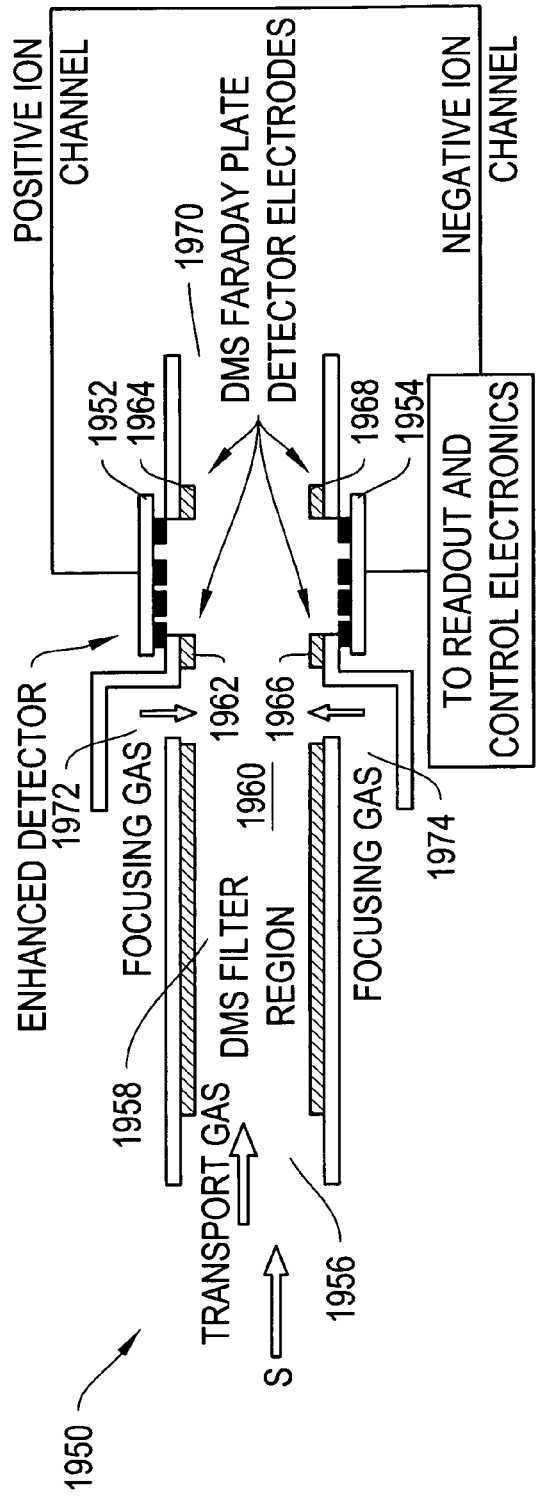
FIG. 32
FIG. 33

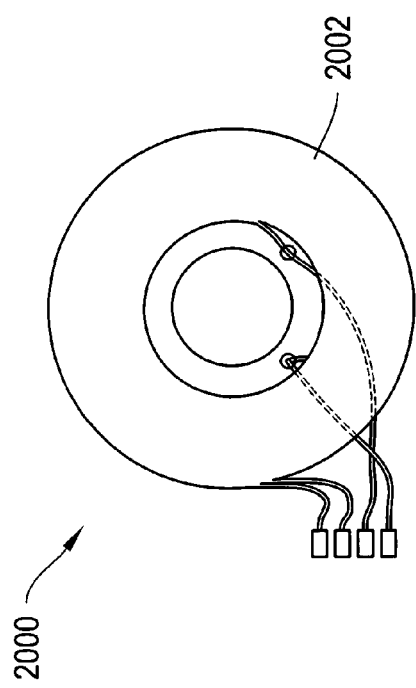
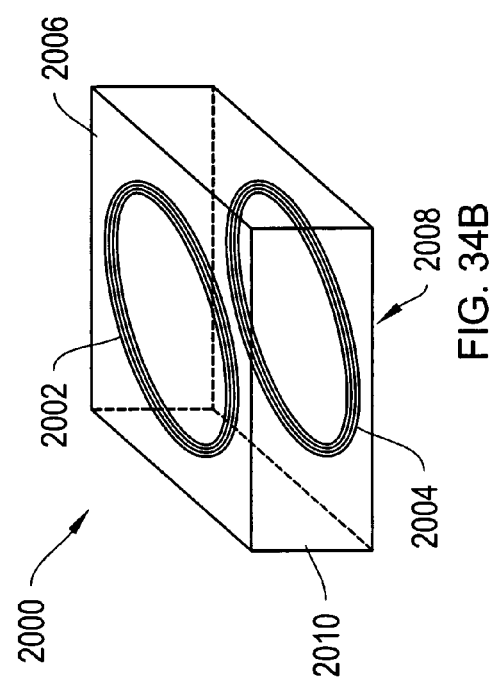
FIG. 34A
FIG. 34B

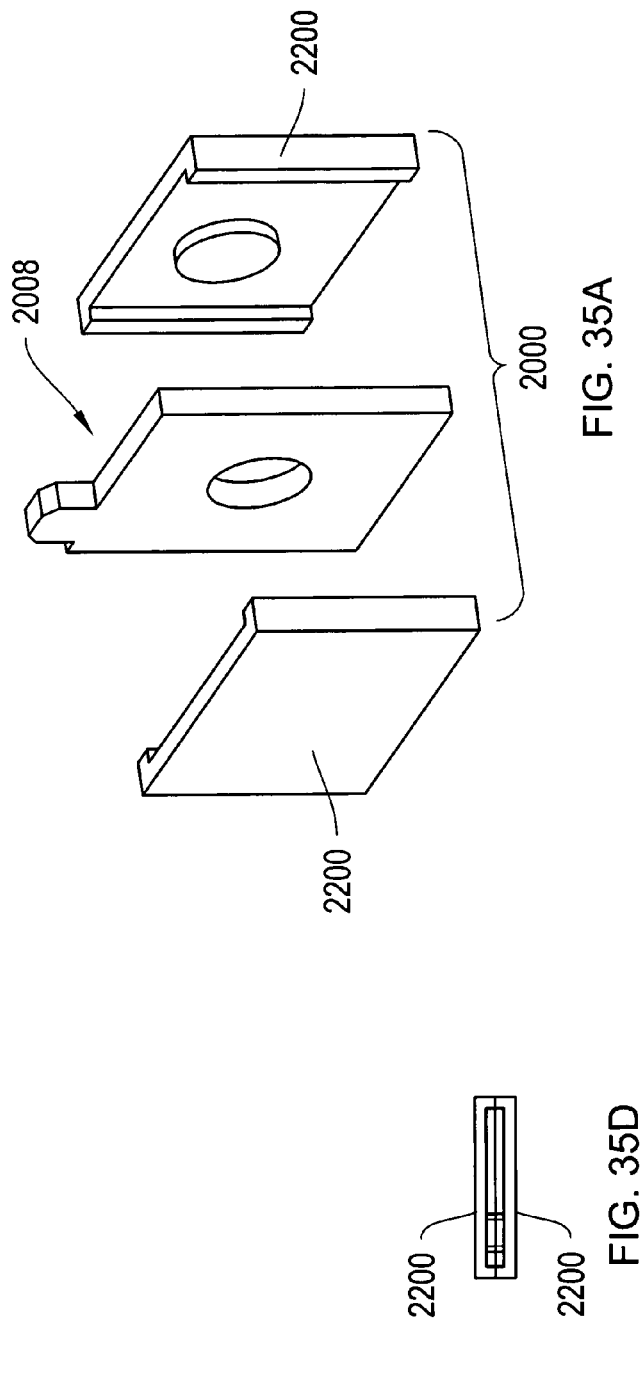

ULTRA COMPACT ION MOBILITY BASED ANALYZER APPARATUS, METHOD, AND SYSTEM

REFERENCE TO RELATED APPLICATIONS

This application claims priority to and the benefit of: U.S. Provisional Application No. 60/702,376, filed on Jul. 26, 2005, entitled "Methods and Apparatus For Analyzing A Sample Using A Compact Differential Mobility Spectrometer"; U.S. Provisional Application No. 60/710,634, filed on Aug. 23, 2005, entitled "Differential Ion Mobility Spectrometer Including Faraday Plate Detector"; U.S. Provisional Application No. 60/723,641, filed on Oct. 5, 2005, entitled "Method and Apparatus For Enhanced Control of Voltage and Electric Fields in Ion Mobility Based Devices"; U.S. Provisional Application No. 60/750,546, filed on Dec. 15, 2005, entitled "Ultra Compact Ion Mobility Based Analyzer Apparatus, Method, and System"; and U.S. Provisional Application No. 60/753,300, filed on Dec. 21, 2005, entitled "Integrated Longitudinal Differential Mobility Spectrometer," all of which are incorporated herein by reference.

This application also incorporates by reference the entire contents of the following co-pending U.S. Patent Applications: U.S. Ser. No. 10/824,674, filed on 14 Apr. 2004; U.S. Ser. No. 10/887,016, filed on 8 Jul. 2004; U.S. Ser. No. 10/894,861, filed on 19 Jul. 2004; U.S. Ser. No. 10/903,497, filed on 30 Jul. 2004; U.S. Ser. No. 10/916,249, filed on 10 Aug. 2004; U.S. Ser. No. 10/932,986, filed on 2 Sep. 2004; U.S. Ser. No. 10/943,523, filed on 17 Sep. 2004; U.S. Ser. No. 10/981,001, filed on 4 Nov. 2004; U.S. Ser. No. 10/998,344, filed 24 Nov. 2004; U.S. Ser. No. 11/015,413, filed on 17 Dec. 2004; U.S. Ser. No. 11/035,800, filed on 13 Jan. 2005; U.S. Ser. No. 11/050,288, filed on 2 Feb. 2005; U.S. Ser. No. 11/070,904, filed on 3 Mar. 2005; U.S. Ser. No. 11/119,048, filed on 28 Apr. 2005; U.S. Ser. No. 11/293,651, filed on 3 Dec. 2005; U.S. Ser. No. 11/305,085, filed on 16 Dec. 2005; U.S. Ser. No. 11/331,333, filed on 11 Jan. 2006; and U.S. Ser. No. 11/415,564, filed on 1 May 2006.

FIELD OF THE INVENTION

The present invention relates to chemical analytical systems based on ion mobility and, more particularly, ultra compact ion mobility based analyzers.

BACKGROUND OF THE INVENTION

The ability to detect and identify explosives, drugs, chemical and biological agents as well as monitor air quality has become increasingly more critical given increasing terrorist and military activities and environmental concerns. Previous detection of such agents was accomplished with conventional mass spectrometers, time of flight (TOF) ion mobility spectrometers (IMS) and conventional field asymmetric ion mobility spectrometers (FAIMS), also known as differential mobility spectrometers (DMS).

Mass spectrometers (MS) are very sensitive and selective with fast response time. Mass spectrometers, however, are large and require significant amounts of power to operate. They also require a powerful vacuum pump to maintain a high vacuum in order to reduce ion neutral interactions and permit detection of the selected ions. Mass spectrometers are also very expensive.

Another spectrometric technique which is less complex is TOF IMS which is the method currently implemented in most portable chemical weapons and explosives detectors. The detection is based not solely on mass, but on charge and cross-section of the molecule as well. However, because of these different characteristics, molecular species identification is not as conclusive and accurate as the mass spectrometer. Time of flight ion mobility spectrometers typically have unacceptable resolution and sensitivity limitations when attempting to reduce their size. In time of flight ion mobility, the resolution is proportional to the length of the drift tube. The longer the tube the better the resolution, provided the drift tube is also wide enough to prevent all ions from being lost to the side walls due to diffusion. Thus, fundamentally, miniaturization of time of flight ion mobility systems leads to a degradation in system performance. While conventional time of flight devices are relatively inexpensive and reliable, they suffer from several limitations. First, the sample volume through the detector is small, so to increase spectrometer sensitivity either the detector electronics must have extremely high sensitivity, requiring expensive electronics, or a concentrator is required, adding to system complexity. In addition, a gate and gating electronics are usually needed to control the injection of ions into the drift tube.

FAIMS spectrometry, also known a differential mobility spectrometry (DMS), was developed in the former Soviet Union in the 1980's. FAIMS spectrometry allows a selected ion to pass through a filter while blocking the passage of undesirable ions. But the only commercial prior art FAIMS spectrometer was large and expensive, e.g., the entire device was nearly a cubic foot in size and cost over $25,000. Such systems are not suitable for use in applications requiring small detectors. They are also relatively slow, taking as much as one minute to produce a complete spectrum of the sample gas, are difficult to manufacture and are not mass producible.

The prior art FAIMS devices typically depend upon a carrier gas that flows in the same direction as the ion travel through the filter. However, the pumps required to draw the sample medium into the spectrometer and to provide a carrier gas can be rather large and can consume large amounts of power.

More recently, FAIMS systems have been implemented in compact micromachined form factors. Such relatively compact form factors have enabled reduced voltage, reduced power consumption, greater portability, longer battery lifetime, and greater integration flexibility. However, even smaller, ultra compact, form factors are desired to further improve the above advantages along with enabling a DMS to practically support additional applications.

One problem with certain micromachined FAIMS devices is the inability to maintain a pure, dehumidified, clean, or contamination free atmosphere within the filter. Certain multilayered micromachined FAIMS designs appear to be fundamentally flawed through the lack of control of purity of the supporting gas atmosphere and constancy of the same during use as a standalone analyzer with only a membrane inlet. Excursions in moisture will radically affect and degrade response and integrity of any analyzer response. Even the inclusion of molecular sieve components is problematic. Accordingly, there is a need to provide mechanisms that established a regulated and consistent atmosphere within certain multilayered micromachined filters.

Another problem is that ion mobility based systems, such as DMS or FAIMS, employ relatively inefficient, large form-factor, and high power-consuming power supplies to generate, for example, the asymmetric radio frequency (Vrf) and compensation (Vc or Vcomp) voltages that filter ions of a sample. In one example, a differential ion mobility spectrometer (DMS) may utilize over 13 watts to generate around a 1500 volt peak of Vrf. Thus, there is a need for enhanced generation and control designs which result in reduced system power consumption.

SUMMARY OF THE INVENTION

The present invention features an ion mobility based analyzer and/or spectrometer for filtering ions via a time varying or periodic electric field. The time varying field may include a symmetric or asymmetric electric field. The ion mobility based analyzer may include a FAIMS or DMS. The ion mobility based analyzer may also include an IMS, hybrid IMS/DMS analyzer, or any analyzer capable of separating or discriminating ions based on the mobility characteristics of the ions. In certain embodiments, ions are transported along a longitudinal ion flow path or a certain trajectory using an ion flow generator.

The ion mobility based analyzer may include an ion flow generator that provides ion propulsion via a local electric field in the flow path, within the ion filter, before the ion filter, after the ion filter, or having elements, such as electrodes, before and after the ion filter. In one aspect, operation of the invention enables the elimination or reduction of flow rate and power requirements of conventional gas flow. In another aspect, the invention employs a combination of gas flow and ion propulsion through a filter to effect analysis of a sample.

In a further aspect, the invention includes system for analyzing a sample including a multilayered chip assembly. The system includes a gas chromatograph (GC) layer including a micromachined GC column and a first ion mobility filter layer including a plurality of ion filter flow channels where each ion filter flow channel including a time-varying electric field. The time varying electric field is applied to the moving ions to discriminate between ions of the sample. The system also includes a detector layer including a detector for detecting at least a portion of the ions exiting the ion mobility filter layer.

In one configuration, the gas chromatograph (GC) layer includes a micromachined GC column outlet on a surface in fluid communication with another layer of the multilayered chip assembly. In another configuration, the detector layer includes a plurality of flow channels with each flow channel including at least one detector element for detecting a portion of ions exiting the ion mobility filter layer.

In one feature, the time-varying electric field includes an asymmetric electric field. The asymmetric electric field may include a compensation field. In another feature, the time-varying electric field includes a substantially symmetric electric field.

In one configuration, the invention includes a solid state flow generator for flowing a carrier gas through the ion mobility based filter layer. The flow generator may be outside or inside of the ion mobility based filter layer. In another configuration, the detector layer includes a plurality of flow channels where each flow channel includes first and second detector elements for detecting a portion of ions exiting the ion mobility filter layer. In one feature, the first detector element is biased to detect positive ions and the second detector element is biased to detect negative ions.

In another configuration, the first ion mobility based filter layer includes a first pair of opposing electrodes for generating a time varying electric field therebetween. The ion mobility based filter layer also includes a second pair of opposing electrodes that are biased in relation to the first pair of electrodes to generate an ion flow along a flow path including the first and second pair of electrodes.

In a further configuration, a second ion mobility based filter layer is in communication with at least one of the first ion mobility based filter layer and the detector layer. The second ion mobility based filter may include an IMS, DMS, or hybrid IMS/DMS analyzer.

In another aspect, the present invention includes an ion mobility based analyzer employing a compact time varying and compensation voltage generation system using enhanced voltage coupling techniques such as integrated chip based transformers.

In a further aspect, the present invention enable the removes of excess gas from a GC-ion mobility based analyzer system where the vent is provided upstream of the ion mobility based filter. Such a configuration is particularly advantageous for an open carrier gas based recirculation system where excess gas used in the GC column is compensated for by venting the system as opposed to venting at the ion mobility based analyzer exhaust. In an alternative configuration, a catalyst is employed within the ion mobility base analyzer to remove or condense excess gas from the recirculation system.

In yet another embodiment, the present invention employs an enhanced faraday plate detector which may be utilized with a planar or multilayer chip assembly type of ion mobility based analyzer system to enhance ion detection.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIGS. 3A, 3B provide graphical representation of an asymmetric periodic voltage having a compensating varying duty cycle, for filtering unwanted ions (FIG. 3A) and passing through the filter selected ion species (FIG. 3B) without a bias voltage.

FIG. 30 is a conceptual diagram of an ion mobility based analyzer including a Faraday based element array, according to an illustrative embodiment of the invention.

FIG. 31 is a conceptual diagram of an ion mobility based analyzer including a Faraday based element array and plate detector electrodes, according to an illustrative embodiment of the invention.

FIG. 32 is a conceptual diagram of an ion mobility based analyzer including both positive and negative ion detection using Faraday based element arrays, according to an illustrative embodiment of the invention.

FIG. 33 is a conceptual diagram of an ion mobility based analyzer including both positive and negative ion detection using Faraday based element array along with focusing gas inlets, according to an illustrative embodiment of the invention.

FIG. 34A is a top view of a PCB transformer 2000 including primary windings 2002, according to an illustrative embodiment of the invention.

FIG. 34B is a perspective view of the PCB transformer 2000, according to an illustrative embodiment of the invention.

FIGS. 35A-D provide various views of one embodiment of a PCB transformer including an exploded view, a closed side view, another side view, and a top view, according to an illustrative embodiment of the invention.

DETAILED DESCRIPTION OF THE INVENTION

A preferred embodiment of the present invention provides method and apparatus for conveyance of ions in and through an ion filter without the need for a carrier gas in an ion mobility based analytical system. In embodiments of the present invention, the need for pumps is either eliminated or the pumps are made smaller, even micromachined. Furthermore, separate flow paths for the source gas and the carrier gas are not required. In one filter embodiment, filtered gas is introduced to flow in a direction opposite the direction of ion travel to eliminate ion clustering and to improve system sensitivity. Preferred and alternative embodiments of the invention are set forth below as an illustration and as a limitation.

Figure 1:
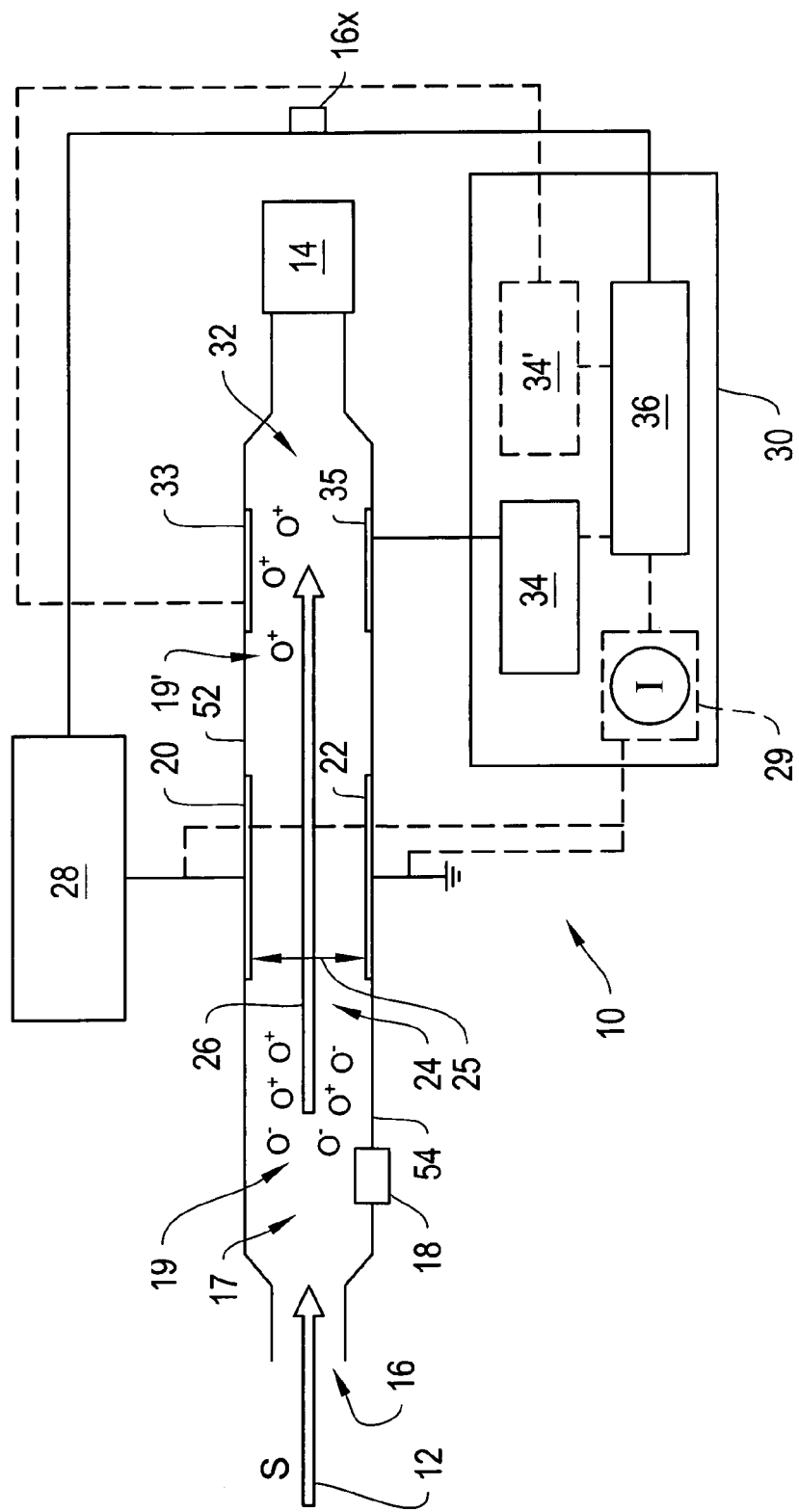
FIG. 1 is a schematic block diagram of a PFAIMS filter and detection system according to the present invention.

In one embodiment, a planar ion mobility based analyzer 10, FIG. 1, operates by drawing a carrier gas 12 containing a sample S to be analyzed (often collectively referred to as a gas sample), by means of pump 14, through inlet 16 and into ionization region 17. The gas sample is ionized by ionization source 18. Source 18 may include an ultraviolet light source, a radioactive device, plasma source, corona discharge device, electrospray head, or the like.

The ions 19 flow from the ionization region 17 along flow path 26 into filter 24 defined by facing electrodes 20 and 22. As these ions pass between electrodes 20 and 22 they are exposed to an asymmetric electric field 25 established between the filter electrodes, induced by a voltage applied from a source, such as voltage generator 28 directed by electronic controller 30. Filter field 25 is transverse to the longitudinal flow of gas and ions along flow path 26.

The system is preferably driven by electronic controller 30, which may include, for example, amplifier 34 and microprocessor 36. Amplifier 34 amplifies the output of detector 32, which is a function of the charge collected by electrode 35 and provides the output to microprocessor 36 for analysis. Similarly, amplifier 34', shown in phantom, may be provided where electrode 33 is also utilized as a detector.

As part of the ion mobility based analyzer filtering function, some compensation must be applied to the filter; which in turn selects a particular ion species that will pass through the filter. In operation, as ions pass through filter field 25, some ions are neutralized as they travel into and collide with filter electrodes 20 and 22. However the filter field is compensated to bring a particular species of ion back toward the center of the flow path, preventing it from being neutralized. Thus a desired ion species 19' passes through the filter.

Figure 2:
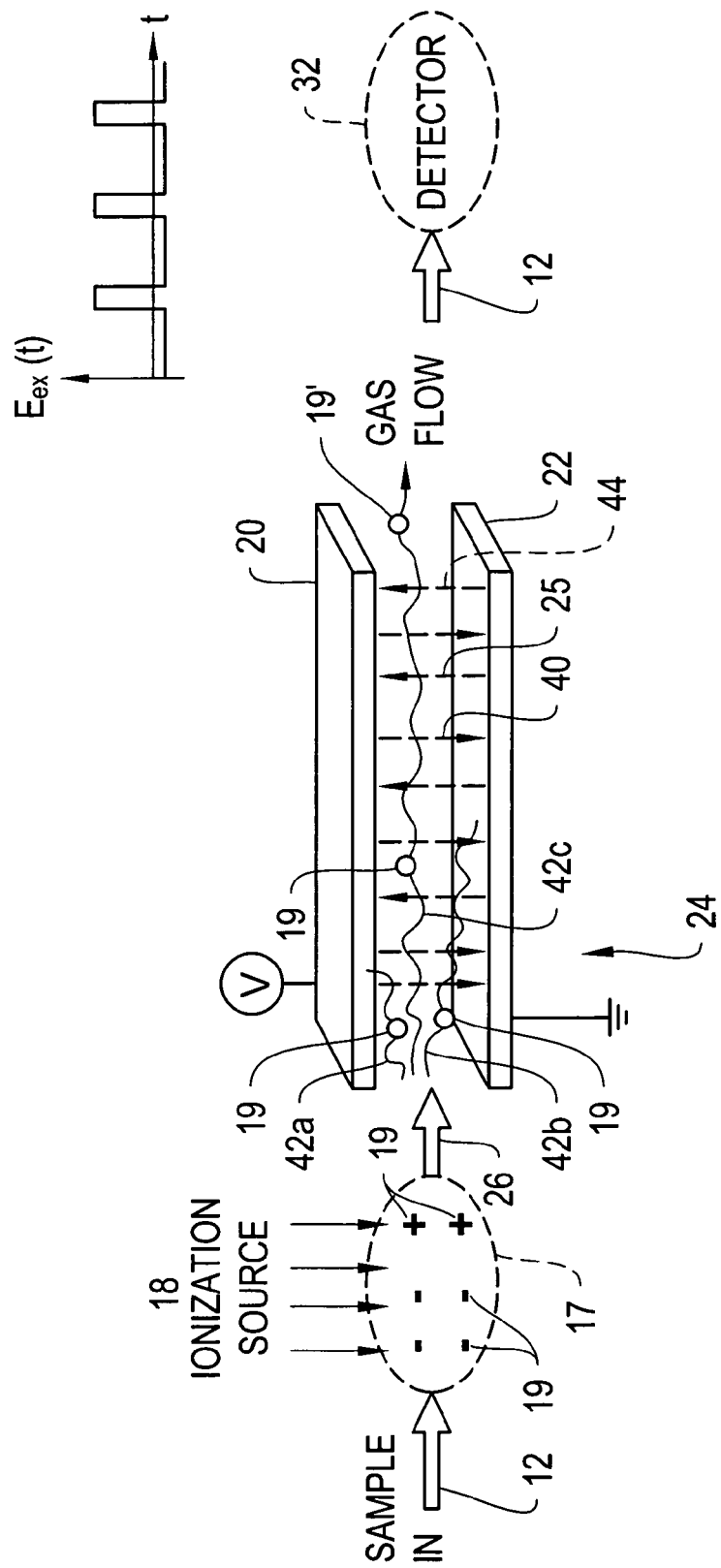
FIG. 2 is a schematic representation of the ions as they pass through the filter electrodes of FIG. 1 toward the detector.

More specifically, as shown in FIG. 2, ions 19 flow in the alternating asymmetric electric field 25, in oscillating paths 42*a*, 42*b* and 42*c*. The time varying RF voltage V applied to the filter electrodes is typically in the range of ±(1000-10,000) volts and creates electric field 25 with a maximum field strength of around 40,000 V/cm. The path taken by a particular ion is mostly a function of its size, cross-section and charge. Where the time varying electric field such as an asymmetric field is not compensated for the resulting high-low-field offset imposed on the ions, then the ions will reach and contact electrode 20 or 22 and will be neutralized. Thus as compensation is applied to the filter field, a particular ion species will be returned back toward the center of the flow path and will pass through the filter for detection.

In a particular embodiment, compensation is achieved by applying a compensation field 44, typically in the range of ±2000 V/cm from an applied ±100 volt dc voltage, for example, applied concurrently and induced at, adjacent to, or between, electrodes 20 and 22, via a bias voltage applied thereto. Now a selected ion species 19' passes through filter 24 for detection.

In one embodiment, compensation field 44 is a constant bias which offsets alternating asymmetric field 25 to allow the selected ion species 19' to pass to detector 32. Thus, with the proper bias voltage, a particular species of ion will follow path 42*c* while undesirable ions will follow paths 42*a* and 42*b* to be neutralized as they encounter electrode plates 20 and 22.

In an alternative practice of the invention, the duty cycle of the asymmetric periodic voltage applied to electrodes 20 and 22 of filter 24 is varied so that there is no need to apply a compensation voltage. The control electronics varies the duty cycle of asymmetric alternating electric field 25, with the result that path of a selected ion species (defined mostly by charge and cross-section, among other characteristics, of the ions) is returned toward the center of the flow path, and so to pass on for detection. As an example, and not by way of limitation, the duty cycle of field 25 may be one quarter: 25% high, peak 70, and 75% low, valley 72; in which case, ions 19 on path 42*a* approach and collide with a filter electrode 20 and are neutralized (FIG. 3A). However, by varying the duty cycle to 40%, peak 70*a*, 60% low, valley 72*a*, ions 19' on path 42*c* pass through filter 24 and toward the detector without being neutralized. Typically the duty cycle is variable from 10-50% high and 90-50% low (FIG. 3B). Accordingly, by varying the duty cycle of field 25 an ion's path in field 25 may be corrected so that it will pass through filter 24 without being neutralized and without the need for a compensating bias voltage.

Ions 19' that pass through filter 24 are now delivered for detection, which may be on-board or not. In a preferred embodiment, the detector is on board and is in the flow path. In one embodiment, detector 32 includes a biased top electrode 33 at a voltage and a biased bottom electrode 35, possibly at ground, formed on the same substrates as the filter electrodes. Top electrode 33 can be set at the same polarity as the ions to be detected and therefore deflects ions toward electrode 35. However, either electrode may detect ions depending on the passed ion species and bias applied to the electrodes. Moreover, multiple ions may be detected by using top electrode 33 as one detector and bottom electrode 35 as a second detector.

The output of ion mobility based analyzer 10 is a measure of the amount of charge detected at detector 32 for a given RF field 25 and compensation. The longer the filter 24 is set at a given compensation level, the more of a given species will be passed and the more charge will accumulate on detector 32.

Alternatively, by sweeping compensation over a predetermined voltage range, a complete spectrum for the sample and gas can be achieved. A ion mobility based analyzer according to the present invention requires typically less than thirty seconds and as little as one second or less to produce a complete spectrum for a given gas sample. Thus, by varying compensation during a scan, a complete spectrum of the gas sample can be generated.

Figure 4:
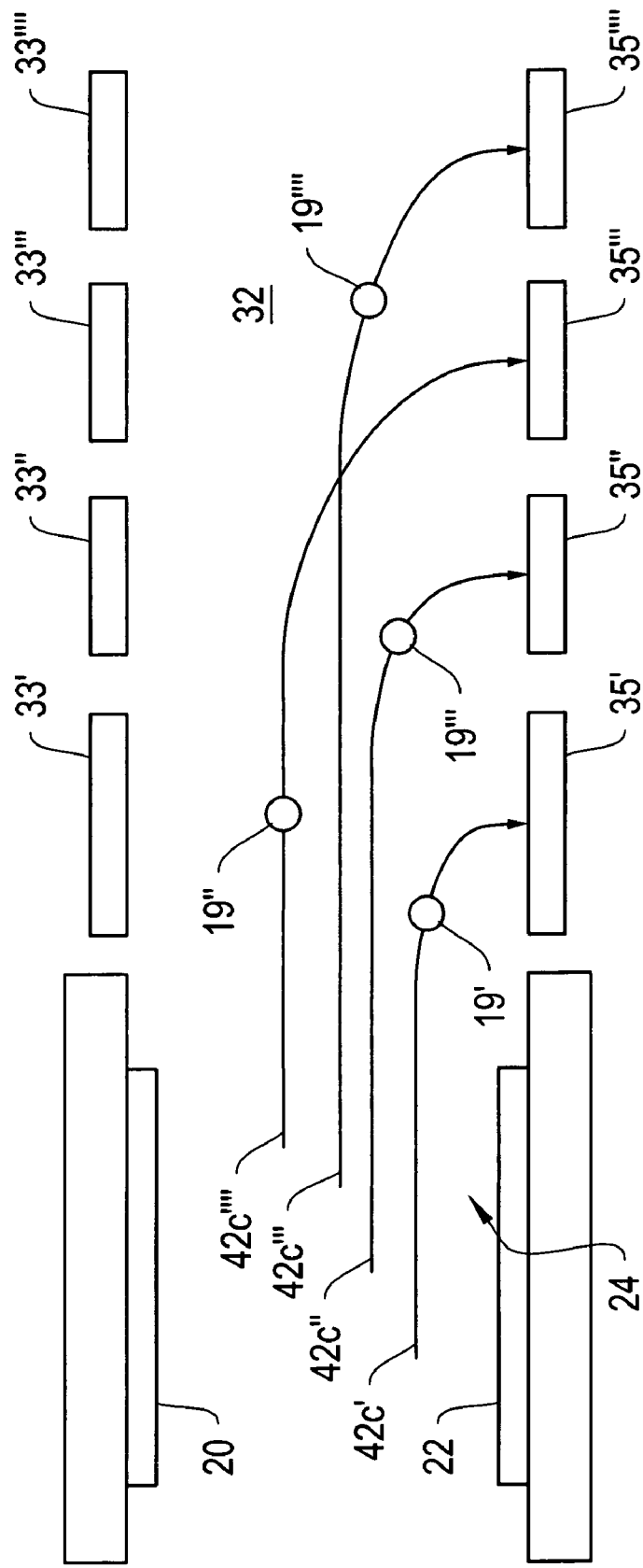
FIG. 4 is a schematic diagram of a segmented detector embodiment of the invention.

To improve ion mobility based analyzer 10 resolution even further, detector 32, may be segmented, as shown in FIG. 4. As ions pass through filter 24 between filter electrodes 20 and 22, the individual ions 19'-19''' may be detected spatially, the ions having their trajectories 42*c*'-42*c*'''' determined according to their size, charge and cross section. Thus detector segment 33' will have a concentration of one species of ion while detector segment 33'' will have a different ion species concentration, increasing the spectrum resolution as each segment may detect a particular ion species.

Figure 5A:
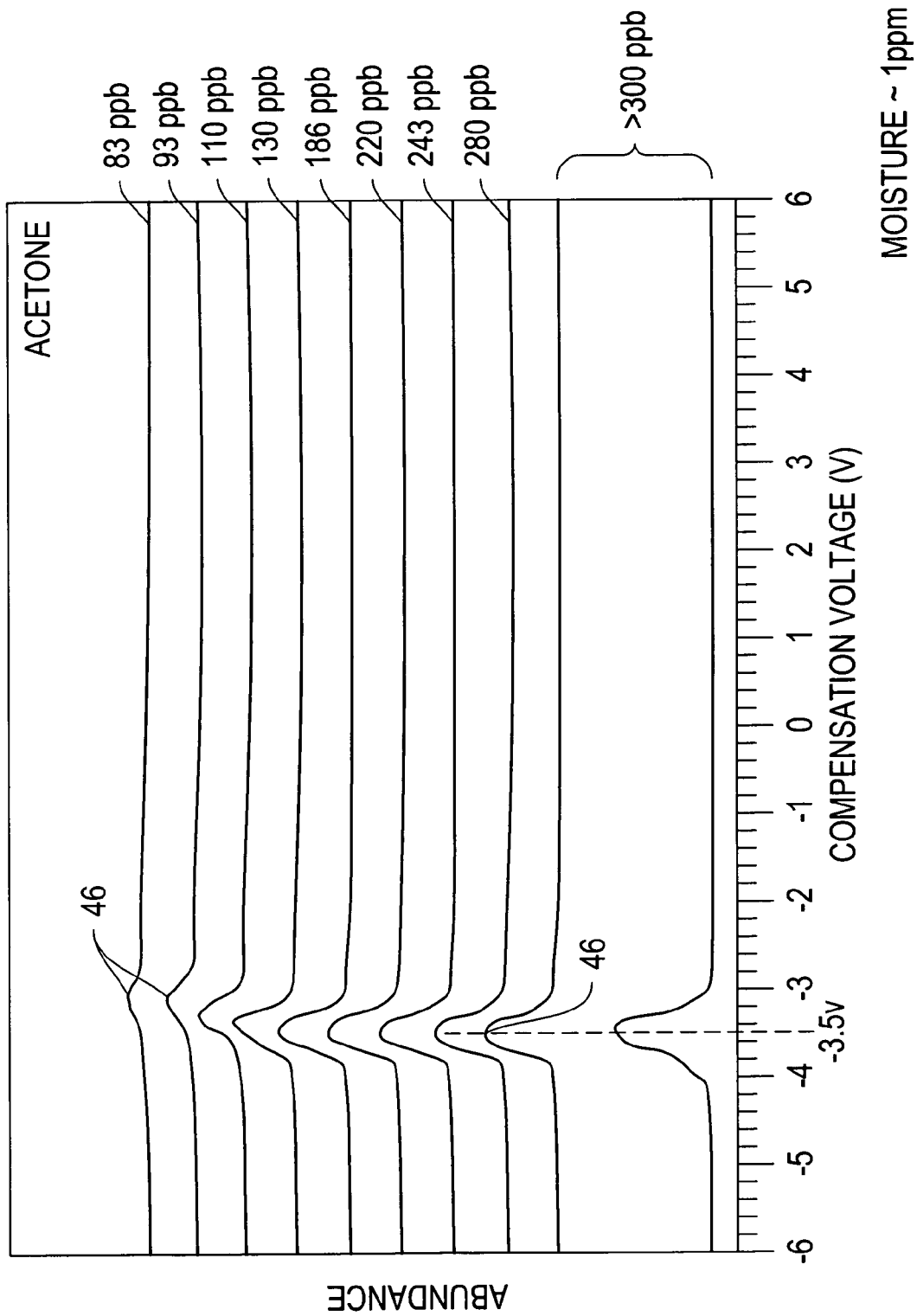
FIGS. 5A and 5B are graphical representations of the spectrometer response to varying concentrations of acetone and di-ethylmethyl amine in an embodiment of the invention.
Figure 5B:
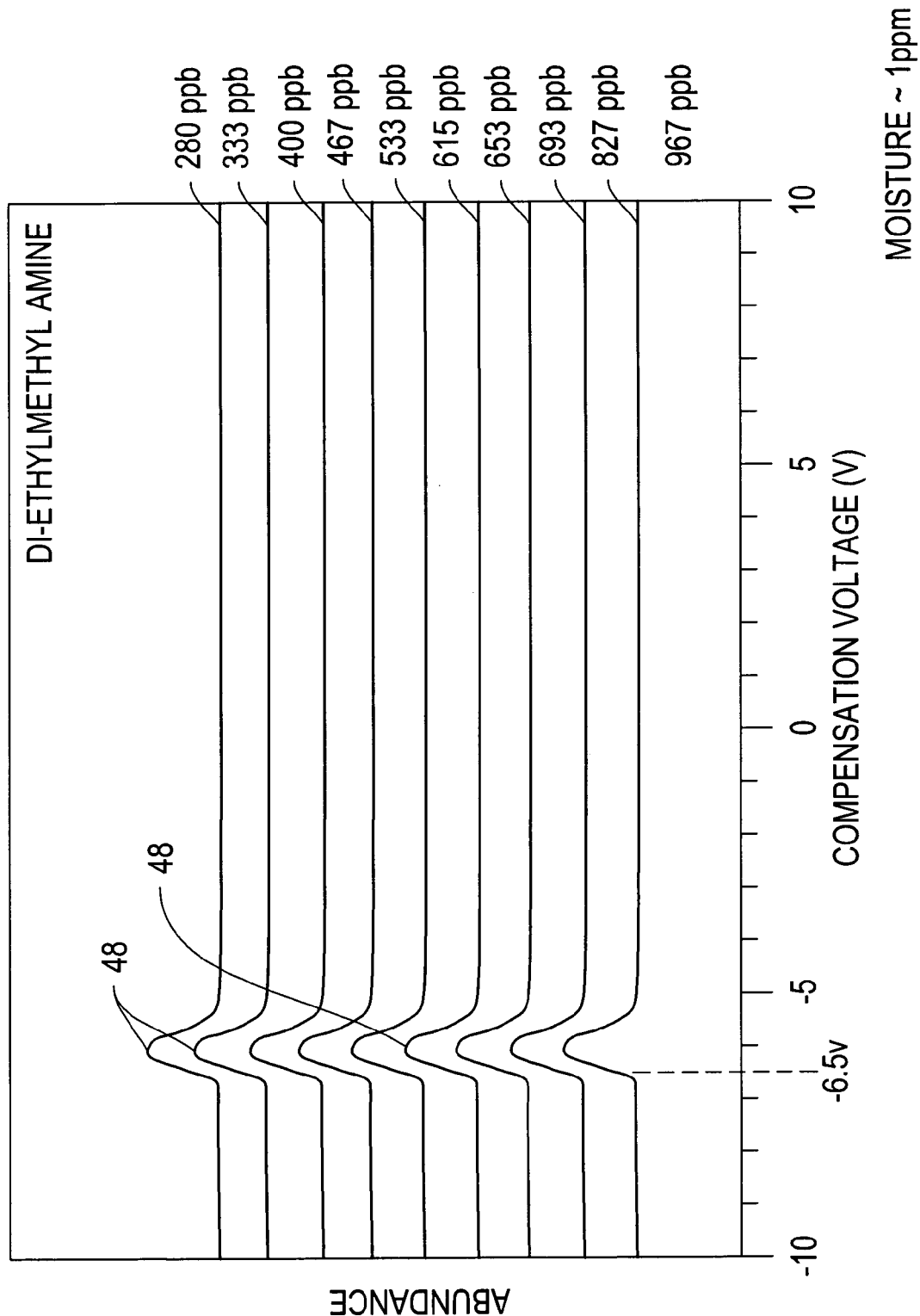

A ion mobility based analyzer as set forth herein is able to detect and discriminate between a wide range of compounds, and can do so with high resolution and sensitivity. As shown in FIG. 5A, varying concentrations of acetone that were clearly detected in one practice of the invention, with definitive data peaks 46 at −3.5 volts compensation. These were detected even at low concentrations of 83 parts per billion. With the bias voltage set at −6.5 volts, FIG. 5B, varying concentrations of diethyl methyl amine were clearly detected in practice of the invention, generating data peaks 46; these were detected in concentrations as low as 280 parts per billion.

Figure 6:
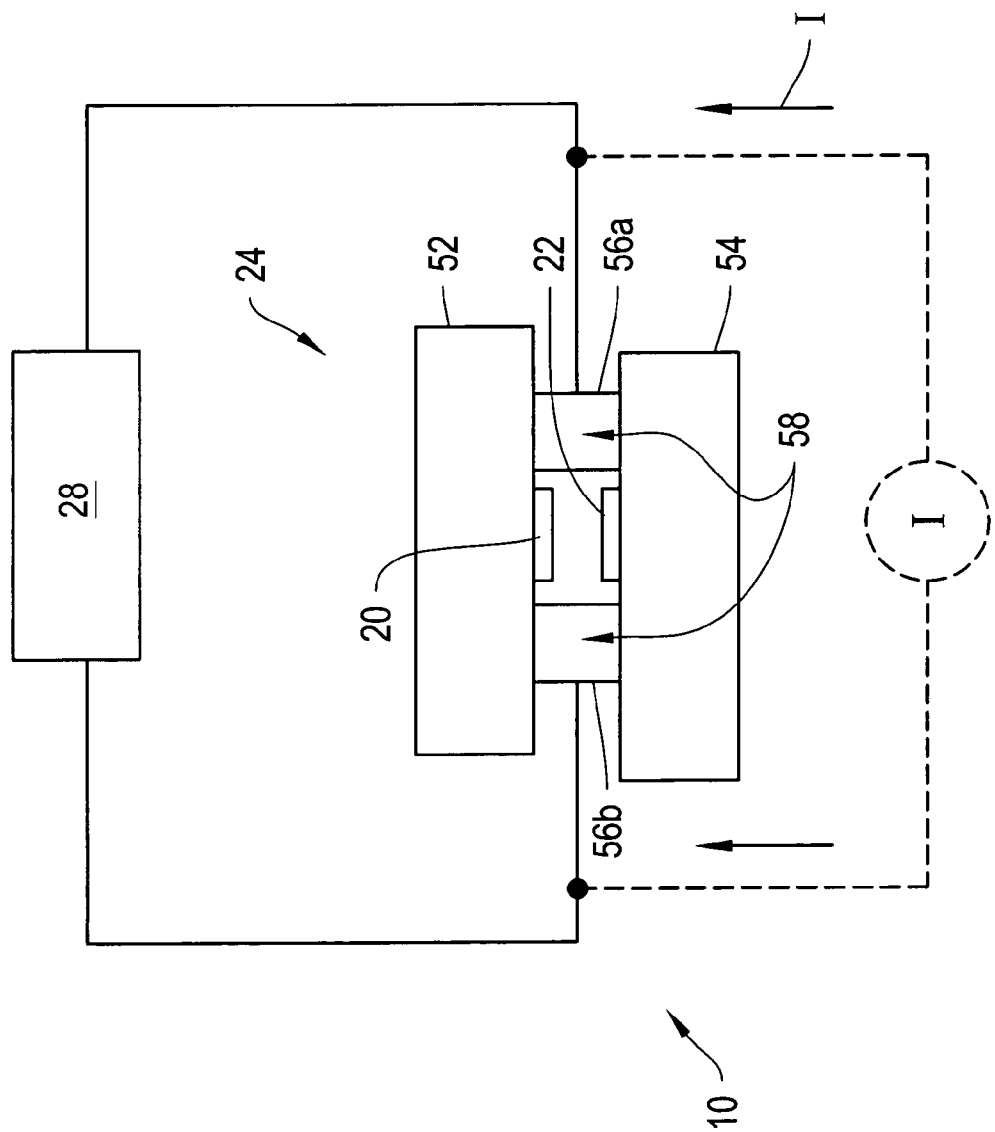
FIG. 6 is a cross sectional view of a spaced, micromachined filter assembly, according to an embodiment of the present invention.
Figure 7:
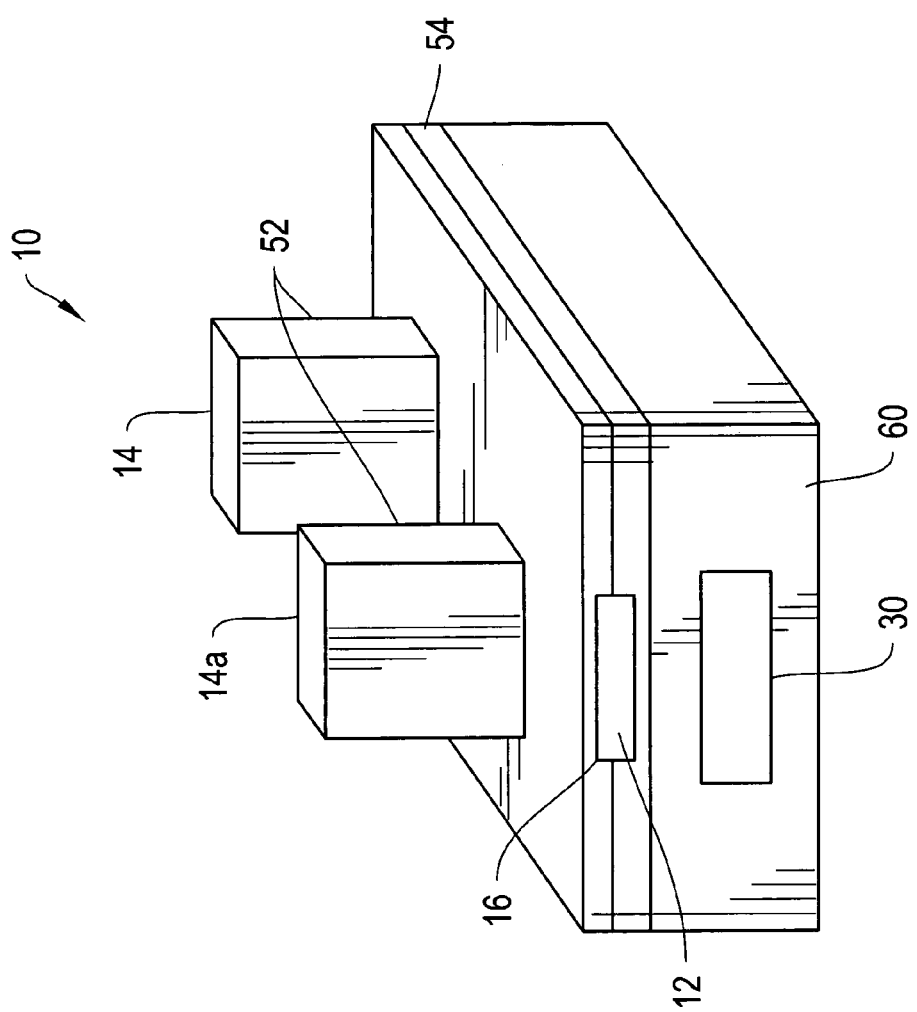
FIG. 7 is a perspective view of a practice of the invention as a packaged micromachined filter and detection system, including pumps, in miniaturized format.

Turning to FIG. 6 and FIG. 7, an embodiment of spectrometer 10 includes spaced substrates 52 and 54, for example glass or ceramic, and electrodes 20 and 22, which may be for example gold, titanium, or platinum, mounted or formed on substrates 52 and 54, respectively. Substrates 52 and 54 are separated by spacers 56*a-b* which may be formed by etching or dicing silicon wafer. The thickness of spacers 56*a*, 56*b* defines the distance between electrodes 20 and 22.

In one embodiment, a voltage is applied to silicon spacers 56*a-b*, ±(10-1000 volts dc), which transforms spacers 56*a* and 56*b* into electrodes to produce a confining electric field 58. Field 58 guides or confines the ions' paths to the center of flow path 26 in order to obtain more complete sample collection. As will be understood by a person skilled in the art, spacer electrodes 56*a-b* must be set to the appropriate voltage so as to "push" the ions toward the center of flow path 26. More ions traveling in the center of the path makes possible the result of more ions striking electrodes 33 and 35 for detection. However, this is not a necessary limitation of the invention.

Embodiments of the invention are compact with low parts count, where the substrates and spacers act to both contain the flow path and also to provide for a structural housing of the invention. Thus, the substrates and spacers serve multiple functions, both for guiding the ions and for containing the flow path.

In order to further assure accurate and reliable operation of spectrometer 10, neutralized ions which accumulate on electrode plates 20 and 22 are purged. In one embodiment this may be accomplished by heating flow path 26. For example, controller 30, FIG. 1, may include current source 29, shown in phantom in FIG. 6, which provides, in response to microprocessor 36, a current I to electrode plates 20 and 22 to heat the electrodes for removing accumulated neutrals. Optionally, current I may additionally or instead be applied to spacer electrodes 56a and 56b, to heat flow path 26 to purge electrodes 20 and 22.

A packaged ion mobility based analyzer 10 may be reduced in size to perhaps one inch by one inch by one inch. Pump 14 is mounted on substrate 52 for drawing gas sample 12 into inlet 16. Clean dry air may be introduced into flow path 26 by recirculation pump 14a prior to or after ionization of the gas sample. Electronic controller 30 may be etched into silicon control layer 60 which combines with substrates 52 and 54 to form a housing for spectrometer 10. Substrates 52 and 54 and control layer 60 may be bonded together, for example, using anodic bonding, to provide an extremely small ion mobility based analyzer. Micro pumps 14 and 14a provide a high volume throughput which further expedites the analysis of gas sample 12. Pumps 14 and 14a may be, for example, conventional miniature disk drive motors fitted with small centrifugal air compressor rotors or micromachined pumps, which produce flow rates of 1 to 4 liters per minute.

In practice of ion detection, generally speaking, sample ions tend to be found in either monomer or cluster states. It has been found that the relationship between the amount of monomer and cluster ions for a given ion species is dependent of the concentration of sample and the particular experimental conditions (e.g., moisture, temperature, flow rate, intensity of RF-electric field). Both the monomer and cluster states provide useful information for chemical identification. It will be useful to investigate the same sample separately in a condition which promotes clustering and in an environment that promotes the formation of only the monomer ions. A two channel ion mobility based analyzer of an embodiment such as shown in FIG. 8 can be used toward this end.

Figure 8:
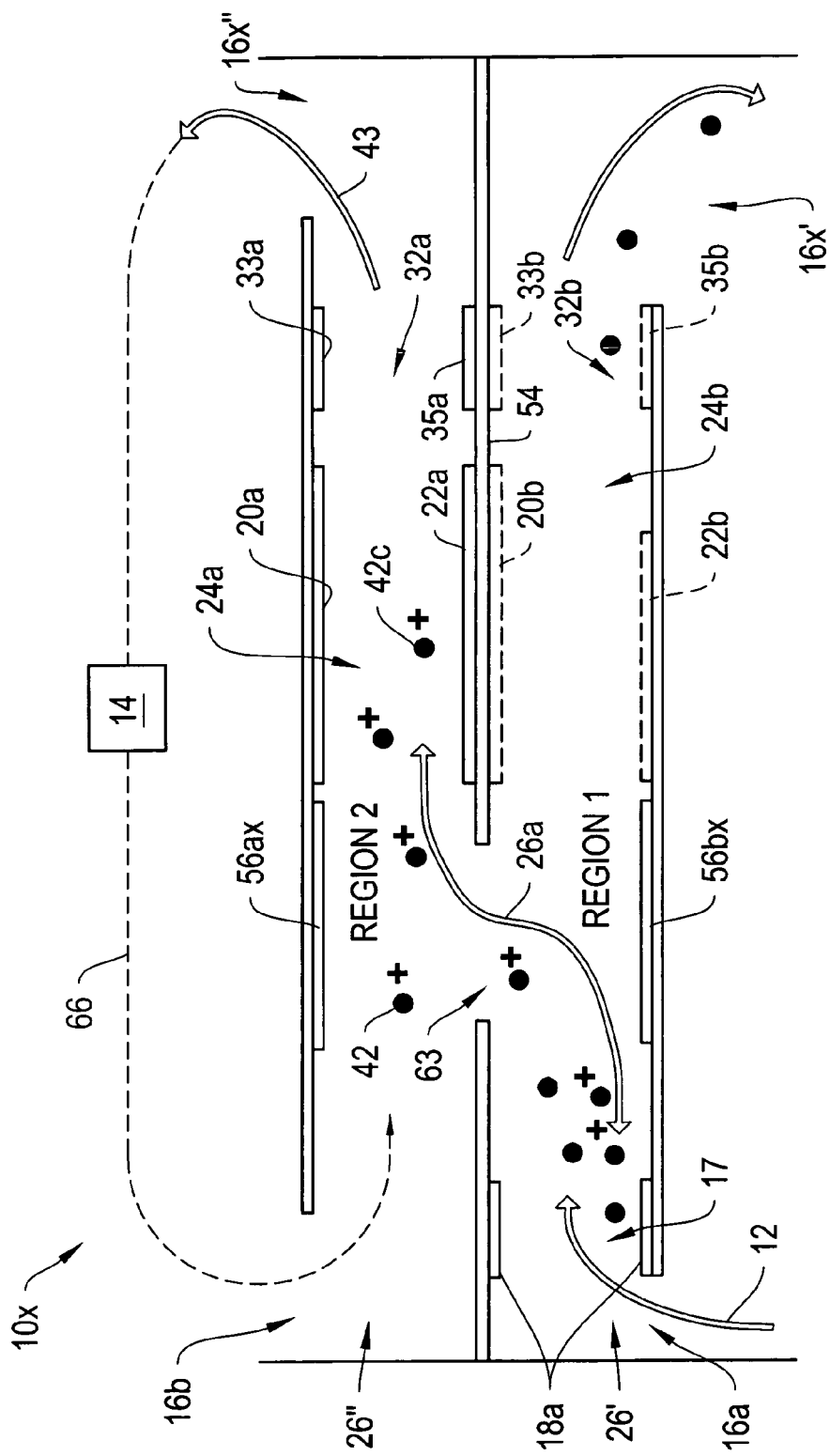
FIG. 8 is a cross sectional view of a dual channel embodiment of the invention.

Dual chamber embodiment 10x of the invention, FIG. 8, has two enclosed flow paths 26', 26" coupled by passageway 63. The gas sample 12 enters inlet 16a and is ionized at ionization region 17 in the lower flow path 26', ionized by any ionization device, such as an internal plasma source 18a. The ions are guided toward ion filter 24a in upper flow path 26" through passageway 63 by electrodes 56ax and 56bx, which act as steering or deflecting electrodes, and may be defined by confining electrodes 56a, 56b. As these ions 42c pass between ion filter electrodes 20a and 22a, undesirable ions will be neutralized by hitting the filter electrodes while selected ions will pass through filter 24a to be detected by detector 32a, according to the applied RF and compensation. By deflecting ions out of the gas flow, a preliminary filtration is effected, wherein the non-deflected ions and non-ionized sample and associated carrier gas will be exhausted at outlet 16x'. The exhaust gas 43 from upper flow path 26", at outlet 16x", may be cleaned, filtered and pumped via pump part 14a and returned at inlet 16b as clean filtered gas 66 back into the flow path 26".

In one practice of the invention, clean dry air 66a may be introduced into flow path 26 through clean air inlet 66 via pump 14. Drawing in clean dry air assists in reducing the ion mobility based analyzer's sensitivity to humidity. Moreover, if the spectrometer is operated alternately with and without clean dry air, and with a known gas sample introduced into the device, then the device can be used as a humidity sensor since the resulting spectrum will change with moisture concentration from the standardized spectrum for the given known sample.

In operation of the embodiment of FIG. 8, independent control of the flow rates in flow paths 26', 26" may be made. This means that a higher or lower flow rate in flow path 26' of the sample can be used, depending on the particular front end environment system, while the flow rate of the ions through the ion filter in flow path 26" can be maintained constant, allowing, consistent, reproducible results.

In practice of this embodiment, the upper ion filter region in flow path 26" can be kept free of neutrals. This is important when measuring samples at high concentrations, such as those eluting from a GC column. Because the amount of ions the ionization source can provide is fixed, if there are too many sample molecules, some of the neutral sample molecules may cluster with the sample ions and create large molecules which do not look at all like the individual sample molecules. By injecting the ions into the clean gas flow in flow path 26", and due to the effect of the high voltage high frequency field, the molecules will de-cluster, and the ions will produce the expected spectra.

Another advantage of the embodiment of FIG. 8 is that the dynamic range of the PFAIMS detector can be extended when employing a front end device (such as a GC, LC or electrospray for example). In one practice of the invention, by adjusting the ratios of the drift gas and GC-sample/carrier gas volume flow rates coming into ionization region 17, the concentration of the compounds eluting from the GC can be controlled/diluted in a known manner so that samples are delivered to the ion mobility based analyzer ion filter 24 at concentrations which are optimized for the ion mobility based analyzer filter and detector to handle. In addition, steering electrodes 56ax, 56bx can be pulsed or otherwise controlled to determine how many ions at a given time enter into flow path 26".

In a further practice of the embodiment of FIG. 8, an additional ion mobility based analyzer filter 24b may be provided in lower flow path 26' for detection of ion species that have not been deflected into flow path 26" and thus that pass into filter 24b. Filter 24b includes electrodes 20b, 22b, shown in phantom, and possibly also detector 32b having electrodes 33b, 35b, in phantom.

In the embodiment of FIG. 8, different gas conditions may be presented in each flow path. With a suitable control applied to the two steering electrodes 56ax, 56bx, selection can be made as to which region the ions are sent. Because each chamber can have its own gas and bias condition, multiple sets of data can be generated for a single sample simultaneously. This enables improved species discrimination in a simple structure, regardless of whether or not a front end device (such as a GC) is used for sample introduction.

Figure 9:
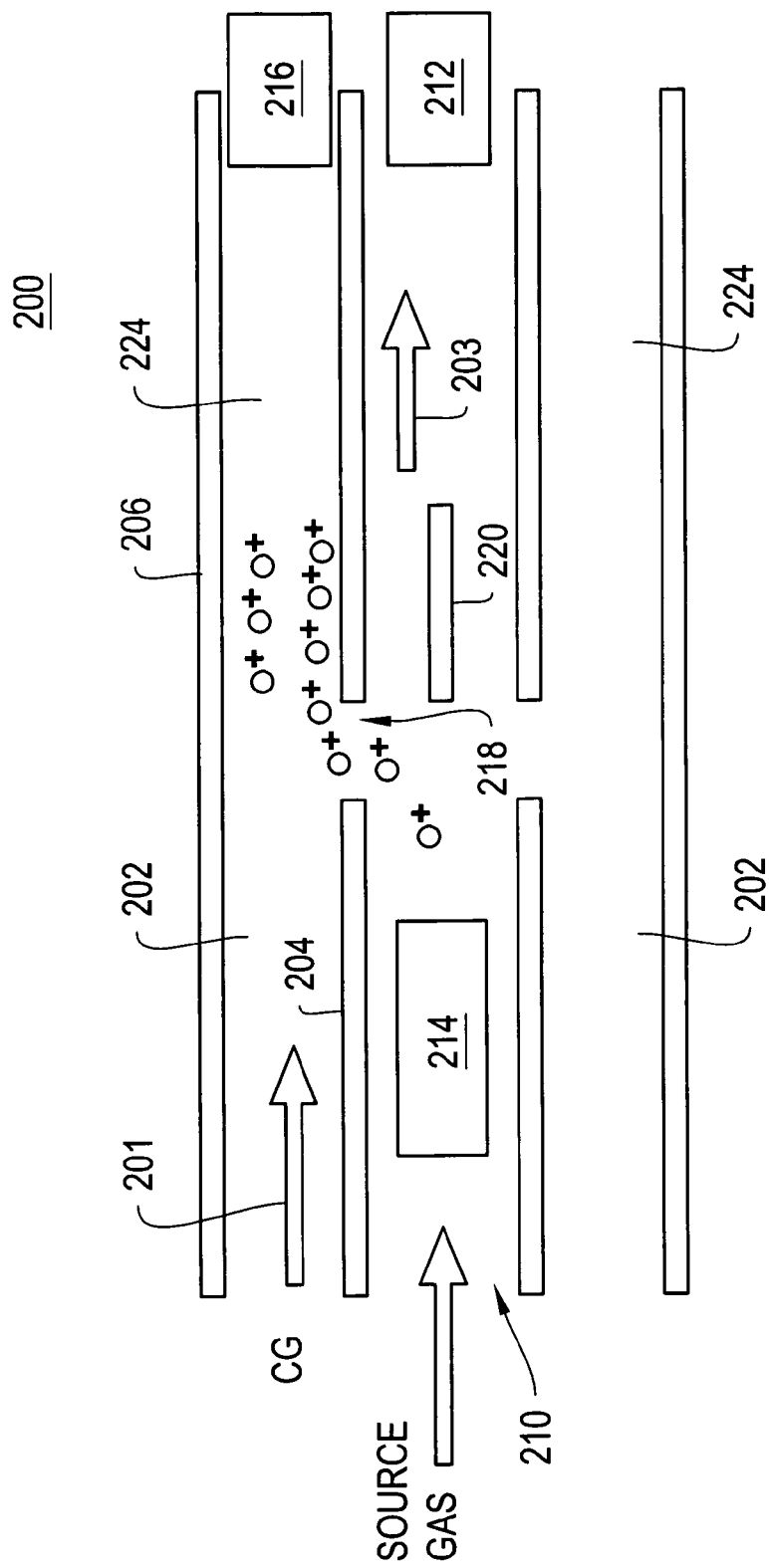
FIG. 9 is a schematic view of a prior art spectrometer.

One prior art ion mobility spectrometer 200, FIG. 9, (See U.S. Pat. No. 5,420,424), includes analytical gap 202 defined by the space between inner cylindrical filter electrode 204 and outer cylindrical filter electrode 206 electrodes. A source gas having compounds to be analyzed is drawn through inlet 210 via the action of pump 212; the sample is ionized by ionization source 214. A carrier gas CG is introduced via pump 216 into analytical gap 202. Ions generated by ionization source 214 travel through aperture 218 by the action of electrode 220 and into analytical gap 202 and travel toward detector 224. Such a structure requires two pumps 212 and 216, and separate flow paths 201 and 203 for the source gas and the carrier gas. Thus, prior art mobility spectrometer 200 cannot be made very small, and requires sufficient power to operate the pumps 212 and 216.

Embodiments of the present invention overcome limitations of the prior art by providing field-driven ion transport via an ion flow generator, where ions flow through an ion filter as carried by the ion transport field. The ion flow generator of the present invention relieves the gas flow requirements of the prior art. Various options are possible, including providing a low volume flow, no gas flow, or reverse gas flow, along the longitudinal axis of the flow path. The reverse flow can be a supply of clean filtered air in the negative z direction to keep the ion filter and detector regions free of neutrals and to help remove solvent, reduce clustering, and minimize the effects of humidity. The ion flow generator is preferably based on electric potentials, but may be practiced in magnetic embodiments, among others, and still remain within the spirit and scope of the present invention. Various embodiments follow by way of illustration and not by way of limitation.

Figure 10:
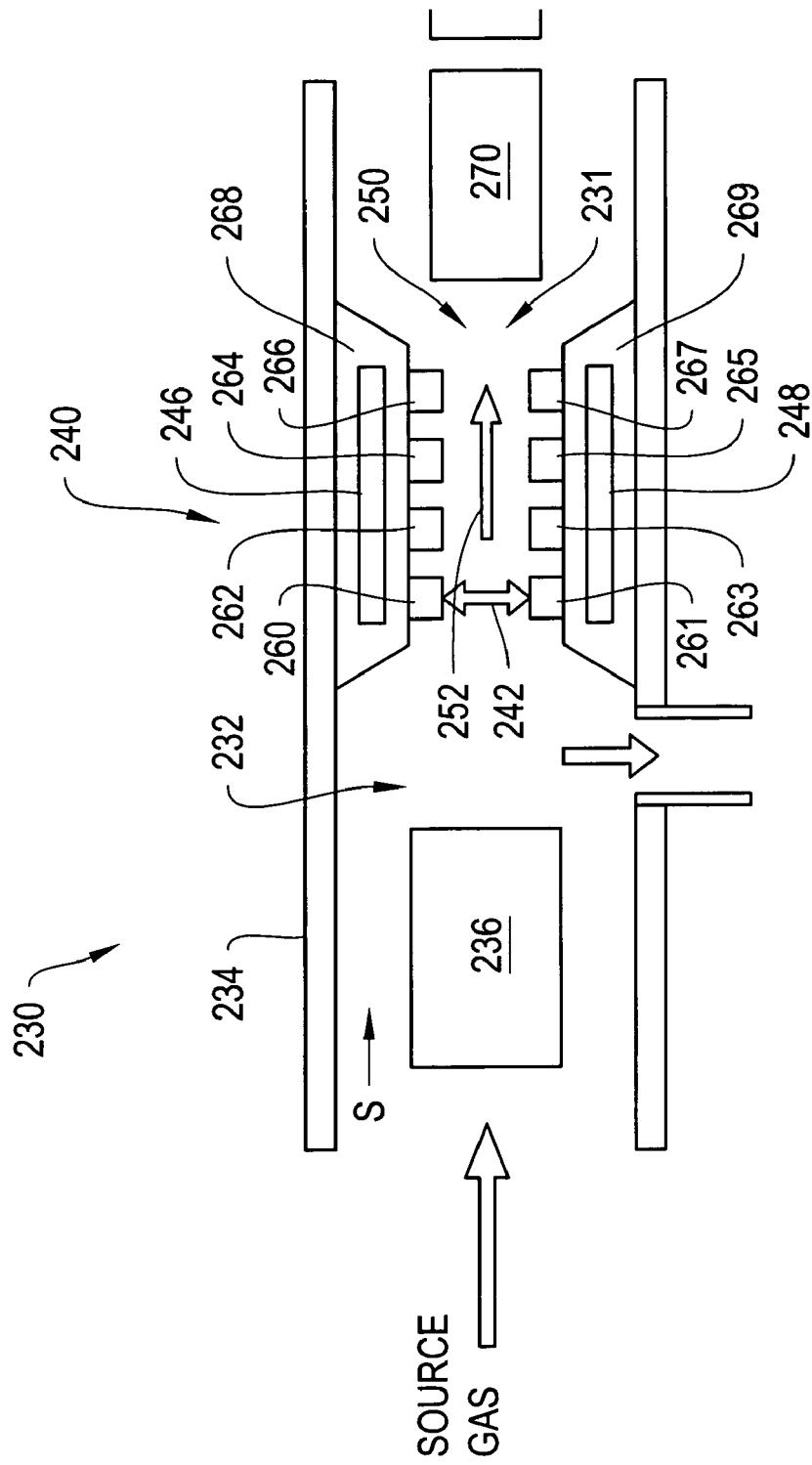
FIGS. 10-17 are respective schematic views of embodiments of the longitudinal field driven ion mobility spectrometer of the present invention.

In one practice of the invention, shown in FIG. 10, field asymmetric ion mobility spectrometer 230 includes a flow path 231 inside housing structure 234 (which may be formed by a round tube or a flat housing with walls defining an enclosure). A source gas carries sample S into the ionization region near the ionization source 236. This flow is supplied by pump 238, which may be a micromachined pump with a flow rate of much less than the typically required 1-4 liters per minute of the prior art (resulting in a power savings of between 1-5 watts over prior art spectrometers). Alternatively, this flow might be supplied by sample eluting from a GC column or the like.

Ion filter 240 is disposed in flow path 231 downstream from ionization source 236. Ion filter 240 creates the asymmetric electric field 242 (a compensated field 25), to filter ions generated by ionization of sample S. Ion filter 240 may include a pair of spaced electrodes 248 and 246 connected to an electric controller which applies a compensated asymmetric periodic voltage to electrodes 246 and 248.

In spectrometer 230, ion flow generator 250 provides longitudinal electric field transport for the ions. The strength of longitudinal electric field 252 can be constant or varying in time or space; the field propels ions through the filter asymmetric field 242, with ions passing through the filter according to their characteristics and the filter field compensation.

In the embodiment of FIG. 10, ion flow generator 250 includes discrete electrodes 260, 262, 264, and 266 supported by and insulated from filter electrode 246 by insulating medium 268, and discrete electrodes 261, 263, 265, and 267 supported by and insulated from filter electrode 248 by insulating medium 269. In one practice of the invention, electrodes 260, 261 are at 1,000 volts and electrodes 266, 267 are at 10 volts and electrode pairs 262, 263 and 264, 265 are at 500 and 100 volts, respectively, although these voltage levels vary or be varying depending on the specific implementation of spectrometer 230. There may be more or fewer electrodes opposing each other forming ion flow generator 250. Electrode pairs (260, 261), (262, 263), (264, 265), and (266, 267) can also each be a ring electrode as well as discrete planar electrodes. The strength of longitudinal electric field 252 propels ions generated at ionization source 236 through asymmetric electric field 242 and toward detector 270, thus eliminating or reducing the flow rate and power requirements of pumps 212 and 216, FIG. 9 of the prior art.

Typically, detector 270 (which may have the configuration shown earlier of two electrodes 33, 35 on substrates 52, 54) is positioned close to ion flow generator 250. Electrodes 260, 262, 264, 266, 261, 263, 265, and 267 preferably occupy more or less the same longitudinal space as ion filter 240 and its electrodes 246 and 248 relative to a gap 232 in flow path 231.

Figure 11:
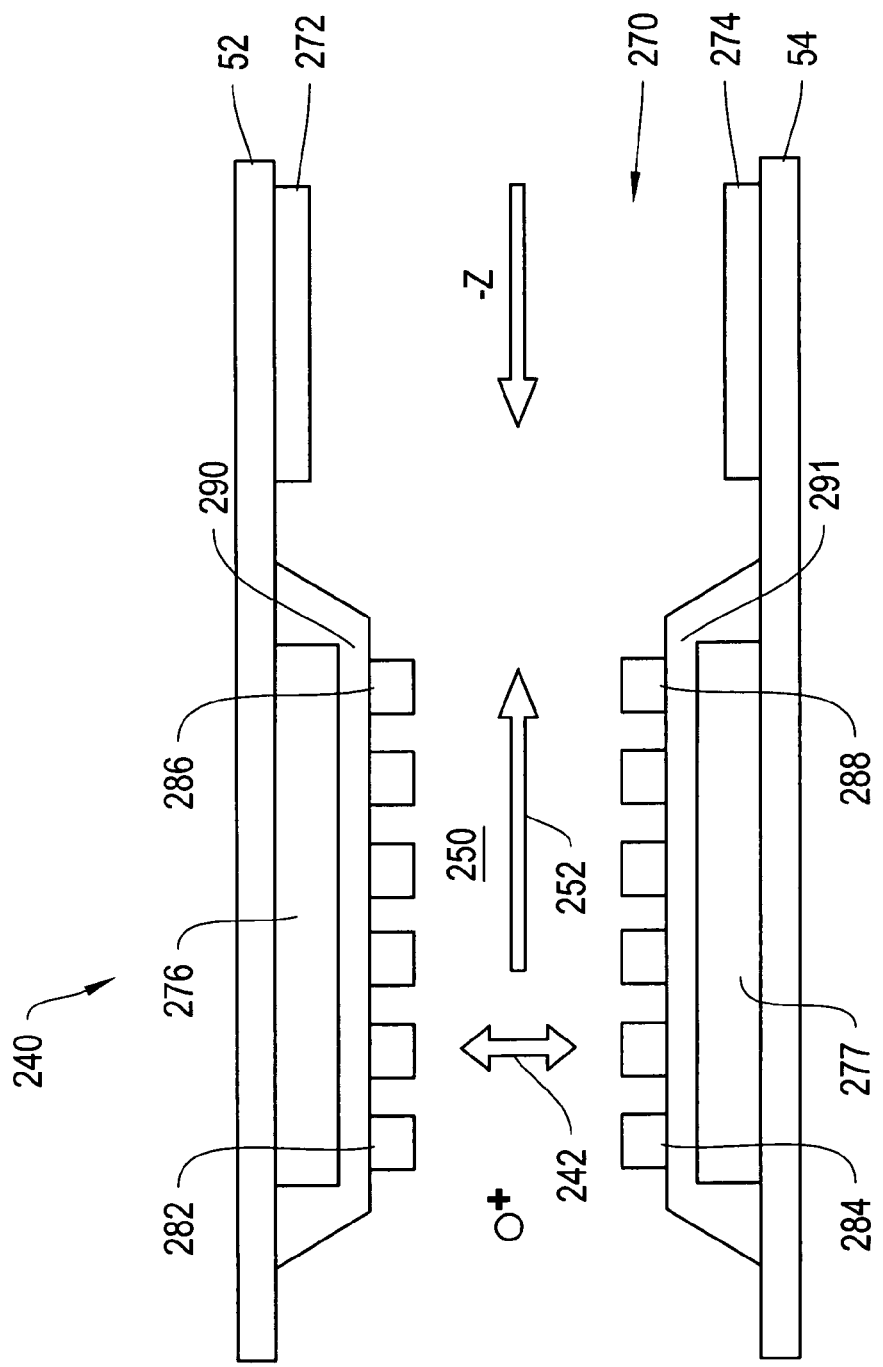

In the embodiment of the invention shown in FIG. 11, ion filter 240 includes spaced electrodes 276 and 277 for creating transverse filter field 242. The ion flow generator 250 includes spaced discrete electrodes, such as electrode pairs 282-284 and 286-288, for generating longitudinal transport field 252. In one practice, electrodes 282 and 284 are at 0 volts and electrodes 286 and 288 are at 1000 volts. Insulating medium 290 and 291 insulates electrodes 282, 284, 286, and 288 with respect to electrodes 276 and 277. Electrode pair 282-284 could also be coupled as a single ring electrode and electrode pair 286-288 could be coupled also be a single ring electrode in a cylindrical embodiment of the invention.

It will be appreciated that the sample must be conveyed to the ionization region and the ions must be conveyed into the filter. In the design of FIG. 11, the ions are propelled by a low volume flow along the direction of the longitudinal electric field 252 to bring the ions proximate to electrodes 282-284. No gas flow is required in the ion filter and detector region due to longitudinal electric field 252. Also in this embodiment, a low flow volume of clean filtered air optionally can be provided in a direction opposite the longitudinal electric field to keep the ion filter and detector region free of neutrals. A resistive divider circuit or the like can be used to provide a potential gradient, so that for example, electrodes 282 and 284 are at 1000 volts while electrodes 286 and 288 are at 0 volts.

Figure 12:
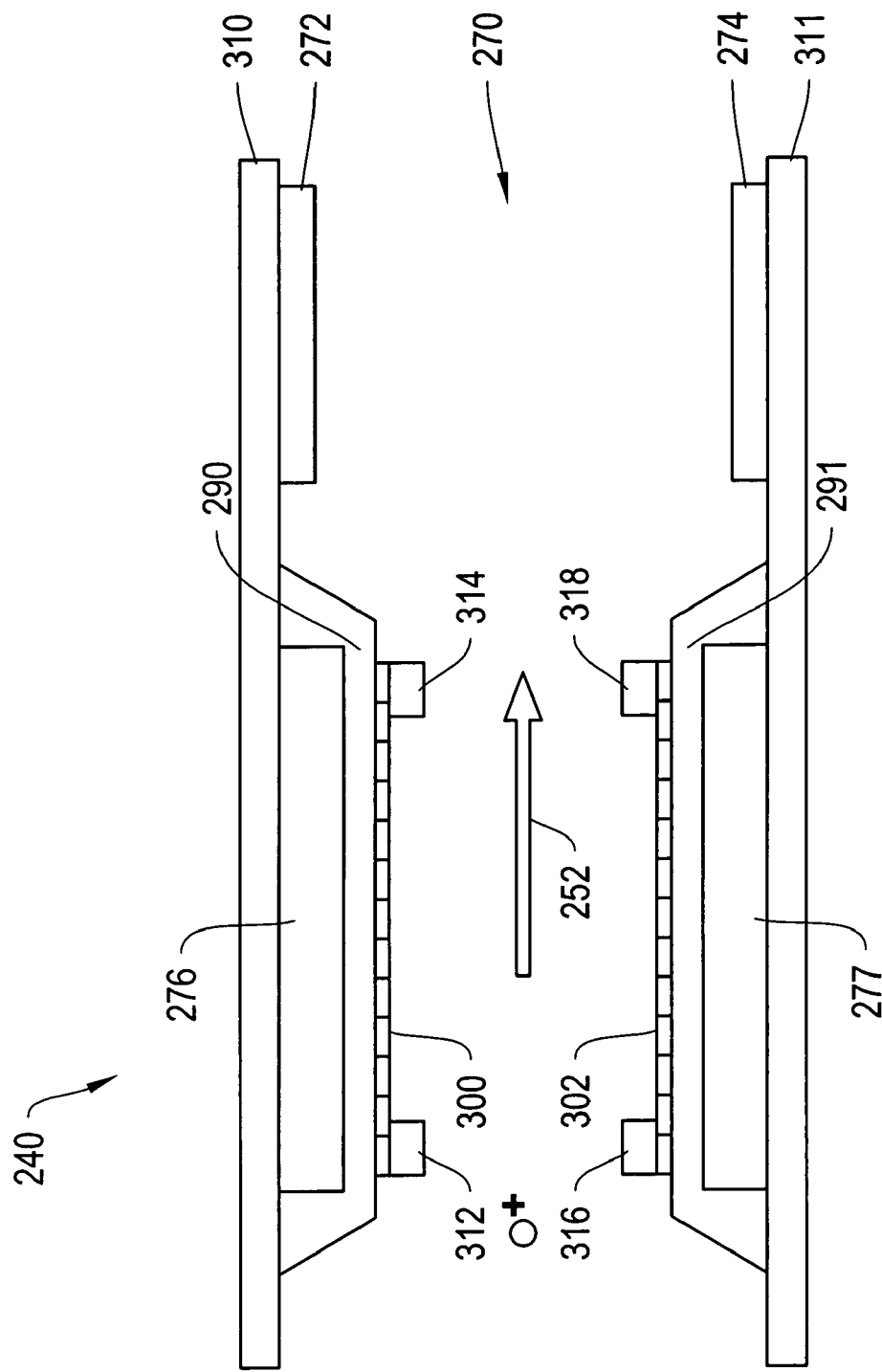

An alternative practice of the invention is shown in FIG. 12, having metal filter electrodes 276, 277 deposited on insulating substrates 310, 311 and filter electrodes 276, 277 coated with a thin insulator 290, 291. Metal electrodes, e.g., 312, 314, 316, 318, are formed under a resistive layer 300, 302, and the longitudinal field is generated between these electrodes. In one practice, ion filter 240 includes spaced resistive layers 300 and 302 insulated from electrodes 276 and 277 on insulating substrates 310, 311 by insulating medium 290 and 291, for example, a low temperature oxide material. Resistive layers 300 and 302 may be a resistive ceramic material deposited on insulating layers 290 and 291, respectively. Terminal electrodes 312, 314, 316 and 318 make contact with each resistive layer to enable a voltage drop across each resistive layer that generates the longitudinal electric field 252, for example, where electrodes 312 and 316 are at 1000 volts while electrodes 314 and 318 are at 0 volts. This embodiment can be extended to a cylindrical geometry by making electrodes 312 and 316 a ring electrode, electrodes 314 and 318 a ring electrode, and resistive layers 300 and 302 an open cylinder.

Figure 13:
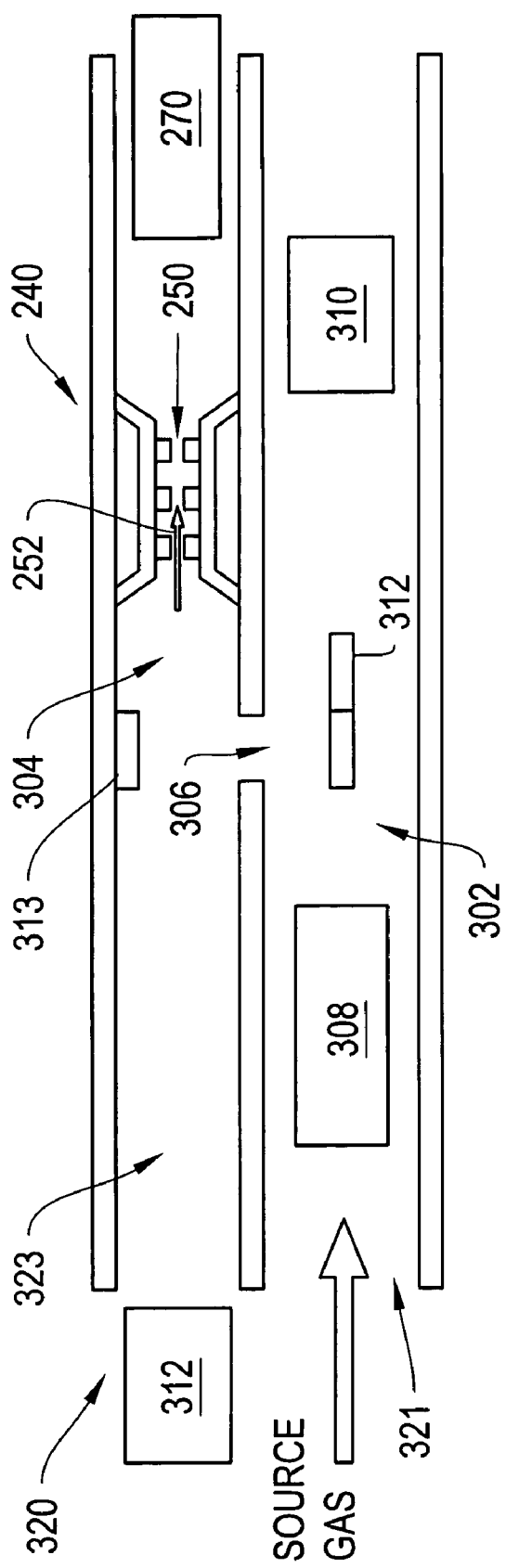

Continuing with the benefits of a dual flow path, such as earlier shown in FIG. 8, in the embodiment of FIG. 13 spectrometer 320 includes structure which also defines dual flow paths 321, 323. Ion filter 240 and ion flow generator 250 are defined by sets of electrodes in this embodiment. Gap 304 is defined in flow path 323 at filter 240. Opening 306 joins the flow paths. Source gas carrying sample S to be analyzed is drawn into flow path 302 by pump 310 and ionized by ionization source 308. The ions are deflected through opening 306 and into gap 304 assisted by deflecting electrodes 312 and 313. Ion flow generator 250 propels the ions through the asymmetric ion field at filter 240. Optionally pump 312 can be used to supply a low flow rate of air, possibly dehumidified, into, or recirculating through, gap 304, but no carrier gas flow is required in flow path 302. Ion species passed by the filter are carried by the ion transport 252 to detector 270.

Figure 14:
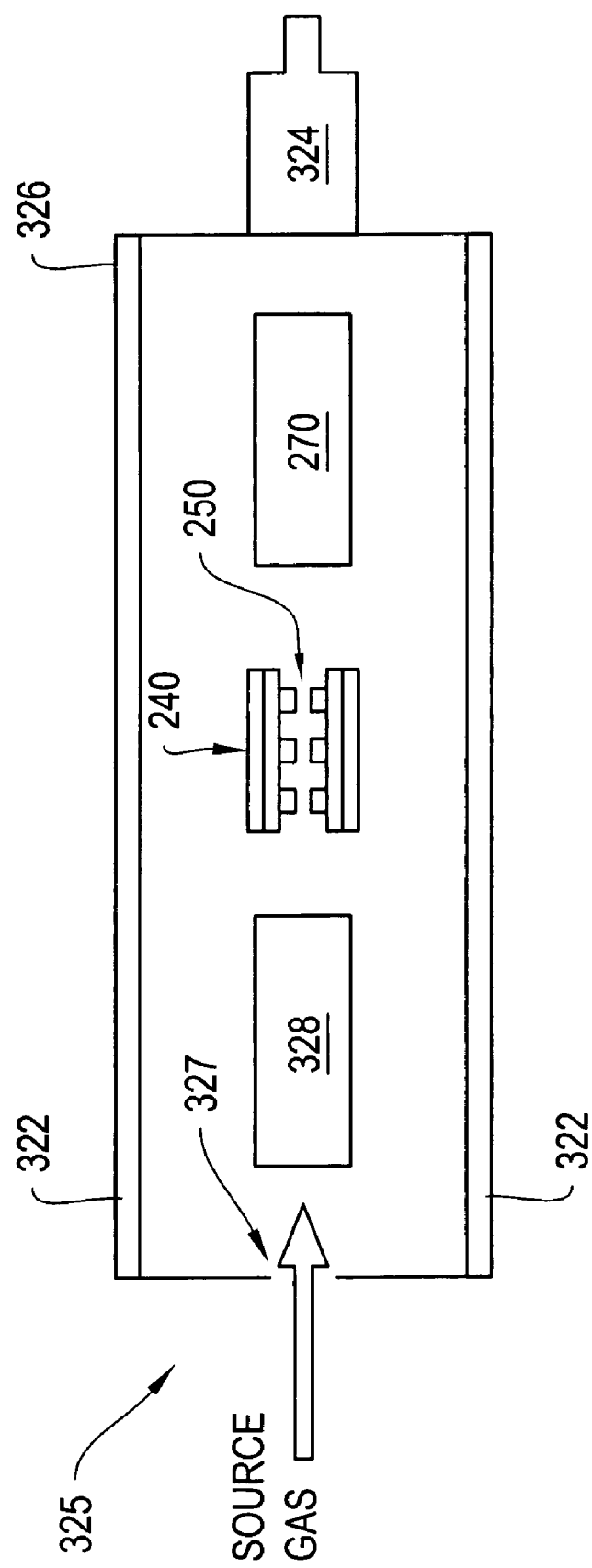

In another embodiment of the invention, shown in FIG. 14, spectrometer 325 includes a desiccant 322 chambered in housing 326 and small pump 324, which is the only pump required to draw source gas into housing 326 through a small orifice 327. Ionization source 328 produces ions which travel through filter 240 aided by the longitudinal electric field created by ion flow generator 250. The desiccant serves to further condition the sample gas before filtering for improved performance.

Figure 15:
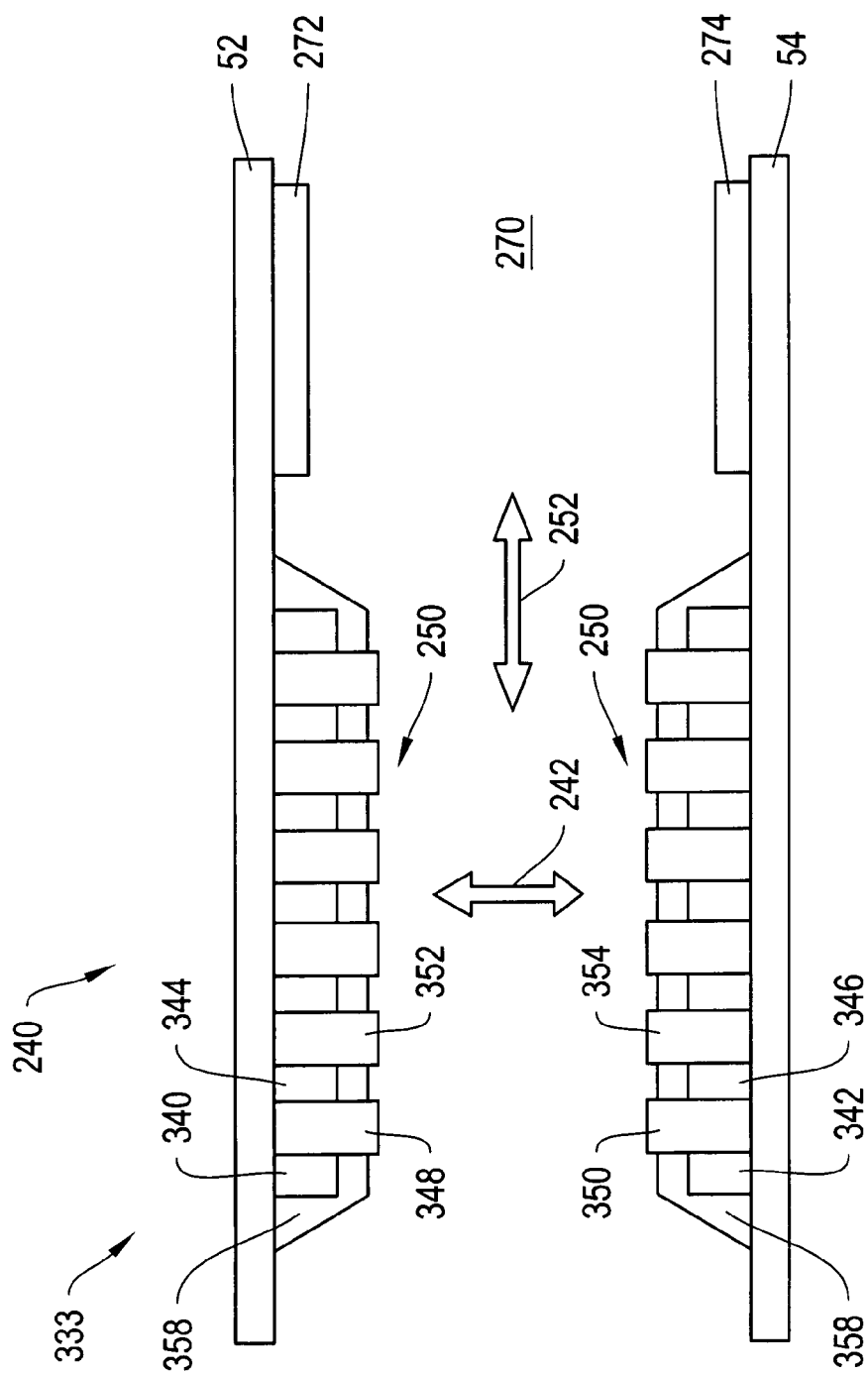

In still another embodiment shown in FIG. 15, spectrometer 333 includes ion filter 240 with a plurality of RF electrodes 340, 342, 344 and 346 connected to an electric controller 30 which applies the asymmetric periodic voltage to create the filtering field. DC compensation may also be applied to these electrodes. The ion flow generator 250 includes a second plurality of discrete electrodes 348, 350, 352 and 354 dispersed among but insulated from the discrete RF electrodes of the ion filter and connected to controller 30, which establishes a gradient between the electrodes to generate an ion propelling transport field 252 along the flow path toward the detector 270. The electrodes may be coated with an insulating material 358, as well as being isolated from each other by adequate insulation.

In the embodiment of FIG. 15, all the RF electrodes may be independently driven or tied together while the longitudinal field producing electrodes have a potential gradient dropped across them. In one embodiment, the voltages applied to the electrodes can be alternated so that first a voltage is applied to generate the transverse RF electric field 242 and then a voltage is applied to other or same electrodes to generate the longitudinal ion transport field 252.

Figure 16:
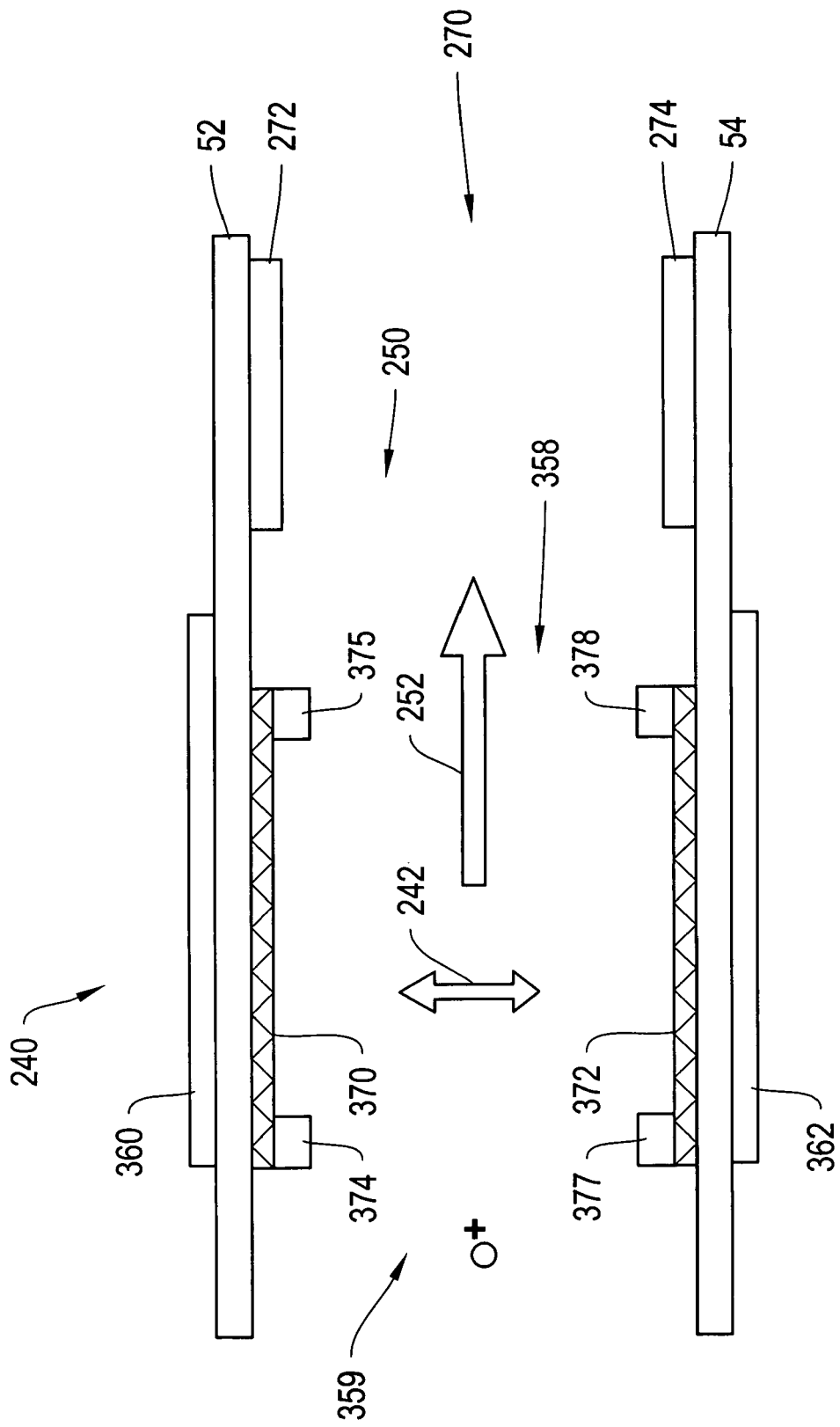

In still another embodiment, spectrometer embodiment 359 shown in FIG. 16 includes RF electrodes 360, 362, which provide the asymmetric ion filtering electric field 252 are disposed on the outside walls of insulative substrates 52, 54. Resistive layers 370 and 372 may be a resistive ceramic material deposited on the inside walls of insulating substrates 52 and 54, respectively. Terminal electrodes 374-375, and 377-378 make contact with each resistive layer is shown to enable a voltage drop across each resistive layer to generate the ion propelling longitudinal electric field 252. Thus, electrodes 374 and 377 may each be at −100 volts while electrodes 375 and 378 are at −1000 volts, for example.

Figure 17:
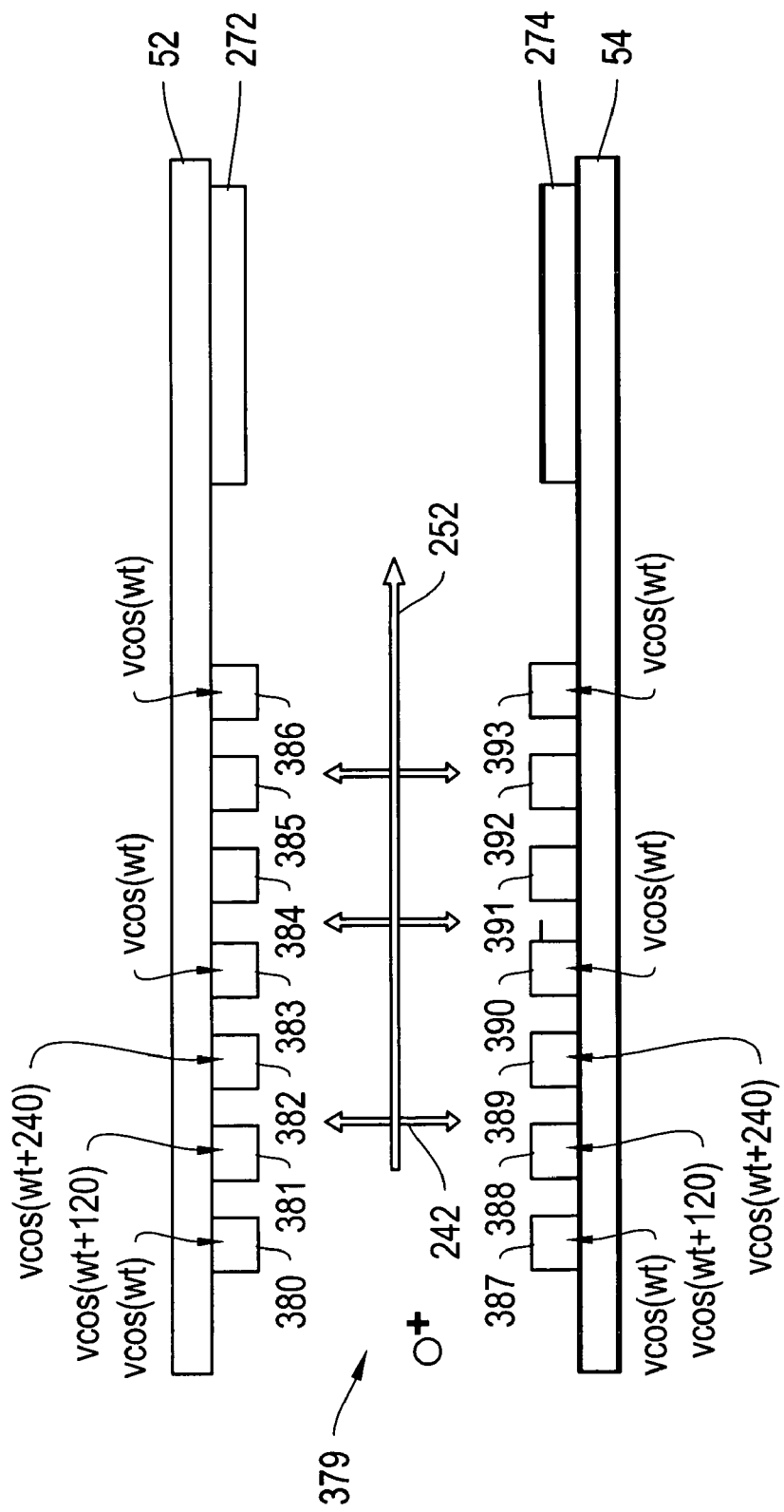

In the embodiment of FIG. 17, spectrometer 379 has discrete electrodes 380-386 on substrate 52 and 387-394 on substrate 54 which cooperate to produce an electrical field or fields. The net effect provides both transverse and longitudinal field components to both filter and propel the ions. A traveling wave voltage of the form $$V \cos(wt - kz)$$

where $k = 2\pi/\lambda$ is the wave number has an associated electric field with both transverse and longitudinal components 242+ 252. For a planar system and/or planar ion mobility based analyzer, each succeeding set of opposing electrodes is excited by a voltage source at a fixed phase difference from the voltage source applied to the adjacent set of opposing electrodes.

Thus, electrodes 380 and 387 are excited with a voltage of v cos(wt) while electrodes 381 and 388 are excited with a voltage of v cos (wt+120) and so on as shown in FIG. 17. Traveling wave voltages require multiphase voltage excitations, the simplest being a two phase excitation. So, a two conductor ribbon could also be wound around a duct defining the gap with one conductor excited at v cos (wt) and the other conductor excited at v sin (wt). Three phase excitations could be incorporated if the conductor ribbon or tape had three conductors.

In an alternative of the embodiment of FIG. 17, the discrete electrodes 380-386 and 387-394 are still driven to produce both transverse and longitudinal fields to both filter and propel the ions. The ion mobility based analyzer RF signal is applied to the electrodes to generate the transverse RF field, which may involve one electrode on each substrate or multiple electrodes. Compensation is also generated, either by varying the duty cycle or the like of the RF, or by applying a DC bias to the electrodes, which may involve one electrode on each substrate or multiple electrodes. Finally, the ion flow generator includes a selection of these electrodes biased to different voltage levels (e.g., 1000 vdc on electrodes 380 and 387 and 100 vdc on electrodes 386 and 393) to generate a gradient along the flow path. Compensation voltage applied to the RF filter field opens the filter to passage of a desired ion species if present in the sample as propelled by the flow generator. If the compensation voltage is scanned, then a complete spectrum of the compounds in a sample can be gathered.

Figure 18:
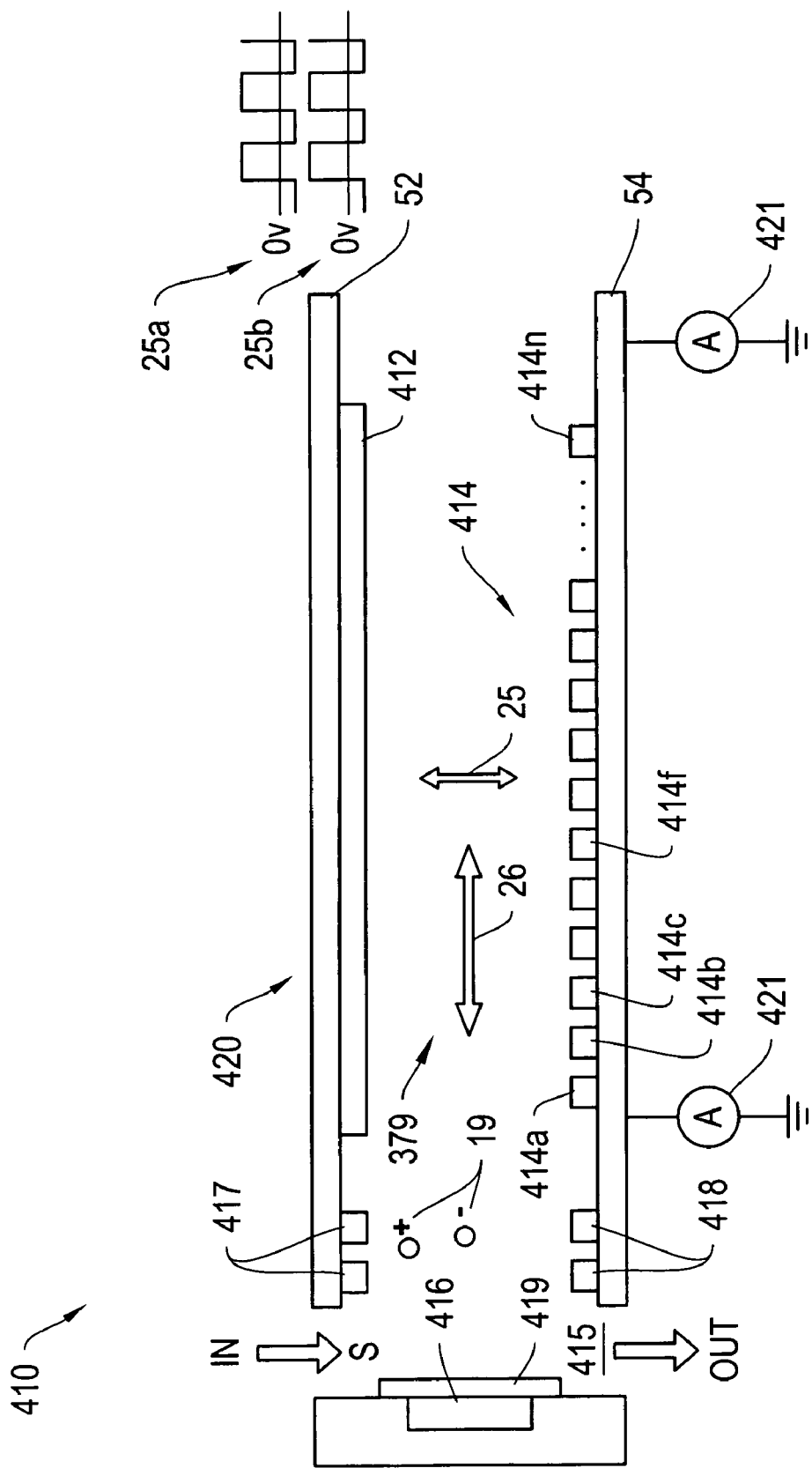
FIG. 18 is an embodiment of the invention that performs ion filtering based on ion trajectory within the filter region.

In a further embodiment of the invention, ion filtering is achieved without the need for compensation of the filter field. As shown in FIG. 18, in one illustrative embodiment, spectrometer 410 has a single RF (high frequency, high voltage) filter electrode 412 on substrate 52. A segmented filter-detector electrode set 414 on substrate 54 has a plurality of electrodes 414a-414n. Electrode 412 faces set 414 over flow path 26. Strips 414a-414n are maintained at virtual ground, while the asymmetric field signal is applied to the filter electrode 412.

It will be further appreciated that, referring to FIG. 2, ions 19 flow in the alternating asymmetric electric field 25 and travel in oscillating paths that are vectored toward collision with a filter electrode, and collision will occur in absence of adequate compensation. In the embodiment of FIG. 18, the absence of compensation favorably enables driving of the ions to various electrodes of the segmented electrode set 414. Thus all of the ions are allowed to reach and contact one of the electrodes 414a-414n. These ions thus deposit their charges upon such contact, which is monitored such as with current meters 421, 421. (It will be further appreciated that this arrangement is illustrative and not limiting. For example, the filter electrode may be segmented, similar to the filter-detector electrode set, where ions also will be detected thereon.)

In an illustrative embodiment, upstream biasing effects which ions flow to the filter. For example, a sample S flows ("IN") into an ionization region 415 subject to ionization source 416. Electrodes 417, 418, 419 are biased to deflect and effect flow of the resulting ions. Positive bias on electrode 419 repels positive ions toward the filter and electrodes 417, 418 being negatively biased attract the positive ions into the central flow of filter 420, while negative ions are neutralized on electrode 419 and which are then swept out ("OUT") of the region. Negative bias on electrode 419 repels negative ions toward the filter and electrodes 417, 418 being positively biased attract the negative ions into the central flow path 26 of filter 420, while positive ions are neutralized on electrode 419.

The path taken by a particular ion in the filter is mostly a function of ion size, cross-section and charge, which will determine which of the electrodes 414a-414n a particular species will drive into. This species identification also reflects the polarity of the ions and the high/low field mobility differences ("alpha") of those ions. Thus a particular ion species can be identified based on its trajectory (i.e., which electrode is hit) and knowledge of the signals applied, the fields generated, and the transport characteristics (such as whether gas or electric field).

In practice of the filter function, where the upstream biasing admits positive ions 19+ into the filter, those positive ions with an alpha less than zero will have a mobility decrease with an increase of the positively offset applied RF field (waveform 25a). This will effect the trajectory of these ions toward downstream detector electrode 414n. However, a positive ion 19+ with an alpha greater than zero will have a mobility increase with an increase of the negatively offset applied RF field (waveform 25b), which in turn will shorten the ion trajectory toward the nearer detector electrodes.

Similarly, where the filter is biased to admit negative ions, a negative ion 19− with an alpha less than zero will have a mobility increase with an increase of the positively offset applied RF field waveform 25a; this will tend to effect the ion trajectory toward downstream detector electrode 414n. However, a negative ion 19− with an alpha greater than zero will have a mobility increase with an increase of the negatively offset applied RF field waveform 25b, which in turn will tend to shorten the ion trajectory toward the nearer detector electrodes. Thus, ions can be both filtered and detected in spectrometer 410 without the need for compensation.

Figure 19:
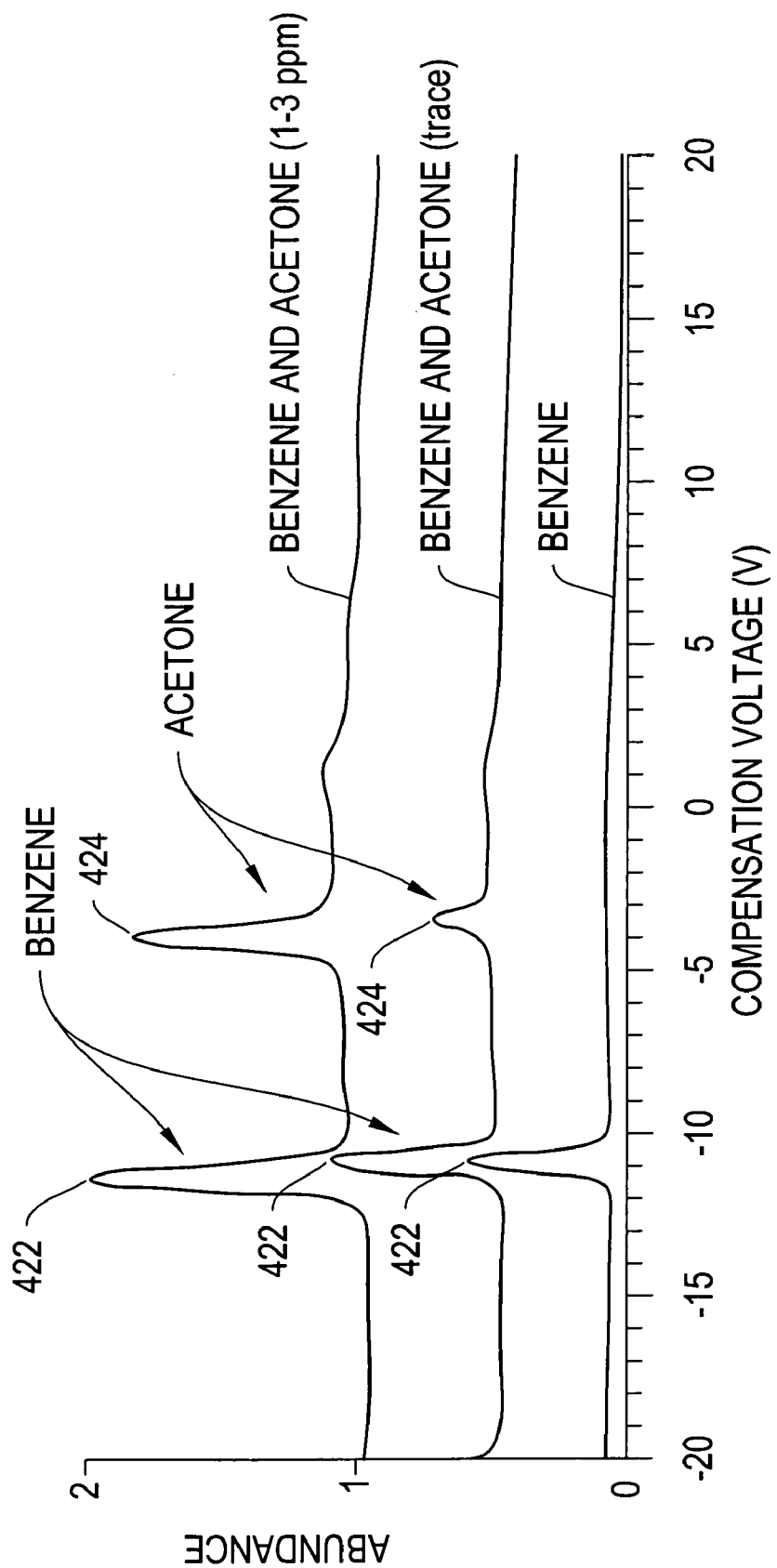
FIG. 19 is a graphical representation of identification of chemical constituents of a mixture (benzene and acetone) in practice of the invention.

Various embodiments of the present invention are able to identify compounds in a chemical sample down to trace amounts. In FIG. 19, identification of individual constituents of a mixture is demonstrated by the distinct and separate Benzene peaks 422 and acetone peaks 424 obtained in practice of the invention. Three plots are superimposed in FIG. 19. The first plot is for benzene and acetone (1-3) ppm; the second plot is for benzene and acetone (trace). The bottom plot shows benzene alone. It therefore can be observed that the acetone peak can be easily distinguished from the benzene peak in practice of the present invention. This capability enables separation and identification of a wide array of compounds in chemical samples in a compact and cost-effective method and apparatus of the invention.

Multiple use of electrodes is not limited to the examples set forth above. Embodiments of the present invention lend themselves to the use of an electrospray ionization source nozzle because certain of the electrodes can function both as the source for the ion mobility based analyzer and longitudinal electrical field which transports the ions toward the detector electrodes, but also as the electrospray electrodes which create a fine spray sample for ionization. Thus, in accordance with the present invention, pumps 216 and 212, FIG. 9 of the prior art are either eliminated or at least reduced in size and have lower flow rate and power requirements.

In practice of the invention, by the incorporation of an ion flow generator which creates a longitudinal electric field in the direction of the intended ion travel, the ions are propelled through the transversely directed compensated asymmetric electric field and onward for detection. The apparatus may include a detector or may deliver ions to a detector.

In practice of the invention, pump and gas flow requirements are simplified. By eliminating the high flow rate of pumps used in prior art spectrometers, a significant reduction in power consumption, size, and cost can be realized leading to a miniaturized spectrometer on a chip in practice of embodiments of the invention.

Another benefit in practice of alternative embodiments of the invention is that a flow of clean filtered air can be applied in a direction opposite the direction of the motion of the ions. In this way, any neutrals in the sample gas which were not ionized are deflected away and do not enter the ion analysis region. The result is the reduction or elimination of ion clustering, and reduction of the impact of humidity on sensor performance. Because the flow rates are low, it is possible to incorporate integrated micromachined components. Molecular sieves can be located close to the filter in order to absorb any neutral molecules in the analysis region to reduce or prevent clustering.

Embodiments of the present invention employ a field asymmetric ion mobility filtering technique that uses compensated high frequency high voltage waveforms and longitudinal e-field propulsion. The RF fields are applied perpendicular to ion transport, with a planar configuration, but coaxial, concentric, cylindrical and radial embodiments are also within the scope of the invention.

The spectrometer can be made extremely small, if required, and used in chemical and military applications, as a filter for a mass spectrometer, as a detector for a gas chromatograph, as a front end to a time of flight ion mobility spectrometer for increased resolution or as a filter for a flexural plate wave device.

The present invention provides improved chemical analysis. The present invention overcomes cost, size or performance limitations of MS, TOF-IMS, FAIMS, and other prior art devices, in novel method and apparatus for chemical species discrimination based on ion mobility in a compact, fieldable packaging. These devices have the further ability to render simultaneous detection of a broad range of species, and have the capability of simultaneous detection of both positive and negative ions in a gas sample. Still further surprising is that this can be achieved in a cost-effective, compact, volume-manufacturable package that can operate in the field with low power requirements and yet it is able to generate definitive data that can fully identify various detected species.

The present invention may be implemented using conventional or advanced manufacturing techniques, such as MEMS, micromachining, or nanotechnology based fabrication techniques. These techniques may include, for example, etching of smooth channels, chambers, dams, and intersections, and ports, forming and building upon substrates, etching and bonding, including anodic bonding and fusion, thin film processing and metallization applications, quartz machining, reactive ion etching, high temperature fusion bonding, photolithography, wet etching and the like.

Examples of applications for the present invention include chemical sensors and explosives sensors, and the like. Various modifications of the specific embodiments set forth above are also within the spirit and scope of the invention. For example, it will be further appreciated that embodiments of the invention may be practiced with coaxial, concentric, ring, cylindrical, radial or other features. For example, the electrodes of FIG. 17 may be ring electrodes; as well, structural variations may appear in combination, such as where the electrodes of FIG. 11 are ring electrodes and the remaining layers and electrodes are coaxial and cylindrical, for example.

Figure 20:
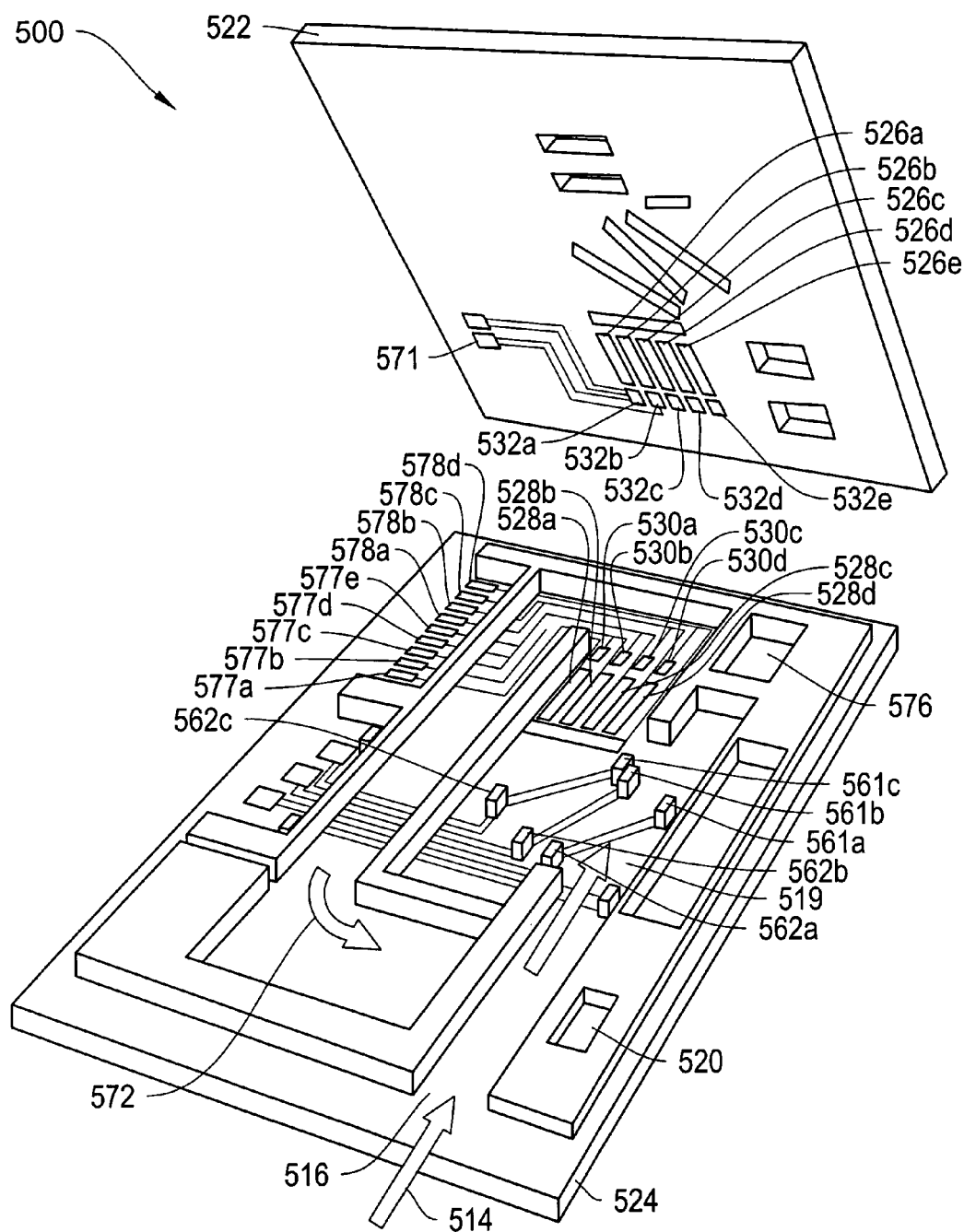
FIG. 20 includes schematic views of an electro-mechanical component layout, or integrated circuit like structure, for a compact GC-DMS analyzer using an array of filter and detector electrodes in a single flow path, according to an illustrative embodiment of the invention.

FIG. 20 includes an exploded perspective view of a mechanical layout for a compact DMS 500 according to an illustrative embodiment of the invention including a plurality of pairs of filter electrodes 526 and 528. In one embodiment, substantially the same components of FIG. 1 are employed, only in multiples, the multiples are indicated by the appended a, b, c, d, etc. Turning to FIG. 20, the DMS 500 includes a sample inlet 516 for receiving a sample 514, for example, from a GC column, another DMS analyzer, pre-filter, pre-concentrator, IMS, or other ion mobility based analyzer. The DMS 500 also includes an ionization source 520, such as a corona discharge source. The DMS 570 further includes a plurality of pairs of spacers 561a-562a, 561b-562b, 561c-562c, 561d-562d, and 561e-562e (not visible). In certain embodiments, the spacers 561a-561d and 562a-562d may be used to confine a plurality of flow channels, where each channel is associated with a particular filter electrode pair. They may also be electrodes, biased to deflect or otherwise steer or contain ions flowing in the flow channel.

The illustrative DMS 500 also includes a plurality of filter electrode pairs 526a-528a, 526b-526b, 526c-528c, 526d-528d, and 526e-528e. Each of the leads 577a-577e independently provides, for example, the compensation voltage Vcomp to a respective filter electrode pair 526-528. Each of the leads 578a-578e (578e not visible) independently provides, for example, the AC field voltage Vrf to a respective filter electrode pair 526-528. As shown, each filter electrode pair 526a-528a, 526b-526b, 526c-528c, 526d-528d, and 526e-528e has an associated detector electrode pair 530a-532a, 530b-532b, 530c-532c, 530d-532d, and 530d-532e (530e not visible). According to the illustrative embodiment of FIG. 20, and as indicated by the arrow 572, a single flow channel is provided to the filter electrode pairs 526a-528a, 526b-528b, 526c-528c, 526d-528d, and 526e-528e. However, the path between each filter electrode pair and its respective detector pair 530a-532a, 530b-532b, 530c-532c, 530d-532d, and 530d-532e (530e not visible) may be confined According to one illustrative embodiment, the filter electrode pairs 526a-528a, 526b-526b, 526c-528c, 526d-528d, and 526e-528e are caused to concurrently or substantially simultaneously pass different ion species according to the applied signals 577a-577e, 578a-578e, and 571. Thus, the detector pairs 530a-532a, 530b-532b, 530c-532c, 530d-532d, and 530d-532e (530e not visible) can concurrently or substantially simultaneously detect a plurality of ion species.

Alternatively, the control signals 577a-577e, 578a-578e, and 571 may be swept for each pair over a range of Vcomp and/or Vrf conditions to obtain a desired sample spectrum. Although FIG. 20 only shows two applied control signals 571 being connected to filter electrodes 526a-526e, the bias voltages Vcomp and/or Vrf for filter electrodes 526a-526e can be controlled independently by additional applied control signals. According to another feature, with an array of filter electrode pairs 526a-528a, 526b-528b, 526c-528c, 526d-528d, and 526e-528e, a complete spectral range of compensation voltages Vcomp can be more rapidly scanned than with a single filter. In an array configuration, each filter can also be used to scan over a smaller Vcomp and/or Vrf voltage range. The combination of all of these scans results in sweeping the desired full spectrum in a reduced time period. If there are three filters, for example, the spectrum can be divided into three portion and each is assigned to one of the filters, and all three can be measured simultaneously. In practice of the invention, filter array 528-530 may include any number of filter electrodes, depending on the size and use of the DMS 500. According to the illustrative embodiment of FIG. 20, the DMS 500 has a single common exit port 576.

Figure 21:
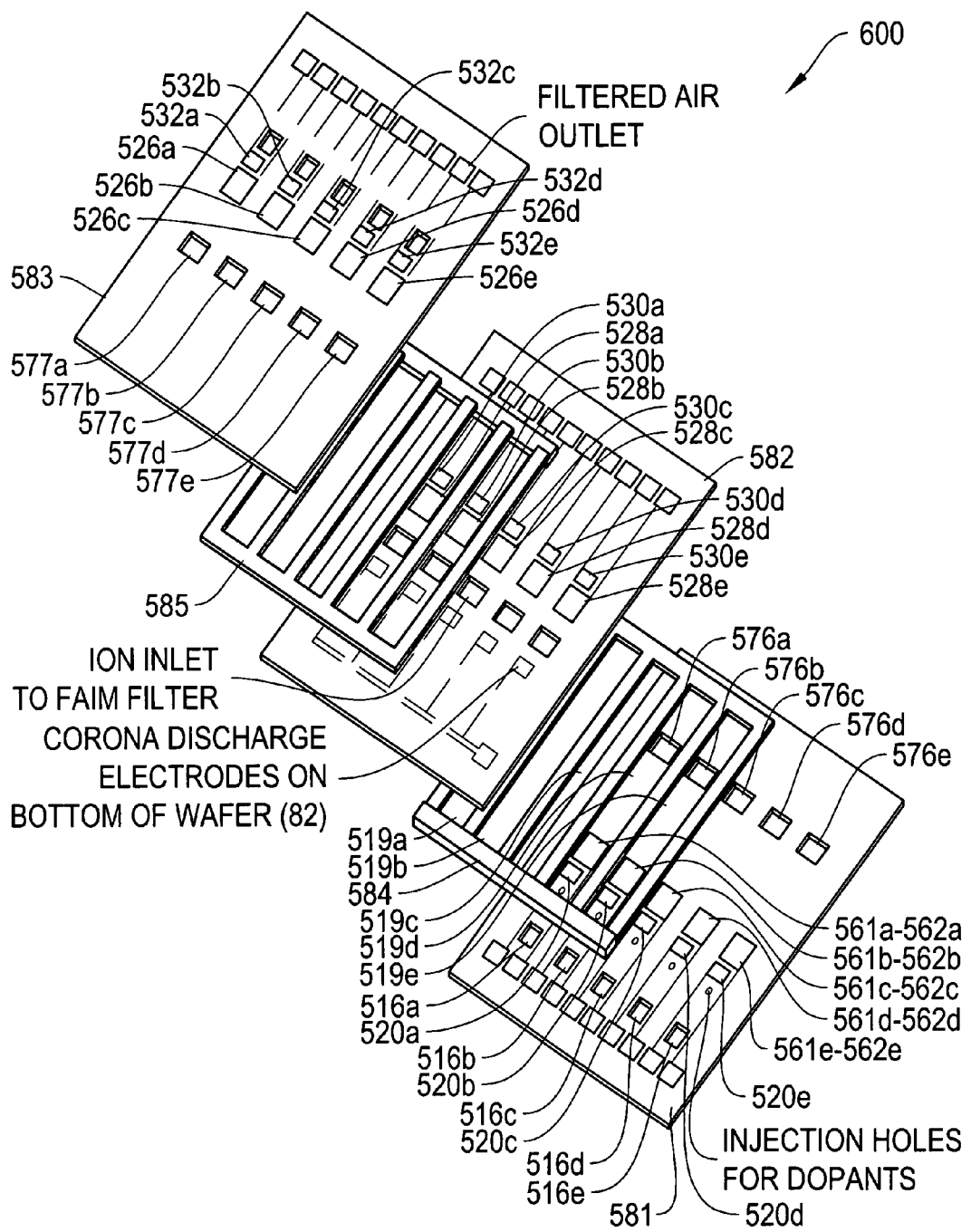
FIG. 21 includes an exploded perspective view of an electro-mechanical component layout, or integrated circuit like structure, for a compact ion mobility based analyzer employing array of DMS filters with multiple flow paths, according to an illustrative embodiment of the invention.

FIG. 21 is an exploded perspective view of a mechanical layout for a compact DMS 600 according to an illustrative embodiment of the invention and including a plurality of flow channels. In a similar fashion to FIG. 20, where substantially the same components depicted in FIG. 1 are employed, only in multiples, the multiples are indicated by the appended a, b, c, d, etc. As shown, the DMS 600 is formed from multiple substrates, including three Pyrex™ glass substrates 581-583 and two semiconductor, e.g., silicon substrates 584 and 585. The top of the substrate 581 is analogous to the top side of the substrate 54 in FIGS. 1 and 6. The bottom of the substrate 582 operates in an analogous fashion to bottom side of the substrate 52 in FIGS. 1 and 6. The substrate 584 provides the necessary spacing between the substrates 581 and 582, while the substrate 585 provides the necessary spacing between the substrates 582 and 583.

The multilayer design of the DMS 600 provides a plurality of flow channel inlets 516a-516e, each having a corresponding outlet 576a-576e. Each flow channel includes a corona discharge electrode 520-520e, respectively, for ionizing a sample. Each flow channel also includes a pair of confinement electrodes 561a-562a, 561b-562b, 561c-562c, 561d-562d, and 561e-562e for directing the flow of sample ions along a respective flow path. Each flow channel further includes an inlet 577a-577e for filtered air, dehumidified air, clean air, or other suitable gas.

The DMS 600 also includes a plurality of dopant injection holes. The dopant injection holes enable any of a plurality of volatile or volatilized compounds, vapors, or gasses to be controllably added to the drift gas. By injecting one or more volatile compounds (e.g., dopants or molecular modifiers) into the flow channel, the spectral characteristics of a sample species can be changed in a predictable and unique manner. The amount, concentration, and/or rate of addition of one or more dopant may be controlled electronically by, for example, a processor 36 or the controller 30 of FIG. 1. In one embodiment, a micromachined pump, injector, or for example, an injet-like mechanism, responsive to the controller 30, selectively introduces an amount of a particular dopant or gas into the DMS 600 to effect sample filtering. Such predictable changes enable enhanced detector discrimination between species having otherwise similar or substantially identical spectral characteristics. According to some illustrative embodiments, different dopants or combinations of dopants may be injected into different flow channels. The result is that the ion filter and detector pairs can each be specialized for analyzing a selected species. Dopants, such as, methylene bromide ($CH_2Br_2$), methylene chloride ($CH_2Cl_2$), chloroform ($CHCl_3$), water ($H_2O$), methanol ($CH_3OH$), and isopropanol, may be introduced, mixed and/or flowed with a sample. The concentrations of these dopants can be less than 1 part per trillion to more than 10%.

Use of arrays is important when there is a desire to measure perhaps a dozen or so compounds in a very brief amount of time. If a fast GC is used as the front end to a compact DMS, such as the DMS 80, the widths of the chemical peaks eluting from the GC can be as brief as a few seconds. To obtain a complete spectral sweep over the required compensation voltage range in time to capture the information contained in the GC, the spectral range can be subdivided amongst each of the filter electrode pairs 526a-528a, 526b-528b, 526c-528c, 526d-528d, and 526e-528e in the array. This allows a concurrent or substantially simultaneous detection of all the constituents in the given GC peak.

Figure 22:
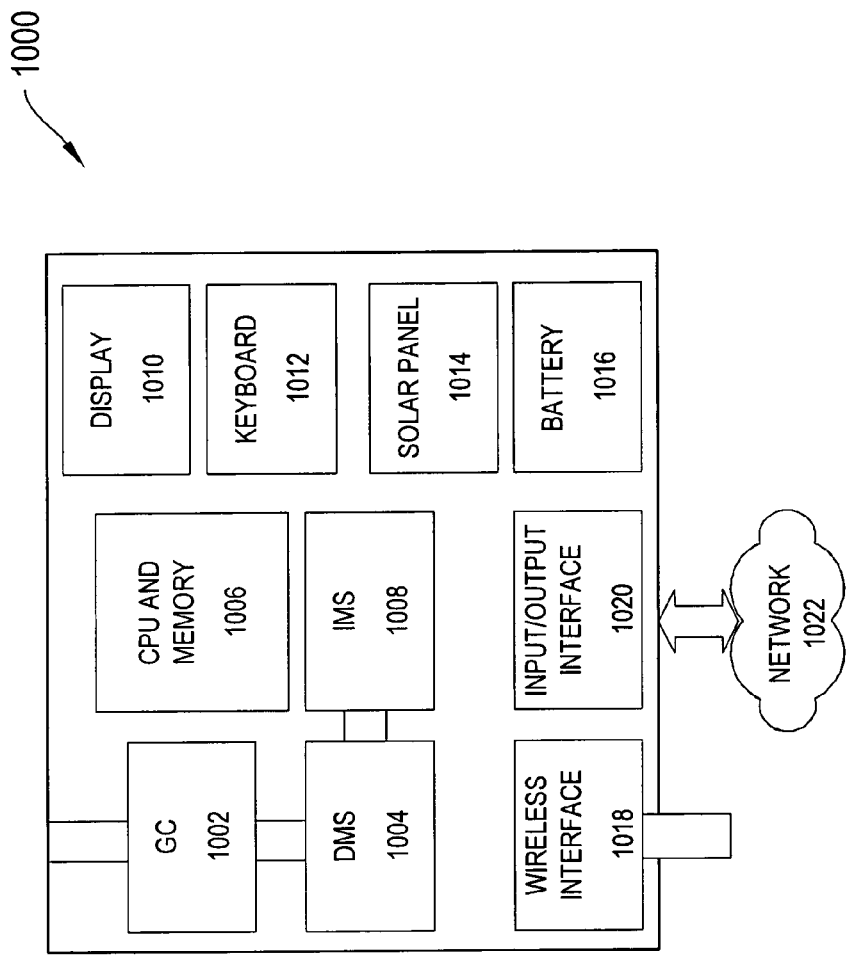
FIG. 22 is a conceptual block diagram of a GC-DMS system including a wireless interface according to an illustrative embodiment of the invention.

FIG. 22 is a block diagram of a GC-DMS sensor system 1000 including a wireless interface 1018, according to an illustrative embodiment of the invention. The GC sensor system 1000 includes various sensor components such as GC 1002, DMS 1004, IMS 1008, CPU/Memory 1006, Display 1010, Keyboard 1012, solar panel 1014, battery 1016, wireless interface 1018, input/output interface 1020. The system 1000 may be connected via interface 1020 to a network 1022 such as the Internet or a local Ethernet to facilitate communications with other sensors or a centralized processing system that controls and/or coordinates the operation of multiple sensor systems 1000. The wireless interface 1018 may also enable communications among multiple sensor systems 1000 via a wireless communications network. In certain embodiments, the sensor is embedded in a flashlight, lapel, helmet, uniform, shoes, boots, jacket, glasses, or any other wearable element.

In another embodiment, the sensor includes a global positioning system (GPS) interface. In a further embodiment, the sensor is wearable and/or communicates with a local or remote display (e.g., a heads-up display on a firefighter's helmet).

In certain embodiments, a solar cell, a fuel cell, and/or a transducer circuit provide a sufficient power source. In one embodiment, the device of FIG. 40 includes a solar panel and interfaces with a rechargeable battery 1016 to provide a solar power source. This allows for monitoring in locations where hardwired power sources are not convenient, or battery replacement is problematic. The source of light energy could be the sun, or artificial lighting, and therefore the sensor 1000 could be used inside or outdoors. The sensor 1000 could be portable or mounted in a fixed location. The solar powered panels could be attached to the sensor 1000, or mounted separately to optimize light collection. The solar panels could also be wearable. In one embodiment, the device of FIG. 40 includes an Ethernet communications interface that enables the extraction of sufficient power for DMS analysis and/or processor processing.

The sensor 1000 or other GC-DMS system such as GC-DMS system 600 may include direct driving control circuitry such as, for example, a MOSFET switch which comprises a control device having low voltage and high frequency capabilities to support significantly narrower gaps within an ultra compact DMS. In one embodiment, the GC-DMS system 600 employs a ring resonator capable of supporting frequencies in the microwave range or higher. In another embodiment, the direct drive is capable of directly generating a square wave signal for the asymmetric field of at least one filter electrode.

In certain embodiments, a GC-DMS system includes a DMS where the DMS field is used as a driving field that preferentially transports ions. In one embodiment, a sample is ionized and introduced into the analytical region (filter region) or is introduced into an ionization region and then flows to the analytical region, such as by electric field. The ions can move in the analytical region against or with a gas flow, such as where a clean gas flow (e.g., filtered air) and flows counter to average or net ion motion. The ions move toward then away from the downstream detector electrode as they travel toward the detector electrode, resulting in an average or net travel, e.g., in two steps forward and one step back. Additional and other means, such as a DC field gradient can be added for assisting ion transport.

The system may use the field dependence of ions, whether high or low. Separations can be achieved based on ion species, including light versus heavy and polarity, according to the displacement vector form the field. Simultaneous detection of both positive and negative ions species is possible as in Miller, et al., U.S. Pat. Nos. 6,495,823 and 6,512,224, both of which are incorporated herein by reference in their entirety.

Thus, in certain embodiments a longitudinal DMS (LDMS) and IMS may be included in the same device and/or integrated package. The LDMS may further interface with one or more GC columns, that may also be integrated into the same package. In an illustrative embodiment, the DMS device provides DMS detection capability but also the DMS is a detector for a conventional IMS, such as time of flight or Fourier IMS. In one mode of operation, the DMS actually measures differential time of flight. In another embodiment, a gating mechanism provides a pulse introduction of sample and enables measurement of time-of-flight.

Figure 23:
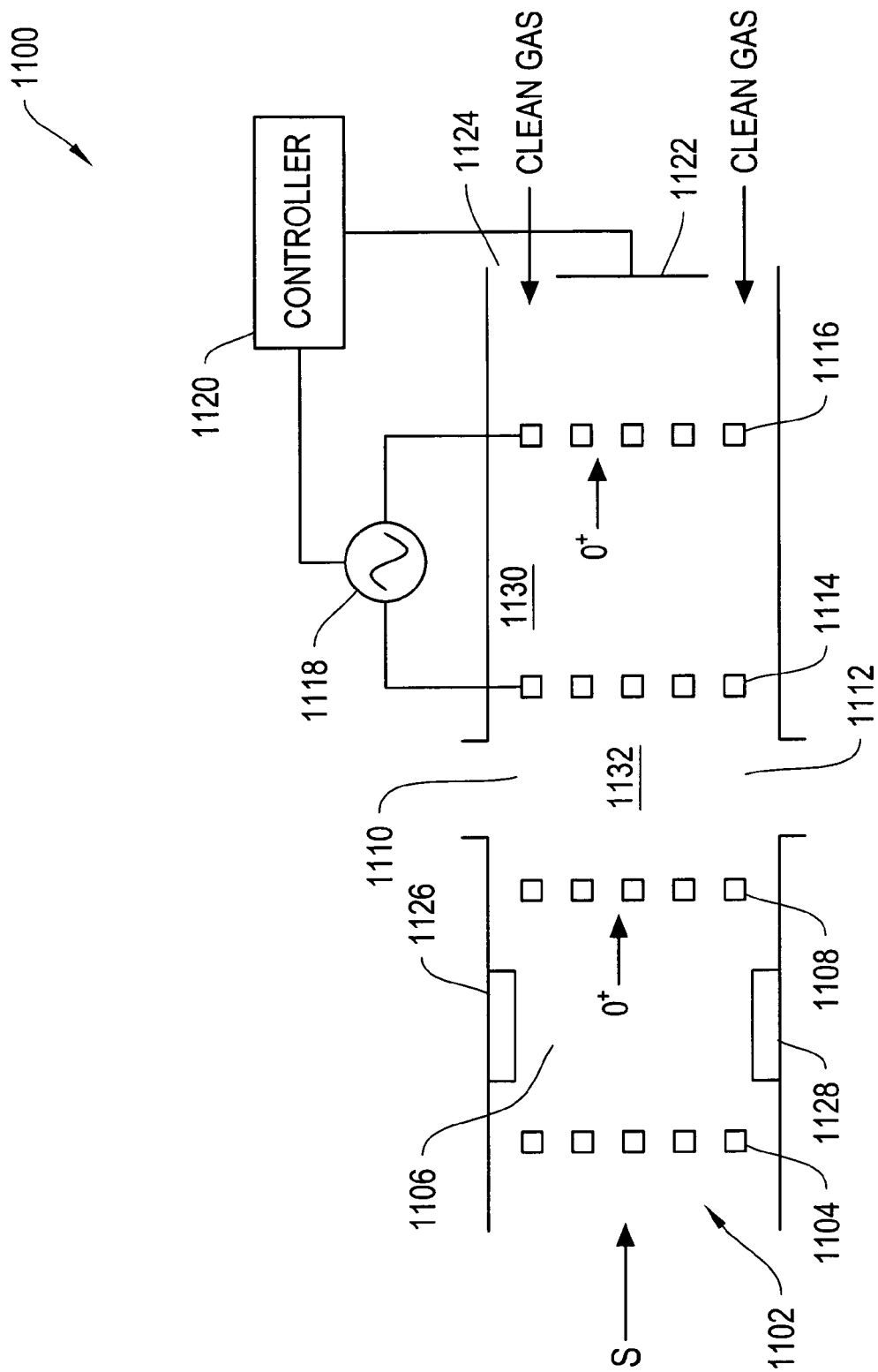
FIG. 23 is a conceptual diagram of a longitudinal DMS, according to an illustrative embodiment of the invention.

FIG. 23 is a conceptual diagram of a longitudinal DMS system 1100 according to an illustrative embodiment of the invention. The longitudinal DMS system 1100 includes a sample S inlet 1102, an ionization region 1106 having ion sources 1126 and 1128, optional propulsion electrodes 1104 and 1108, exhausts 1110 and 1112, flow path 1132, filter grid 1114, analyzer region 1130, filter grid 1116, detector 1122, time-varying voltage source 1118, controller 1120, and clean gas inlet 1124.

In operation, a sample S is introduced via inlet 1102 into the ionization region 1106. One or both of the optional propulsion electrodes and/or grids 1104 and/or 1108 may generate an electric field to propel the ions along the flow path 1132. One or both of the ion sources 1126 and/or 1128 may ionize the sample S. The ion sources 1126 and 1128 may include a radioactive ion source, plasma discharge source, or other ionization source. Once ionized, the ions travel along the flow path 1132 until reaching the filter/gating electrode and/or grid 1114. The exhausts 1110 and 1112 may provide an outlet of excess transport gas or for a counter-flowing gas from the clean gas inlet 1124. The filter grid 1114 may operate as a gate to pulse ions into the analyzer region 1130 at certain times. By pulsing select ions into the analyzer region at certain times, the time-of-flight of the ions can be measured from the time of entry into the region 1130 until the ions reach the detector 1122. The filter electrode and/or grid 1116 may be synchronized with the grid 1114 to gate certain ions through to the detector and reduce possible interference in the flow path 1132.

The voltage source 1118 applies a time-varying voltage across the electrodes 11114 and 1116 to generate a time-varying electric field within the analyzer region 1130. In one embodiment, the time-varying electric field is an asymmetric field including a DC compensation field. The controller 1120, like the controller 10c of FIG. 2A, may selectively adjust the time-varying RF voltage and a compensation voltage applied to the electrodes 1114 and 1116 to allow select ion species to pass through the analyzer region 1130. Unlike the time-varying field generated by filter electrodes 26 and 28 of the system 10 which is orthogonal to the ion flow, the time-varying field of the system 1100 is substantially parallel with the ion flow in a longitudinal direction along the flow path 1130. Thus, the time-varying field effects the average net flow a different ion species differently and, thereby, causes different ions species to arrive at the detector 1122 at different times, based on each ion species mobility characteristics.

The controller 1120 may include a processor capable of measuring and/or analyzing the detected ions over a period of time as the ions reach to detector 1122. In one embodiment, the voltage generator 1118 is adjustable in response to the controller 1120 to adjust the field strength in the analyzer region for both high field and low field values. Thus, the system 1100 may operate as an IMS under low field conditions in one mode, under a mixed high/low field regime in a mixed mode, or under high field conditions in another mode of operation. In another embodiment, a clean gas is introduced at the inlet 1124 that includes filtered air. In certain embodiments, the grids such as grid 1114 are circular, meshed grids. In certain embodiments, the gate 1114 is pulsed open to allow ions into the analyzer region 1130 at various intervals. In one embodiment, the potential of grid 1116 is maintained at about ground while the detector 1122 is slightly biased.

In a further embodiment, as the ions are pulsed into the analyzer region 1130, the gate 1116 is simultaneously pulsed open. Due to the delay in ions reaching the gate 1116 based on their time of flight, the stream of ions may come into and/or out of phase with the gate 1116 as it opens and closes. Thus, an interference signal may be produced that rises and falls depending on the degree to which the gate 1116 is opened and closed.

Figure 24:
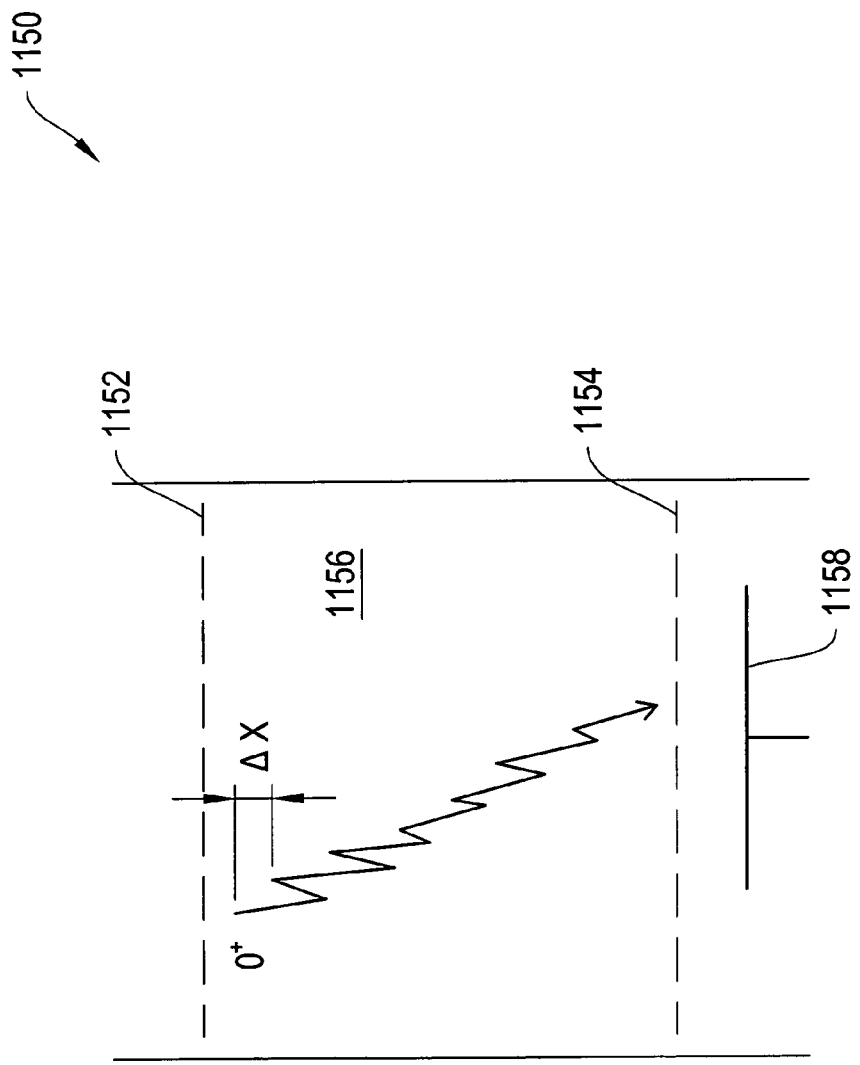
FIG. 24 is an exemplary diagram of the flow path of an ion within the analytical region of the analyzer of FIG. 41, according to an illustrative embodiment of the invention.

FIG. 24 is an exemplary diagram 1150 of the flow path of an ion within the analytical region of the analyzer of FIG. 41 according to an illustrative embodiment of the invention. The diagram 1150 includes an analyzer region 1156 with filter/gate electrodes 1152 and 1154. As discussed above, a time-varying field is applied across the electrodes 1152 and 1154. When an ion is subjected to both high field and low field components of a time-varying electric field, the ion travel a distance under the high field condition, but then travel back a distance under the low condition, creating a net displacement $\Delta X$ in the analyzer region 1156. The net displacement $\Delta X$ allows the ion to travel over a period of time through the analyzer region 1156 to a detector for a time of flight measurement. Because the ion mobility characteristics vary among various ion species, the various ion species become separated over time an arrive at different times at the detector 1158. Thus, a longitudinal DMS enables a differential time-of-flight analysis of various ion species.

Figure 25:
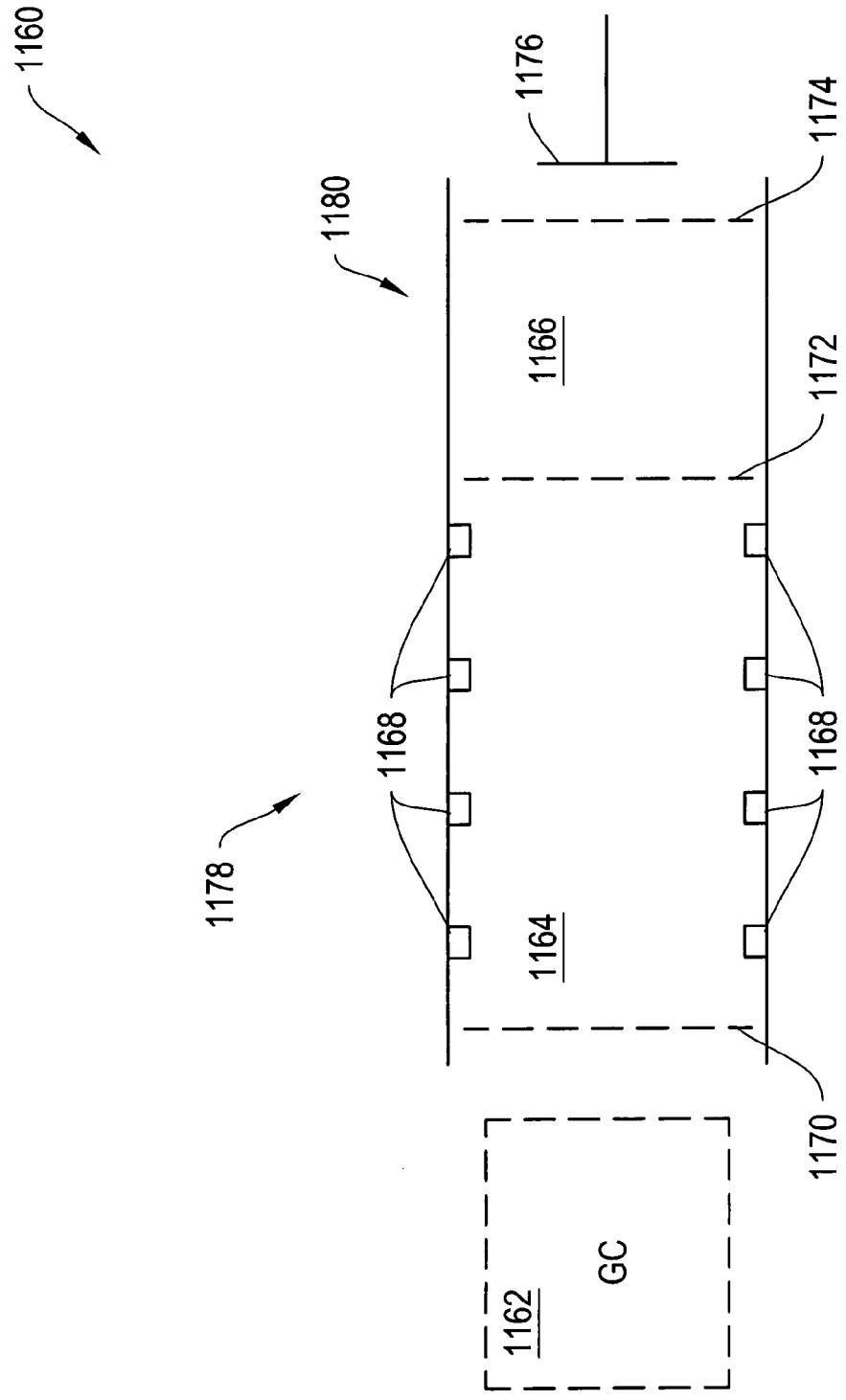
FIG. 25 is a conceptual block diagram of a GC-IMS-DMS system, according to an illustrative embodiment of the invention.

FIG. 25 is a conceptual block diagram of a GC-IMS-DMS system 1160 according to an illustrative embodiment of the invention. The system includes a GC 1162, a IMS 1178, and DMS 1180. The IMS 1178 includes a drift region 1164, gradient electrodes 1168, and gate 1170. The DMS 1180 includes filter/gate electrodes 1172 and 1174, and detector 1176. In the GC 1162, sample constituents are separated with respect to time within one or more GC columns before introduction into the IMS 1178.

In the IMS 1178, gas-phase ion mobilities are determined using a drift tube and/or region 1164 with a constant electric field generated by gradient electrodes 1168. Ions are gated into the drift region 1164 by gate 1170 and are subsequently separated depending upon differences in their drift velocity. The ion drift velocity is proportional to the electric field strength at low electric field strength, for example 200 V/cm, and the mobility, K, which is determined from experimentation, which is independent of the applied electric field. Additionally, in the IMS 1178, the ions travel through a bath gas that is at sufficiently high pressure such that the ions rapidly reach constant velocity when driven by the force of an electric field that is constant both in time and location.

In the DMS 1180, the ions are then subjected to a longitudinal time-varying electric field between filter electrodes 1172 and 1174. Filter electrode 1172 may gate ions into the analyzer region 1166 which are separated with respect to time before reaching the detector 1176. The system 1160 may includes an array of GCs, array of IMSs, and an array of DMSs, integrated within an integrated package.

In certain embodiments, the GC-DMS system 600 and/or sensor 1000 are implemented in an ultra compact form factor. Having such a small form factor, the GC-DMS system 600 may be integrated with a PCMCIA card, a SD Card, and/or a computer attachable device, or wireless capability such as Zigbee and 802 based communication protocols. In one embodiment, the small form factor sensor unit 1000 is easily and unobtrusively attachable/detachable to a computing device such as a PC, laptop, PDA, cellular telephone, smartphone, or any other computing device. The ultra compact GC-DMS system 600 and/or 1000 may be integrated within a device supporting other functions such as a smoke detector, environmental sensor, flashlight, cellular telephone, wearable electronic/computing device, chemical dosimeter, and like compact portable devices.

In certain embodiments, the ion mobility based analyzer of any of the foregoing ion mobility based analyzer systems may include a narrow filter and/or flow path gap distance. The analytical gap between at least two filter electrodes (or a one filter electrode and a conductive element or surface) may be less than about 10 nanometer ($10^{-9}$ meters), less than about 20 nanometers, less than about 50 nanometers, less than about 100 nanometers, less than about 200 nanometers, less than about 500 nanometers, less than about 1 micron ($10^{-6}$ meters), less than about 5 microns, less than about 10 microns, less than about 15 microns, less than about 20 microns, less than about 25 microns, less than about 50 microns, less than about 100 microns, less than about 150 microns, and less than about 200 microns. Depending on the gap distance, the ion mobility based analyzer may include a peak time varying, periodic, or asymmetric field voltage of less than about 10 volts, less than about 20 volts, less than about 50 volts, less than about 100 volts, less than about 200 volts, less than about 500 volts, less than about 1000 volts, and less than about 1500 volts. Additionally, the ion mobility based analyzer may employ a time varying voltage, a periodic voltage, or an asymmetric voltage operating at frequencies of greater than about 1 MHz, greater than about 5 MHz, greater than about 10 MHz, greater than about 50 MHz, greater than about 100 MHz, greater than about 500 MHz, and greater than about 1 GHz. In one embodiment, the DMS analyzer includes multiple gap distances to enable enhanced detection using multiple different analytical gaps and/or multiple ion mobility based analyzers in series and/or parallel (e.g., an array of analyzers).

In another embodiment, any of the foregoing ion mobility based analyzer systems may include a monolithic sensor design where one or more sub-assembly pieces are bonded into a final monolithic sensor part. The final part does not require mechanical clamping to hold these pieces together to form gas-tight part. The monolithic and/or solid sensor design may include a structure formed by the low temperature co-fired ceramic (LTCC) process and/or standard, an enhanced LTCC process, an alumina-LTCC hybrid process, a polymer build from sheets process, a polymer build from injection molded parts, and/or a wrapped flex process.

In a further embodiment, any of the foregoing ion mobility based analyzer systems may include a liquid crystal polymer (LCP) board/housing for a DMS analyzer and/or GC column. By employing a LCP material for the sensor, an ion mobility based analyzer system provides an alternative to traditional polyimide film for use as a substrate in flexible circuit construction. Depending on the manufacturing technique, the LCP material eliminates certain inherent limitations of polyimide circuits. The LCP material also provides advantages to enhanced electronic device design with good electrical performance and processing capabilities such as a lower dielectric constant. The lower dielectric constant allows faster electric signal transfer, and lower moisture absorption which leads to higher frequency signal and data processing.

According to one embodiment, a compact integrated ion mobility based analysis system includes at least one gas chromatograph (GC) column and at least one ion mobility based sample analyzer. Optionally, the at least one GC and the at least one ion mobility based sample analyzer are formed as an integrated circuit in a single package. The GC column receives a sample and elutes constituents of the sample, each of the eluted constituents being temporally separated from each other. The mobility based sample analyzer receives the eluted constituents from the GC and analyzes them based on their ion mobility characteristics of the eluted constituents. According to one feature of the invention, both the carrier gas in the at least one GC column and the drift gas in the at least one ion mobility based sample analyzer consist substantially of air.

According to one feature, the at least one GC column is formed as a capillary column in a substrate. The at least one GC column may be configured, for example, to include a spiral portion, and/or a spiral/counter-spiral portion on the substrate. It may also be configured to have one or more straight portions and one or more curved portions. The spirals may trace a plurality of any suitable geometric patterns including, for example, an oval, triangle or rectangle. According to various configurations, the at least one GC column has a length of less than about 20 meters, 10 meters, 8 meters, 6 meters, 4 meters, 2 meters, or 1 meter, or 100 cm, or 10 cm, or 1 cm. The substrate on which the GC column is formed may be made, for example, from silicon, GaAs, sapphire, alumina, plastic polymer, or other substrate material.

Generally the ionization sources which can be used in or with typical ion mobility based analyzer systems may include field emission tip based ionization source which emits electrons at relatively low voltages, the field emission tip may be formed by nano-fabrication such as from carbon nano-tubes. The ionization source may be a reverse flow plasma source, where the ions formed by the plasma are extracted from the plasma region by an electric field which drives the ions into the DMS or IMS counter to a gas or air flow. In this way, neutrals such as NOx's are minimized and a favorable negative ion chemistry preserved in the DMS.

The ionization source may also be radioactive Ni63 or other radioactive materials. The ionization source may be a PID, or UV ionization source or an LED or a UV LED or the like. Another ionization source may be realized by electrospraying a solvent which ionizes the solvent and then mixing the ionized solvent with the analyte. A charge exchange occurs which then ionizes the analytes.

The detector or detectors employed in the foregoing ion mobility based analyzer systems may include a functionalized chemo-resistive transducer, a polymer functionalized field effect transistor (FET). The FET gate may be functionalized to collect select ions and/or ion species. A particular FET structure may be employed such as a MOSFET, JFET, and other like FET or like semiconductor structure such as a transistor, diode, switch, varactor, and so on. The detector may include a dielectric barrier discharge detector. The detector may include a functionalized nanotube detector and/or a cantilever type detector. The cantilever type detector may be silicon micromachined. The detector may include one or more nano-sensor and nano-structures to facilitate the detection of certain ions. The nanotube may be utilized as a semiconducting transducer. The detector may also detect based on surface plasmon resonance characteristics and interactions between the analyte and the transducer. In other applications the DMS can be coupled to a RAMAN spectrometer or other optical spectrometers for enhanced compound identification or detection.

Detection in the cantilever detector may be based on resonance change of the cantilever or positional deflection of the cantilever. This detection provides different, orthogonal data to the information based on ion mobility or differential mobility provided by DMS and IMS systems.

Additionally, components of the above systems may be nano-machined and/or machined using nano technology. For example, the systems may include nanoinjectors and/or traps nano-based columns, and columns including or being packed with nanotubes.

Figure 26:
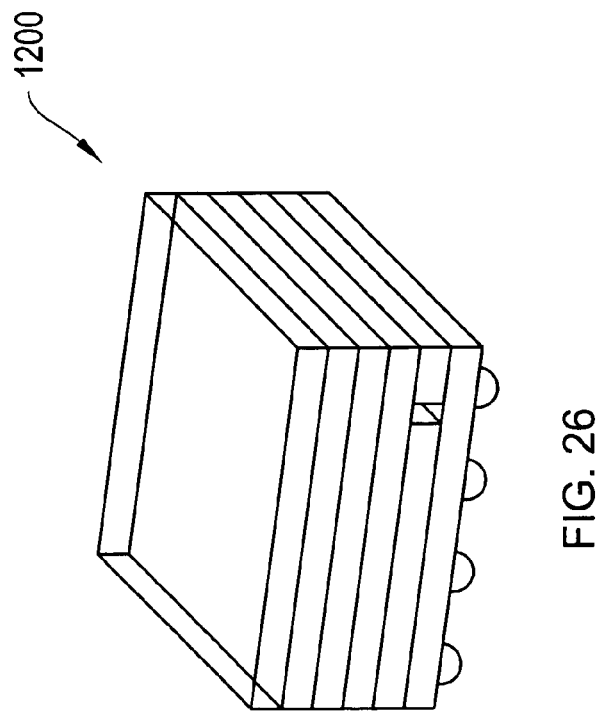
FIG. 26 is a perspective view of a multi-layers chip assembly analyzer including an ion mobility based filter, according to an illustrative embodiment of the invention.

FIG. 26 is a perspective view of a multi-layers chip assembly analyzer 1200 including an ion mobility based filter according to an illustrative embodiment of the invention. In one embodiment, the analyzer 1200 is formed from a number of separate layers bonded together. The ion channels are oriented vertically so that ion movement is directed perpendicular to the silicon substrate surface. This geometry permits subsystems to be segregated to separate wafer layers that are stacked and bonded in the order of ion flow, producing a fully integrated analyzer with the smallest possible size.

Figure 27:
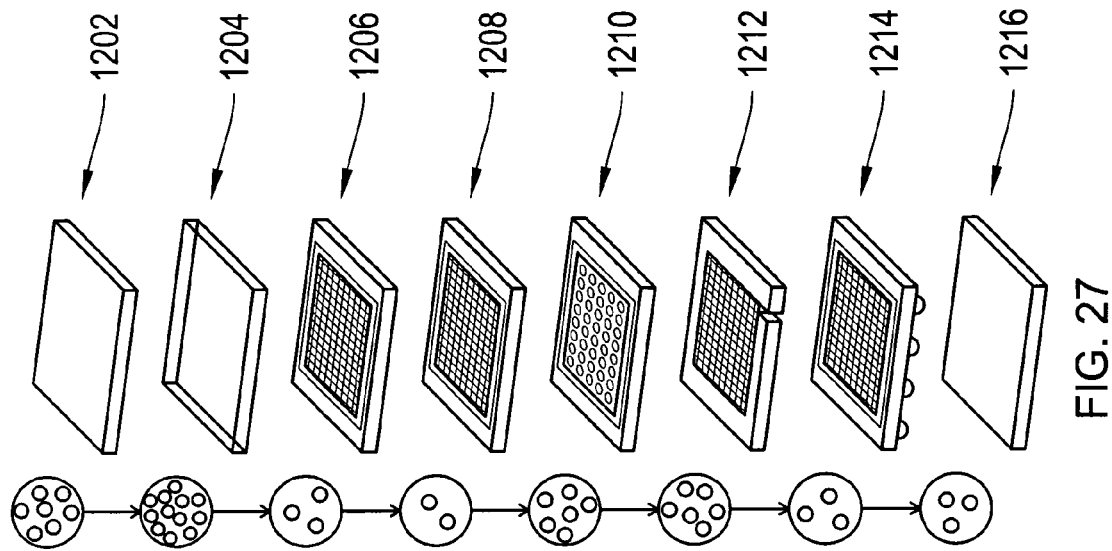
FIG. 27 is an exploded view of the chip assembly analyzer of FIG. 26 that shows the functionality of each layer of the chip assembly, according to an illustrative embodiment of the invention.

FIG. 27 is an exploded view of the chip assembly analyzer 1200 of FIG. 26 that shows the functionality of each layer of the chip assembly according to an illustrative embodiment of the invention. In one embodiment, the analyzer 1200 includes a number of layers. From top to bottom, these layers may include: a gas chromatograph (GC) layer 1202, an inlet layer 1204 having a porous ceramic which allows entry of analytes to the analyzer, dehumidifier layer 1206 configured to remove water vapour from the sample, a preconcentrator layer 1208 that, for example, concentrates the admitted analyte, an ionizer layer 1210 that may include a radioactive source deposited onto a substrate, an ion mobility based filter layer 1212, a detector layer 1214 that may include one or more electrodes and electrical connections to an electronic controller and/or data processor, and another analyzer layer 1216. The GC layer 1202 may include a micromachined GC column as described in other embodiments herein. The GC layer 1202 may be bonded to one or more other layers of the analyzer 1200. The GC layer 1202 may include at least one GC column outlet on a surface in communication with another layer to facilitate fluid communication between the micromachined GC column and the other layer such as the filter layer 1212.

The analyzer layer 1216 may include a chemical based sensor for detecting neutrals and/or ions based on certain chemical properties, an ion mobility based analyzer such as an IMS, DMS, hybrid IMS/DMS, tandem IMS/DMS, MS, or other sample analyzer. The analyzer layer 1216 may include multiple layers. The analyzer layer 1216 may be interposed between, before, after, along side, or in communication with any of the other layers of the analyzer 1200. For example, the analyzer layer 1216 may include a DMS and be positioned after the GC layer 1202, but before the inlet layer 1204. In another embodiment, the GC layer 1202 is positioned after the preconcentrator layer 1208 and before the ionizer layer 1210. The GC layer 1202 may be may be interposed between, before, after, along side, or in communication with any of the other layers of the analyzer 1200 as necessary to enhance sample analysis. In a further embodiment, the analyzer layer 1216 includes a planar ion mobility based analyzer of the type disclosed in FIGS. 20 and 21. In certain embodiments, multiple additional analyzer layers 1212 may be included at various locations within and/or in communication with the analyzer 1200.

In one embodiment, the filter layer 1212 and detector layer 1214 are merged by using a silicon on insulator (SOI) wafer handle layer as the detector electrode and depositing integrated circuitry on the backside of the wafer. Alternatively, the control electronics and/or processor are located external to the analyzer 1200 chip assembly. In another embodiment, the dehumidifier and preconcentrator layers 1206 and 1208 are integrated on the same layer, or moved outside of the device and into the cavity housing the analyzer 1200. The ionizer layer 1210 may be integrated with the inlet layer 1204 by patterning a metallic radioisotope film on the underside of the inlet substrate and/or slab. In one embodiment, the analyzer 1200 includes two layers: an integrated filter and detector layer fabricated in a single SOI wafer, and a porous inlet cap with metal ionization material patterned on the underside.

In one embodiment, the microstructured and/or micromachined filter layer 1212 uses low voltages and implements a method of analyte transport that eliminates the need for moving gas flows and allows pumpless operation. In another embodiment, the filter layer 1212 uses a carrier gas flow to transport both positive and negative ions concurrently and/or simultaneous through the filter layer 1212 for concurrent and/or simultaneous analysis of positive and negative ions. In certain embodiments, microscale thermal isolation enables low power operation of a fast microscale preconcentrator in the preconcentrator layer 1206. In one embodiment, a closely integrated detector improves sensitivity. The small size of the analyzer 1200 cavity allows a less complex approach for removing performance degrading humidity. In certain embodiments, a batch fabrication employing micro-electromechanical system (MEMS) implementation enables simple mass production of analyzers.

Figure 28A:
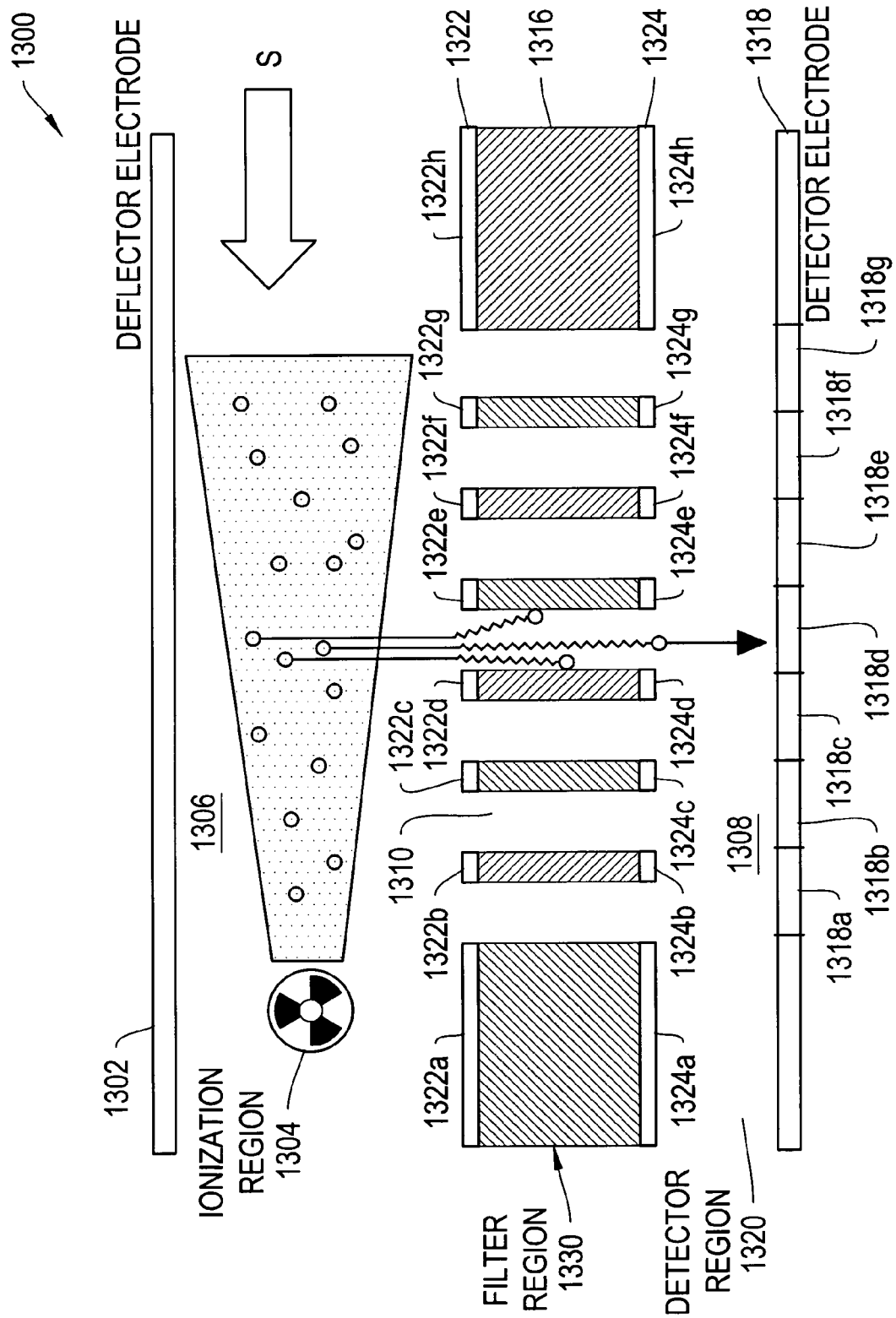
FIG. 28A is a conceptual diagram of an ion mobility based analyzer associated with the chip assembly of FIG. 26, according to an illustrative embodiment of the invention.

FIG. 28A is a conceptual diagram of an ion mobility based analyzer 1300 associated with the chip assembly of analyzer 1200 in FIG. 26 according to an illustrative embodiment of the invention. The analyzer 1300 includes an ionization region and/or layer 1306, a filter region and/or layer 1330, and a detector region and/or layer 1308. The ionization region and/or layer 1306 includes an ionization source 1304 and at least one deflector electrode 1302. The filter region and/or layer 1330 includes conductive layers 1322 and 1324 on the top and bottom surface, respectively of a silicon wafer 1316. Although not shown, an insulative layer may be included between the conductive layer 1322 and silicon wafer 1316 and between the conductive layer 1324 and the silicon wafer 1316. The filter region may include a plurality of filter channels and/or flow paths such as flow path 1310. The plurality of flow paths may segment the conductive layer 1322 into a plurality of conductive layer surfaces and/or electrodes 1322a-h. The plurality of flow paths may segment the conductive layer 1324 into a plurality of conductive layer surfaces and/or electrodes 1324a-h.

In one embodiment, the plurality of conductive electrodes are configured in an interdigitated manner such that, for example, electrodes 1322a, 1322c, 1322e, and 1322g are in electrical communication with each other while electrodes 1322b, 1322d, 1322f, and 1322h are in electrical communication with each other, effectively forming an interdigitated electrode and/or analytical pair. Likewise, electrodes 1324a, 1324c, 1324e, and 1324g are in electrical communication with each other while electrodes 1324b, 1324d, 1324f, and 1324h are in electrical communication with each other, effectively forming another interdigitated electrode and/or analytical pair.

In another embodiment, one, some, or all of the electrodes 1322a-h and 1324a-h are independently connected to a voltage generation source and/or controller such as controller 30 of FIG. 1 to configure the electrodes associated with the channels in the filter region 1330 to selectively apply certain field conditions independently in each channel. In one instance, the electrodes 1322 may be configured in an alternating or interdigitated manner to effectively provide a pair of filter electrodes. In another instance, a different time varying voltage condition may be applied to different electrodes. For example, electrodes 1322b, 1322d, 1322f, and 1322h may be biased by a controller at a ground or neutral potential while the controller applies a time varying voltage over a first frequency range to the electrode 1332a, a time varying voltage over a second frequency range to the electrode 1322c, a third frequency range to the electrode 1322e, and a forth frequency range to the electrode 1322g. A similar configuration may be applied to the electrodes 1324. The time varying voltage may be symmetric or asymmetric, vary in frequency, vary in magnitude, vary in duty cycle, vary in shape, and/or vary in period. The frequency of the time varying voltage and/or signal, and resulting time varying electric field, may vary over a range of 0-100 Mhz.

In another instance where a compensation voltage is employed to support ion filtering along with an asymmetric voltage, the compensation voltage associate with each or a portion of the channels may be adjusted independently. For example, electrodes 1322b, 1322d, 1322f, and 1322h may be biased by a controller at a ground or neutral potential while the controller applies and/or sweeps a compensation voltage over a first compensation voltage range to the electrode 1332a, a compensation voltage over a second compensation voltage range to the electrode 1322c, a third compensation voltage range to the electrode 1322e, and a forth compensation voltage range to the electrode 1322g. A similar configuration may be applied to the electrodes 1324.

In one embodiment, a first portion of the electrodes 1322 and 1324 are biased to propel positive ions through a portion of the channels of the filter region 1330, while a second portion of the electrodes 1322 and 1324 are bias to propel negative ions through a portion of the channels in the filter region 1330. For example, the electrodes 1324b and 1324c may be biased at a positive potential in relation to the electrodes 1322b and 1322c to create a voltage gradient and propulsive field for propelling negative ions through the filter flow channel 1310. Alternatively, the bias may be negative such that positive ions are propelled through flow channel 1310.

The ion mobility based filter may include a plurality of ion filter flow channels such as flow channel 1310. The number of channels may be greater than 5, greater than 10, greater than 15, greater than 20, greater than 30, greater than 40, greater than 50, greater than 100. The ion filter flow channels may include a plurality of electrode fingers forming a comb-like arrangement. In one embodiment, the ion mobility based filter includes two interdigitated electrode arrays, each array having a plurality of electrode fingers. The fingers may be curved. The ion filter flow channels may include, at least at either end, a plurality of electrodes with apertures and/or slots.

The ion mobility based filter may include a resistive or semiconductive substrate on which the conductive layers and non-conductive layer are deposited. The substrate may include an ion detector. In one embodiment, the substrate is a separate from the detector. The substrate and/or the non-conductive layer may include silicon in the form of, without limitation, silicon dioxide or silicon nitride. The substrate may be in the form of a silicon wafer. The conductive layers may include doped polysilicon. In certain embodiments, where the analyzer 1300 includes components on a micromachined scale, the conductive and non-conductive layers (and optionally the substrate, if a separate substrate is provided) may be etched to form a desired shape and configuration, and to provide the ion filter channels, using conventional semiconductor processing techniques. Thus, in certain embodiments, the ion mobility based filter includes many channels that are formed in parallel and on a relatively small scale.

In certain embodiments, the length of the ion filter flow channel is less than the depth of the ion mobility based filter. In one embodiment, the length is at least 10 times less. In other embodiments, the length is at least 15 times, 20 times, 25 times, or 50 times less. In certain embodiments, the ion mobility based filter has a generally wafer-like fore, with the channel length being a fraction of the filter depth. In certain embodiments, the channel length is less than 1000 microns, less than 900 microns, less than 800 microns, less than about 750 microns, less than about 700 microns, less than about 600 microns, less than about 500 microns, less than about 400 microns, less than about 200 microns, and less than about 100 microns, while the filter width is more than about 1000 microns, more than about 2000 microns, more than about 5000 microns, more than about 7500 microns, more than about 9,500 microns, more than about 10,000 microns, more than about 12,500 microns, and more than about 15,000 microns. In certain embodiments, the ion filter flow channel lengths are from about 5000 to 50 microns, from about 1000 to 100 microns, from about 800 to 300 microns, from about 500 to 300 microns, from about 450 microns to 250 microns, and from about 100 to 10 microns.

In certain embodiments, the ion filter flow channels are elongated, including a relatively short length (the direction along which ions will flow) and a relatively short width (in a minor transverse direction), but a relatively long depth (in a major transverse direction).

In certain embodiments, the detector 1318 includes a plurality of segments 1318*a*, 1318*b*, 1318*c*, 1318*d*, 1318*e*, 1318*f*, and 1318*g*. Each segment may be independently connected to a controller and/or processor to enable ion detection. In certain embodiments, the detector 1318 is positioned in proximity with the ion filter region 1330. The detector 1318 may be in contact with the ion filter layer 1330 or at a certain distance from the ion filter layer 1330 to provide a flow channel 1320 through which neutrals may be exhausted from the analyzer 1300 or through which a gas counterflow may be provided to the ion filter layer 1330. By segmenting the detector 1318 in one embodiment, the analyzer 1300 is able to detect both positive and negative ions concurrently where the ion mobility filter is configured to enable concurrent positive and negative ion analysis as described above. In one embodiment, the detector segments are biased independently to enable the detection of different ions exiting the different ion filter flow channels. In another embodiment, the detector 1318 segments have the same bias to capture all ions exiting the ion filter layer 1330. In a further embodiment, the detector electrode 1318 includes a single electrode, conductive surface, or like element capable of detecting ions. In one embodiment, one or more molecular sieves and/or like materials are position in contact with or in proximity with the detector 1318 and/or filter layer 1330 to absorb and/or remove moisture from the system.

In certain embodiments, the ion mobility filter flow channels are substantially perpendicular to a face of the ion mobility based filter and/or analyzer 1200. In one embodiment, the ion mobility based filter includes a face area to channel length ratio of greater than 1:1 (mm), greater than 10:1, greater than 100:1 (mm), greater than 120:1, greater than 150:1, greater than 200:1. In one embodiment, an ion mobility based filter includes an 8 mm×8 mm face area, a face area of about or less than 7 mm×7 mm, a face area of about or less than 5 mm×5 mm, a face area of about or less than 4 mm×4 mm, and a face area of about 2 mm×2 mm. In another embodiment, an ion mobility based filter includes an ion filter flow channel length of about or less than 200 µm, of about or less than 175 µm, of about or less than 150 µm, of about or less than 125 µm, and of about or less than 100 µm.

Figure 28B:
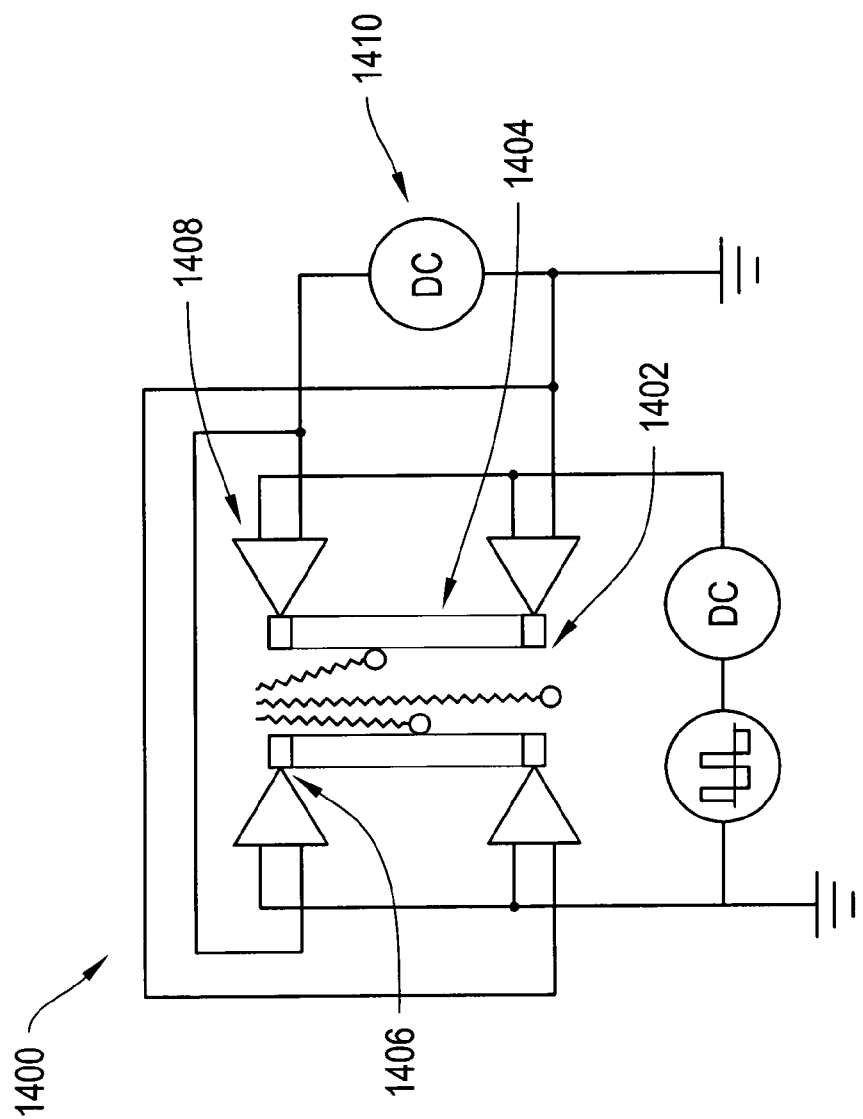
FIG. 28B is a schematic diagram showing the electrical signals that are applied to the ion mobility based analyzer of FIG. 28A, according to an illustrative embodiment of the invention.

FIG. 28B is a schematic diagram showing the electrical signals that are applied to the ion mobility based analyzer 1300 of FIG. 28A according to an illustrative embodiment of the invention. In this embodiment, an interdigitated and/or independently driven and/or connected array of electrodes are formed by etching a dense array of narrow channels through, for example, high resistivity silicon. In one embodiment, ions are driven through the ion filter flow channels by a propulsive electric field. For example, an ion channel 1402 is defined by a silicon substrate 1404 that includes a conductive layer 1406 having electrodes at each corner of the entrance to and exit from the ion filter flow channel. In one embodiment, amplifiers 1408 may include analog adders. In certain embodiments, the conductive layer 1406 includes metal plates.

In one embodiment, a high-voltage time varying field and low voltage DC compensation and/or bias field are generated across the ion filter flow channel that are substantially transverse to the flow of ions. A DC power source 1410 and/or a controller provides applies a voltage differential between the entrance and exit of the ion filter flow channel to generate a propulsive electric field to drive ions through the length of the ion filter flow channel. The ion mobility based filter may operate with a time varying voltage in the range of about 20 to 500 volts, with a time varying frequency in the range of 1 MHz to about 100 MHz, and a propulsive voltage differential of about 5 to 50 volts. Although not shown, additional conductive, resistive and/or insulative layers may be included between, before, and/or after the conductive layer 1406 and substrate 1404. In certain embodiments, the analyzers 1400 and 1300 operate as a DMS employing an asymmetric field, compensation field, and longitudinal/propulsive field as described, for example, and employing additional features of, the systems related to FIGS. 1, 10, 11, 12, 13, 14, 15, 16, 17, and 18.

In other embodiments, a time varying waveform or signal such as, without limitation, a square waveform is applied across each of the electrodes 1322 and 1324, operating as interdigitated structures or structures including independently driven electrodes, such that one phase of the waveform has zero value, making the structures behave as Bradbury-Nielson gates. When the potential applied across the structures 1322 and 1324 is zero, the electric field in the vicinity of the gate region is perpendicular to the filter layer 1330 so that ions are directed through it (the gate is "open"). When the potential applied across the structures 1322 and 1324 is non-zero, the electric field in the vicinity of the gate region is approximately parallel to the filter layer 1330 so that ions are directed into one of the gate electrodes and therefore cannot traverse the filter layer 1330 (the gate is "closed"). The zero value used for each gate is slightly different, so that an electric gradient exists between the gates when open and ions tend to be directed through the filter layer 1330 during this phase. Only ions moving quickly enough (with high enough mobility values) can make it through the filter structure for a particular waveform frequency. Ions with high enough velocities, and hence large mobility values, reach the collector electrode and are detected. Ions with velocities that are too slow, and hence mobility values too small, do not reach the collector. Thus, an ion mobility spectrum of a sample is formed by scanning the frequency of the waveform and differentiating the signal output using a the current amplifier of a controller.

In another embodiment, referring to FIG. 28A, a time varying signal is applied across electrodes 1322*b* and 1322*c*. The time varying signal may be symmetric. The time varying signal is swept from, for example, 100 KHz to 4 MHz over a period of time while ions are propelled through the ion filter flow channel 1310. At lower frequencies, most ions are propelled into one of the filter electrodes and/or surface and are neutralized due to the long period at which traverse potential exists within the flow channel 1310. As the frequency is increased, a small amount of ions will become neutralized because more ions will be moved back and forth traversely as the ions travel the length of the flow channel. At the higher or highest frequency, most of the ions will pass through the ion mobility based filter because even ions with higher ion mobility characteristics will be oscillated back and forth at the high frequency within the flow channel 1310 without contacting an electrode or side wall and, therefore, without being neutralized. By differentiating the detected ion mobility intensity spectrum over the frequency range, a controller may then identify ion mobility peaks associate with changes in the detected ion mobility intensity spectrum. These peaks may be used to identify and/or detect certain ion species. The analyzer 1300 may further include a controller and/or processor that interfaces with a data store of known ion intensity peak spectra. Thus, the detected or differentiated spectrum may be compared with the stored known spectra to identify known ion species.

Figure 28C:
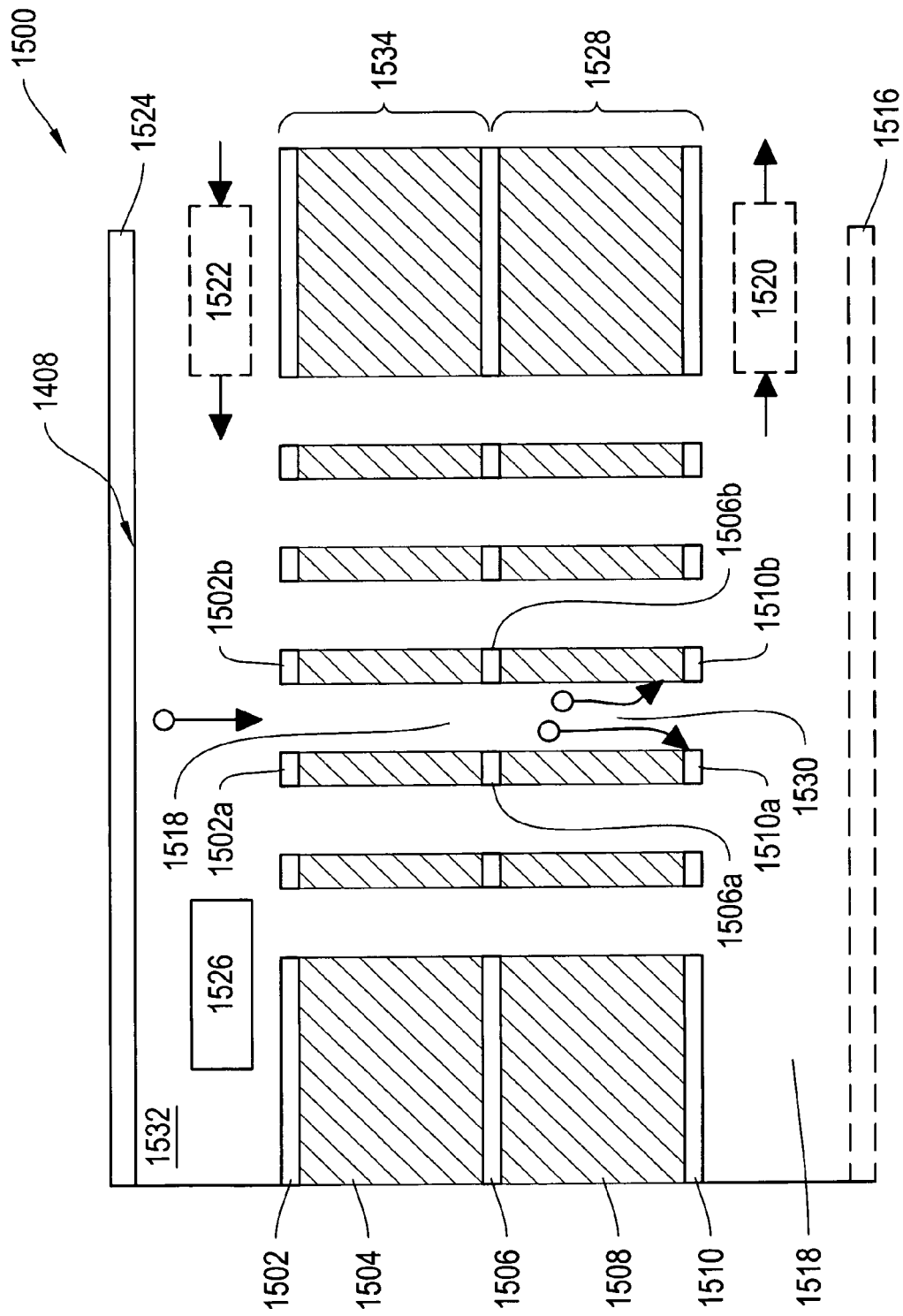
FIG. 28C is a conceptual diagram of an ion mobility based analyzer including a micromachined detector layer having channels corresponding to the channels of an ion mobility based filter, according to an illustrative embodiment of the invention.

FIG. 28C is a conceptual diagram of an ion mobility based analyzer 1500 including a micromachined detector layer 1528 having channels corresponding to the channels of an ion mobility based filter, according to an illustrative embodiment of the invention. The analyzer 1500 includes an ionization layer 1532, a filter layer 1534, and a detector layer 1528. The analyzer 1500 also includes a deflector 1524, an ion source 1526, an outlet region 1518. The analyzer 1500 may optionally include one or more flow generators 1522 and 1520. The flow generators may include a solid state flow generator, a micro electromechanical pump, a pressurized fluid source, or other flow generating means. In certain embodiments, the flow generators induce a flow of a carrier gas, drift gas, and/or carrier gas counterflow within the analyzer 1500. The filter layer 1534 may include a substrate 1504, a conductive surface 1502, a conductive surface 1506, and a plurality of filter flow channels such as flow channel 1518. The conductive surfaces 1502 and 1506 may include interdigitated or individually driven electrodes such as electrodes or conductive elements 1502a, 1502b, 1506a, and 1506b, respectively. The detector layer 1528 may include a substrate 1508 and a conductive layer 1510. The conductive layer 1510 may include metal electrodes, semiconductive materials, or other conductive materials that function as one or more detectors such as detectors 1510a and 1510b. The analyzer 1500 may optionally include a detector 1516.

In operation according to one embodiment, the detector electrodes 1510 are all biased the same to collect like ions in each of the plurality of flow channels including, for example, flow channel 1530 which is aligned with filter flow channel 1518 where filter electrodes 1510a and 1510b collect ions of the same polarity. In this embodiment, a sample is ionized by the ion source 1526 whereupon the ions are deflected into the filter layer by the deflector electrode 1524. The filter layer 1534 filters the ions as described using one of the previously describes techniques such that select ions are passed into one of the plurality of detector channels that are aligned with the filter channels. In this embodiment, the potential difference between the conductive layers 1502 and 1506 provide a propulsive field to, for example, drive the ions through the filter channel 1518 and into the detector channel 1530. In this embodiment, the detector electrodes are biased the same because the propulsive field of the filter can only propels positive or negative ions depending on the voltage differential between the conductive layers 1502 and 1506. As discussed above, in an embodiment where each filter electrode and detector electrode is independently driven, a portion of the filter layer 1534 and detector layer 1528 may be biased to enable positive ion detection while another portion of the filter layer 1534 and detector layer 1528 is biased to enable negative detection.

In an alternative embodiment, the voltage differential and propulsive field between the conductive layers 1502 and 1506 may be removed while a carrier gas flow is used to propel ions through the various layers 1532, 1534, and 1528. The carrier gas flow may be enable by a micro pump, a pressured gas source, or a solid state flow generator such as flow generator 1522 and/or 1520. With no propulsive field in the flow channels such as flow channel 1518, both positive and negative ions are free to be filtered and flow into the detector channels such as detector channel 1530. Detector electrode 1510a may be biased to collect negative ions while detector electrode 1510b may be biased to detect positive ions, both detections occurring concurrently.

In a further embodiment, multiple additional layers 1528 are stacked to provide a series of electrodes along the filter and detector channels. By biasing each of the electrodes such as, for example, electrodes 1502a, 1506a, and 1510a with a DC voltage to form a gradient field and/or propulsive field, the analyzer 1500 may be configured as an IMS and/or TOF IMS. In another configuration, additional layers 1528 may be added to the detector layer 1528 shown and configured to define an ion mobility based analyzer in combination with an IMS or another ion mobility based analyzer in series. Using independently driven electrodes, a matrix and/or array of series and/or parallel ion mobility based filters may be created and operated for enhanced orthogonal analysis of samples. In the basic configuration shown in FIG. 28C, the electrodes 1510a and 1510b may be configured as DC biasing or gradient electrodes for an IMS while detector electrode 1516 operates as the collector. Additionally layers and electrodes may be employed to provide gating and filter functional of conventional IMS systems.

Figure 28D:
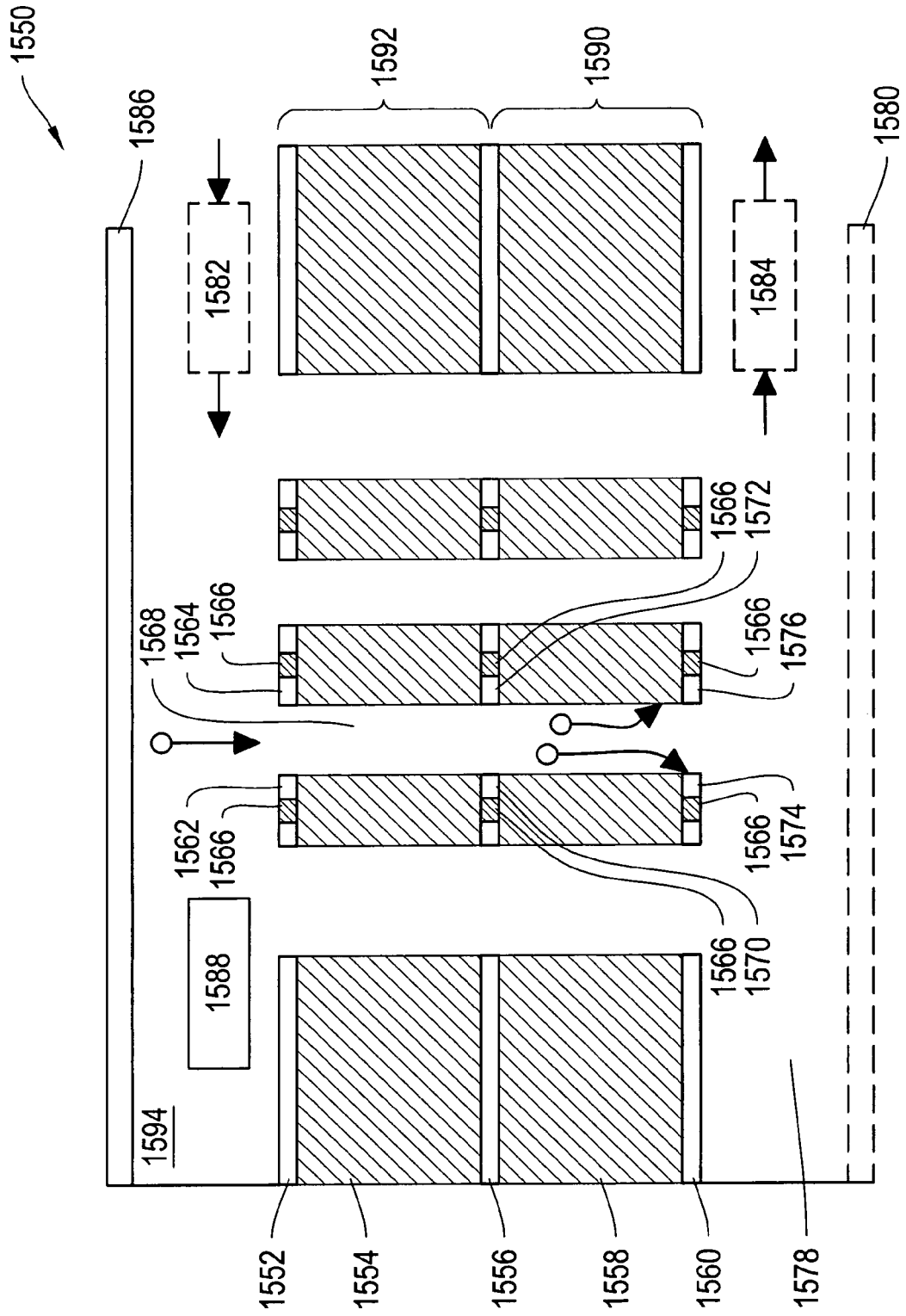
FIG. 28D is a conceptual diagram of another ion mobility based analyzer including a micromachined detector layer having channels corresponding to the channels of an ion mobility based filter, according to an illustrative embodiment of the invention.

FIG. 28D is a conceptual diagram of another ion mobility based analyzer 1550 including a micromachined detector layer 1590 having channels corresponding to the channels of an ion mobility based filter layer 1592 according to an illustrative embodiment of the invention. The analyzer 1550 includes an ionization layer 1594, a filter layer 1592, and a detector layer 1590. The analyzer 1550 also includes a deflector 1586, an ion source 1588, an outlet region 1578. The analyzer 1550 may optionally include one or more flow generators 1582 and 1590. The flow generators may include a solid state flow generator, a micro electromechanical pump, a pressurized fluid source, or other flow generating means. In certain embodiments, the flow generators induce the flow of a carrier gas, drift gas, and/or carrier gas counterflow within the analyzer 1500. The filter layer 1592 may include a substrate 1554, a conductive surface 1552, a conductive surface 1556, and a plurality of filter flow channels such as flow channel 1568. The conductive surfaces 1552 and 1556 may include interdigitated or individually driven electrodes such as electrodes or conductive elements 1562 and 1564, and 1570 and 1572 respectively. The detector layer 1590 may include a substrate 1558 and a conductive layer 1560. The conductive layer 1560 may include metal electrodes, semiconductive materials, or other conductive materials that function as one or more detectors such as detectors 1574 and 1576. The analyzer 1550 may optionally include a detector 1580.

More significantly, in certain embodiments, the conductive surfaces 1552 and 1556 include electrode spacers and/or voids 1566. In one embodiment, the spacer include highly resistive materials such as silicon to provide insulation between an electrode associated with one flow channel from an electrode associated with another channel. In another embodiment, a void 1566 provides the necessary insulation and/or isolated between electrodes associated with different flow channels. The spacer and/or void advantageously reduces electrical interference or noise which degrade the performance or operating conditions within one flow channel due to interference or noise from another channel.

In operation, the analyzer system may operate and include the features described with respect to the analyzer system 1500 of FIG. 28C.

Figure 29A:
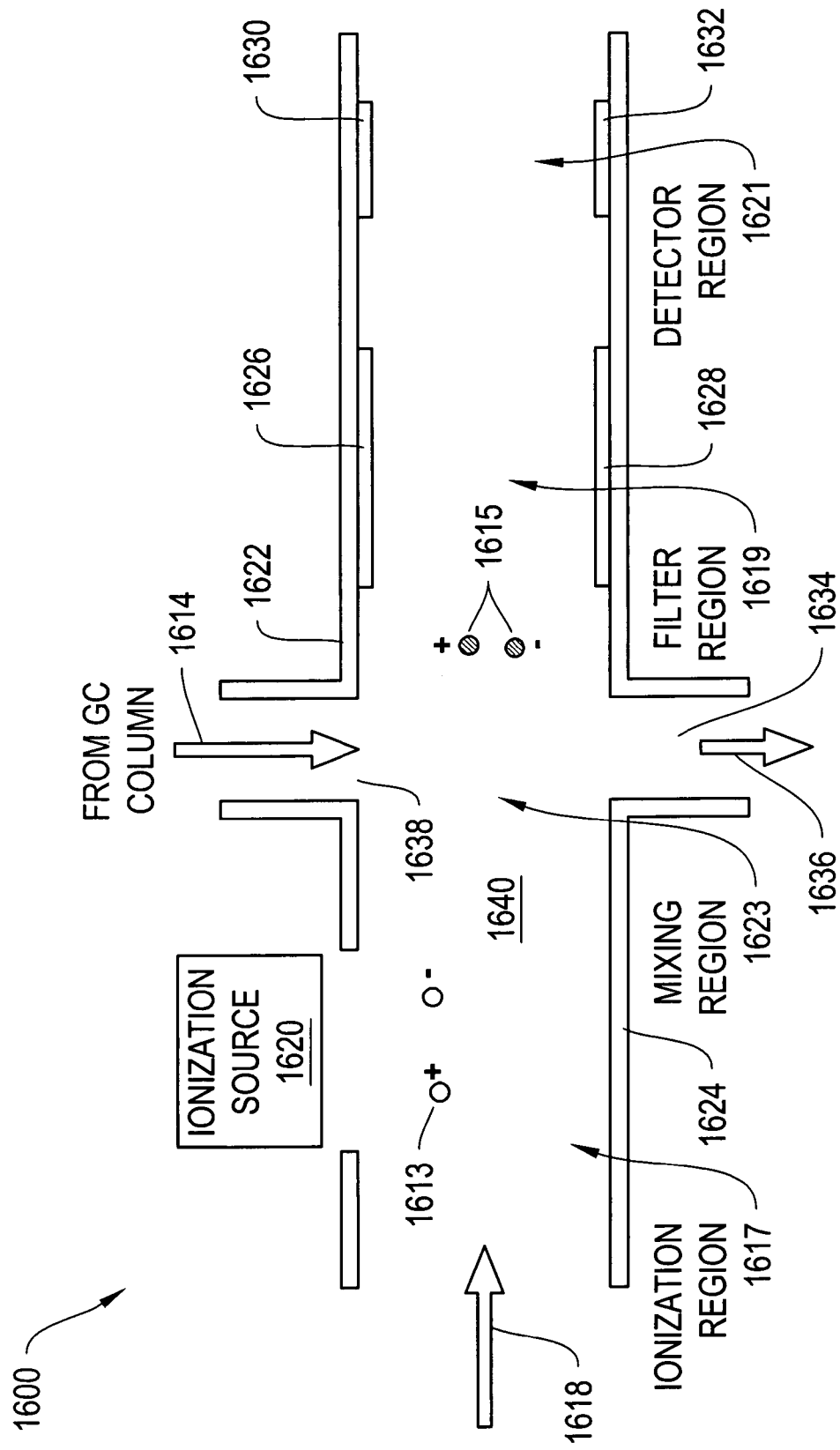
FIG. 29A is a conceptual diagram of an ion mobility based analyzer system having an exhaust in proximity to a GC column effluent to vent excess fluids from analyzer system, according to an illustrative embodiment of the invention.

FIG. 29A is a conceptual diagram of an ion mobility based analyzer system 1600 having an exhaust 1634 in proximity to a GC column effluent 1638 to vent excess fluids from the analyzer system 1600 according to an illustrative embodiment of the invention. In this illustrative embodiment, rather than exposing the sample 1614 to the ionization source 1620, the drift gas 1618, dopant or additive constituents in the drift gas are exposed to and ionized by the ionization source 1620 in the ionization region 1617. The sample 1614 from the GC column enters the flow channel or path 1640 via the GC effluent 1638 into a mixing region 1623. The reactant ions 1613 from the ionized drift gas 1618 or its constituents mix with the sample 1614 in the mixing region 1623 to create product ions 1615. One advantage of this design is that the ionization source 1620 is not exposed to the sample molecules 1614 and cannot react with them, as some chemicals introduced by the GC column may attack the ionization source 1620 and damage it. Using this design, many additional chemicals which ordinarily cannot be used with a particular ionization source 1620 can be used. A vent 1634 removes excess gas 1636 from the system 1600 prior to introducing product ions 1615 to the filter region 1619. Although not shown, the system 1600 may be connected to a recirculation system configured to re-circulate clean gas through the system 1600. The combined system 1600 and the recirculation system may form a closed carrier gas and/or fluid system. Alternatively, the combined system 1600 and recirculation system may include an open fluid system whereby the GC column employs a gas that provides fluid flow through the GC column that is introduced into the system 1600 via the effluent 1638. For such an open system, the vent 1634 advantageously enables the removal the excess gas from the system 1600 and recirculation system without the need to vent downstream of the system 1600 where such a downstream vent is in communication with a recirculation pump.

The product ions 1615 are then flowed through the filter region 1619. The components of the filter region 1619 and the detector region 1621 such as filter electrodes 1626 and 1628 and detector electrodes 1630 and 1632 are substantially identical and operate in the same fashion as the filter and detector electrodes described above with regard to FIG. 1. An important feature of the above described illustrative embodiments is that they enable a light weight, relatively compact, and relatively fast, e.g., millisecond to second, sample analysis by a DMS. As such, it is uniquely suited for field deployment. One way that the invention achieves the above features is by reducing analyzer flow channel or path dead volume and DMS scanning rates. Dead volume is any region in a flow channel or path where there is no flow or low flow.

According to an illustrative embodiment, the invention reduces dead volume, size and weight by providing substrates, such as the substrates 1622 and 1624, that have multiple functional uses. For example, the substrates 1622 and 1624 provide platforms (or a physical support structures) for the precise definition and location of the component parts or sections of the compact system 1600. The substrates, such as the substrates 1622 and 1624, form a housing enclosing the flow channel with the filter region 1619 and perhaps the ionization region 1617 and/or the detector region 1621, as well as other components, enclosed. This multi-functional substrate design reduces parts count while also precisely locating the component parts so that quality and consistency in volume manufacture can be achieved. A description of an exemplary compact or micro-GC system, which may be employed with the invention, is provided by Lu et al. in *Functionally Integrated MEMS Micro Gas Chromatograph Subsystem*, 7$^{th}$ International Conference on Miniaturized Chemical and Biochemical Analysis Systems, October 2003, Squaw Valley, Calif., U.S.A and in U.S. patent application Ser. No. 11/415,564, filed on May 1, 2006, the entire contents of which are incorporated herein by reference.

As mentioned above, the compact system 1600 also has unexpected performance improvements, due for example, to the shorter drift tube/flow channel, and the electrical insulation and spatial isolation provided by portions of the substrates 1622 and 1624. Also, because they are insulating or an insulator (e.g., glass or ceramic), the substrates 1622 and 1624 provide a platform for direct formation of components, such as electrodes, with improved performance characteristics.

It is should be noted that use of the substrates 1622 and 1624 as a support/housing does not preclude yet other "housing" parts or other structures to be built around the compact system 1600. The system 1600 may be included as one layer of a multilayer chip assembly. It may be desirable to put a humidity barrier over the device. As well, additional components, such as batteries, can be mounted to the outside of the substrate/housing, e.g., in a battery enclosure. Nevertheless, embodiments of the compact system 1600 distinguish over the prior art by virtue of performance and unique structure generally, and the substrate insulation function, support function, multi-functional housing functions, specifically, as well as other novel features.

According to various illustrative embodiments, a compact ion mobility based analyzer system has decreased size and power requirements while achieving parts-per-trillion sensitivity. According to one illustrative embodiment, the compact ion mobility based system can have a less than about 5 Watt (W) and even less than about 0.25 mW overall power dissipation, and a size of about a 2-cm$^3$ or less, not including a power source or display, but including an RF field generator. According to some embodiments, a compact ion mobility based analyzer of the invention has a total power dissipation of less than about 15 W, about 10 W, about 5 W, about 2.5 W, about 1 W, about 500 mW, about 100 mW, about 50 mW, about 10 mW, about 5 mW, about 2.5 mW, about 1 mW, and/or about 0.5 mW. According to further embodiments, a compact ion mobility based analyzer system employs a flow generator, such as a MEMS pump, compressed fluid source or a solid-state flow generator as is described in U.S. patent application Ser. No. 10/943,523, filed on Sep. 17, 2004 (incorporated by reference above), optionally including a display (e.g., indicator lights and/or an alphanumeric display) and a power source (e.g., a rechargeable battery) compartment, along with an RF field generator, may have a total package outer dimension of less than about 0.016 m$^3$, 0.0125 m$^3$, 0.01 m$^3$, 0.0056 m$^3$, 0.005 m$^3$, 0.002 m$^3$, 0.00175 m$^3$, 0.0015 m$^3$, 0.00125 m$^3$, 0.001 m$^3$, 750 cm$^3$, 625 cm$^3$, 500 cm$^3$, 250 cm$^3$, 100 cm$^3$, 50 cm$^3$, 25 cm$^3$, 10 cm$^3$, 5 cm$^3$, 2.5 cm$^3$, with the package being made, for example, from a high impact plastic, a carbon fiber, or a metal. According to further illustrative embodiments, a compact ion mobility based analyzer, for example, includes an RF generator, and optionally includes a display, keypad, and power source compartment, may have a total package weight of less than about 5 lbs, 3 lbs, 1.75 lbs, 1 lbs, or 0.5 lbs.

In one practice of the invention, the small size and unique design of the ion mobility based analyzer enables use of short filter electrodes that minimize the travel time of the ions in the ion filter region and therefore minimize the detection time. The average ion travel time td from the ionization region to the detector is determined by the drift gas velocity V and the length of the ion filter region Lf, and is given by the relation td=Lf/V. Because Lf can be made small (e.g., 15 mm or less) in the illustrative ion mobility based analyzer system 1600, and the RF asymmetric fields can have frequencies of about 5 MHz, the response time of the ion mobility based analyzer 1600 can be very short (e.g., one millisecond or less), while the ion filtering (discrimination) can still be very effective.

Figure 29B:
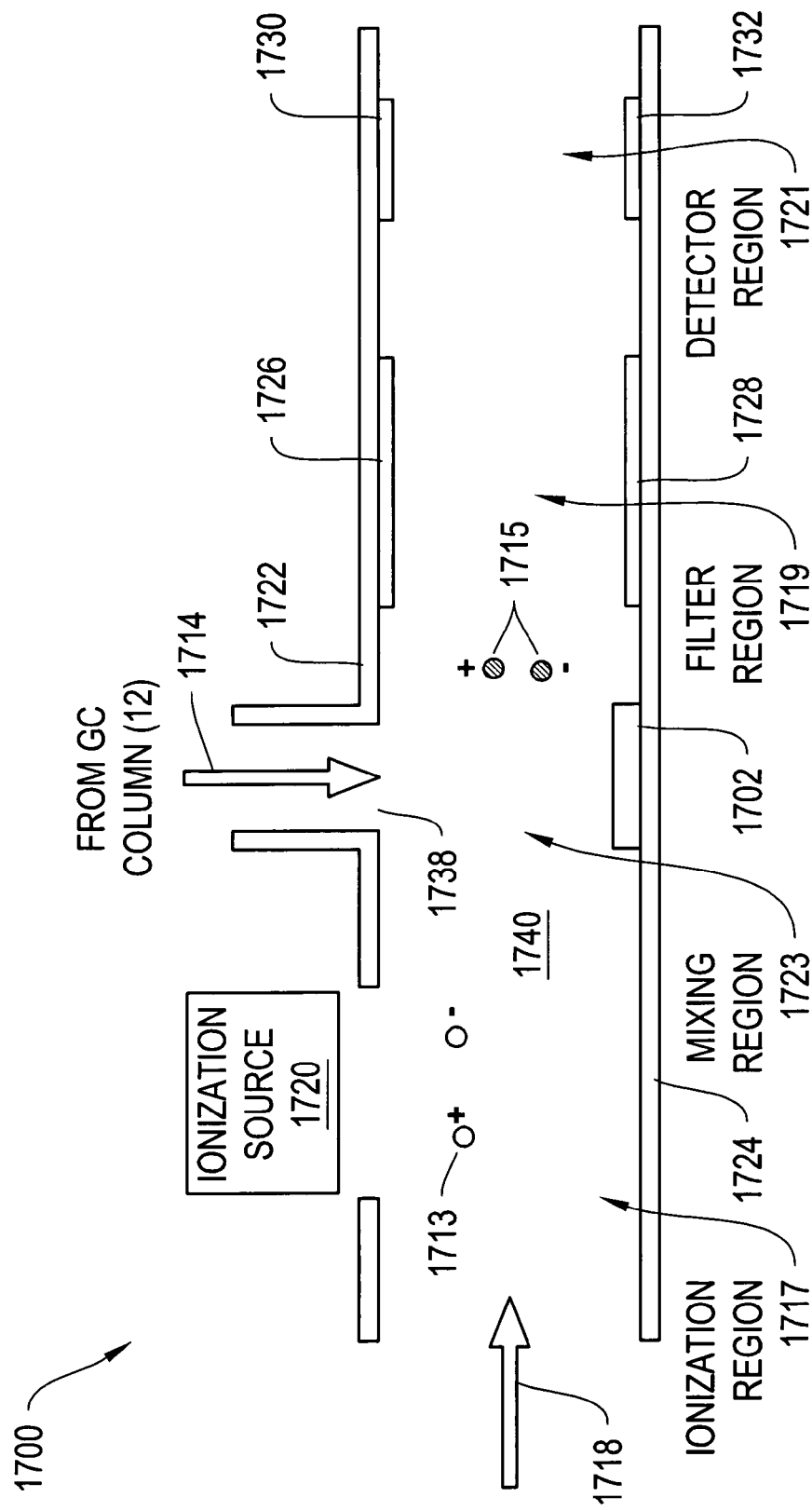
FIG. 29B is a conceptual diagram of an ion mobility based analyzer system including a catalyst capable of removing select gases from the system, according to an illustrative embodiment of the invention.

FIG. 29B is a conceptual diagram of an ion mobility based analyzer system 1700 including a catalyst 1702 capable of remove select gases from the system 1700, according to an illustrative embodiment of the invention. In this illustrative embodiment, rather than exposing the sample 1714 to the ionization source 1720, the drift gas 1718, dopant or additive constituents in the drift gas are exposed to and ionized by the ionization source 1720 in the ionization region 1717. The sample 1714 from the GC column enters the flow channel or path 1740 via the GC effluent 1738 into a mixing region 1723. The reactant ions 1713 from the ionized drift gas 1718 or its constituents mix with the sample 1714 in the mixing region 1723 to create product ions 1715. One advantage of this design is that the ionization source 1720 is not exposed to the sample molecules 1714 and cannot react with them, as some chemicals introduced by the GC column may attack the ionization source 1720 and damage it. Using this design, many additional chemicals which ordinarily cannot be used with a particular ionization source 1720 can be used. The catalyst 1702 enables the removal of excess gas from the system 1700 prior to introducing product ions 1715 to the filter region 1719. The catalyst 1702 may include a material such as a metal. The metal may include, without limitation, platinum and/or palladium. Although not shown, the system 1700 may be connected to a recirculation system configured to re-circulate clean gas through the system 1700. The combined system 1700 and the recirculation system may form a closed carrier gas and/or fluid system. Alternatively, the combined system 1700 and recirculation system may include an open fluid system whereby the GC column employs a gas that provides fluid flow through the GC column that is introduced into the system 1700 via the effluent 1738. For such an open system, the catalyst 1702 advantageously enables the removal the excess gas from the system 1700 and recirculation system without the need to vent downstream of the system 1700 where such a downstream vent is in communication with a recirculation pump. The product ions 1715 are then flowed through the filter region 1719. The components of the filter region 1719 and the detector region 1721 such as filter electrodes 1726 and 1728 and detector electrodes 1730 and 1732 are substantially identical and operate in the same fashion as the filter and detector electrodes described above with regard to FIG. 1.

In certain embodiment of the invention, an ion mobility based analyzer employs enhanced detection techniques to improve analyzer sensitivity and performance. The ability to detect trace levels of chemical compounds is highly desirable for security screening, first responder area assessment, area monitoring, industrial process control, work place hazard warning systems, to name a few. Many instrument systems may be used including all types of mass spectrometry, ion mobility spectrometry, gas chromatography, (high pressure) liquid chromatography, DMS, FAIMS, photoionization detectors (PID), and flame ionization detectors (FID), among other like systems. Each system has benefits and drawbacks relative to the others for given applications and modes of operation. Some systems employ special front ends to pre-condition or concentrate the incoming sample, some filter chemical species from one another as part of their function, but all ultimately detect the sample at some point in their operation. In certain embodiments, an ion mobility based analyzer is operated in combination with any one of the above systems. For example, an ion mobility based analyzer such as a DMS may perform filtering and detection of ions of a sample, while a chemical based detector detects and/or measures neutrals of the sample.

Improving the sensitivity, or the level of detection, benefits all types of systems. Very high end instruments often operate in special environments (e.g., vacuum) to enhance their performance. In such cases, special electronics and detector configurations can respond to femtoamp level ion currents (e.g., packets or steady fluxes of ions numbering in the thousands). In some cases, the charge from a single ion can initiate an 'avalance' in an electron multiplier providing indirect detection of atoamp currents. More often, non-idealities in the systems limit the realized level of detection to picoamp current levels. In one detector configuration, an amplifier measures the voltage resulting from the ion induced current through a precision, high value resistor, or build up on a capacitor. Noise inherent in the resistor or variability in the capacitor and system parasitics typically limit the detection level of such systems. Elimination or minimizing the impact of such components is desirable.

Many applications requiring high speed measurements also require more complex detection schemes. Given time, many sources of noise can be removed from the detected signal by techniques such as over sampling, digital signal processing, and averaging. However, the need to make fast measurements may limit or eliminate such approaches in an instrument. Many noise sources (e.g., resistor noise) are a function of system bandwidth; faster systems have higher inherent noise levels leading to inferior limits of detection.

Maximizing detector sensitivity and minimizing its noise provides many benefits to detection and analytical instrumentation. The obvious advantage is the ability to detect and or identify smaller quantities of target materials by a given system. This may make it feasible to use a system for new applications or to replace more expensive or complicated instruments. This may include performing tests traditionally conducted in a laboratory in the field. The need to collect samples by physical contact may be made possible without intimate contact. Non-contact measurements could be made at even greater distances from the source. The area monitored by one system could be enlarged. The range of materials that can be detected can be increased.

As an example, many explosives compounds have very low vapor pressures which makes detection of the volatile vapors emanating from them very difficult to detect unless the detector is in extremely tight proximity to the samples. In traditional explosives detectors, explosives particulates are collected and introduced into the detection instrument, where they are heated to increase the effective vapor pressure and concentration of organic volatiles to a range that can be detected by the detectors. By increasing the sensitivity of the detector in certain embodiments, the volatile explosives vapors can be detected directly, avoiding this added step of collecting the particles and heating them up (thermal desorption), simplifying the analysis process, and even eliminating the need for a contact detection method. In practice, in certain embodiments, this includes the elimination of the need to swab a surface to collect explosive compounds. Instead, a vacuum cleaner like fixture collects volatile compounds from the proximity of a surface and determines if there are explosive compounds on the surface. The surface may include, without limitation, a person, an object, a vehicle, and a structure.

In applications or operating conditions where the amount of target material present is above the level of detection of an instrument, the excess sensitivity available from the detector can be traded off for improved performance in another part of the system. Selectivity or the number of target compounds might be increased, this could be achieved by increasing the residence time of the ion in the DMS filter region. The increased residence time leads to narrower peaks, thus increasing the resolution of the DMS. In certain embodiments, power levels are reduced in the DMS. The gas flow in the DMS is also reduced below 200 ml/min. As the flow rate in current DMS systems is reduced, the sensitivity of the DMS is decreased. With the added sensitivity of an improved detector, such as the micro-faraday plate detector, this loss in sensitivity is acceptable, resulting in a DMS system that has a significantly reduced flow requirement for the transport gas (e.g., flows of less than 100 ml/min, less than 50 ml/min, less than 10 ml/min, less than 1 ml/min).

FIG. 30 is a conceptual diagram of an ion mobility based analyzer 1800 including a micro faraday element array 1802 according to an illustrative embodiment of the invention. The analyzer 1800 includes an inlet 1804, a flow path 1806, DMS filter 1808, deflector electrode 1810, and outlet 1812. Although not shown, the analyzer 1800 may include an ionization source to ionize the sample S. Alternatively, the sample S may have previously been ionized.

In operation, a sample S is introduced into the analyzer 1800 via inlet 1804 which travel through the DMS filter 1808 via the flow path 1806. The deflector electrode 1810 deflects ions that exit the DMS filter 1808 toward the micro faraday element array 1802. The micro faraday element array 1802 acts as a detector that provides enhanced sensitivity to compensate for possibly lower flow rates in the flow path 1806. The detected signal may then be provided to a controller, such as controller 30 of FIG. 1, to enable signal readout for further processing and control of the analyzer 1800. The neutrals are then exhausted from the analyzer 1800 via the outlet 1812.

FIG. 31 is a conceptual diagram of an ion mobility based analyzer 1850 including a micro faraday element array 1852 and plate detector electrodes 1864 and 1866 according to an illustrative embodiment of the invention. The analyzer 1850 includes an inlet 1854, a flow path 1856, DMS filter 1858, deflector electrode 1860, outlet 1862, and faraday plate detector electrodes 1864 and 1866. Although not shown, the analyzer 1850 may include an ionization source to ionize the sample S. Alternatively, the sample S may have previously been ionized.

In operation, a sample S is introduced into the analyzer 1850 via inlet 1854 which travel through the DMS filter 1858 via the flow path 1856. The deflector electrode 1860 deflects ions that exit the DMS filter 1858 toward the micro faraday element array 1852 and electrodes 1864 and 1866. The micro faraday element array 1852 acts as a detector that provides enhanced sensitivity to compensate for possibly lower flow rates in the flow path 1856. The electrodes 1864 and 1866 may also act as detectors and/or as directing/attracting electrodes for the micro faraday element array 1852. The detected signal may then be provided to a controller, such as controller 30 of FIG. 1, to enable signal readout for further processing and control of the analyzer 1850. The neutrals are then exhausted from the analyzer 1850 via the outlet 1862.

The reduced flow rate means that air filters and purifiers have much longer life times, pumps can be smaller and less power consuming and, therefore, the DMS system, such as analyzers 1800 and 1850, is significantly smaller. Data analysis algorithms may be simplified. Computation cycles may be lowered. Demand for sample collection and in-system flow control may be moderated. Also, the speed of detection is significantly increased. In one embodiment, operation in 'pulsed' or reduced duty cycle mode may be possible where the instrument is inactive or off some of the time. Multiple modes of operation may be possible including: 1) detect only, 2) detect and measure, 3) analyze, 4) evaluate, etc. with each mode requiring more or fewer active sub-systems and offering different information or varying response times.

The embodiments of FIGS. 31 and 32 use a micro faraday array and/or plate as on ion detector. In one embodiment, this detector is connected to an operational amplifier which detects and amplifies the ion induced current through a precision, high value resistor. The noise inherent in this resistor may be a major contributor to the noise level, and ultimately limit of detection, of the system. Thus, implementing an improved circuit or ion detector technology would directly enhance overall system performance. Moreover, a detector that improves upon one, some, or all of the following characteristics is desired: operation over a wide range of input currents, low noise, low power, high speed, signal response that is linear or can be described by a straightforward equation, operation at room temperature, operation over entire range of or subset(s) of −50 C to 300 C, amenable to integration with an ion mobility based filter and/or sensor and electronics fabrication, provides optional digital output, detector and associated electronics are a compact size.

A detector based on charge coupled device (CCD) technology is one circuit technology that would benefit DMS analyzer systems. U.S. Pat. No. 6,809,313 by Greshan, et. al., discloses a micro faraday element array for use in IMS. Here, CCD technology and integrated circuit fabrication combine a chip with an array of small faraday plates within a chip containing OP-AMPS, multiplexers, and passive components. By integrating the entire circuit (with the optional exception of the faraday plate), circuit parasitics are minimized but more importantly, the value of the capacitor used in the feedback of the detection circuit is extremely small and stable. Gresham, et. al. report a 1000× improvement in IMS sensitivity relative to the standard faraday detector provided with the spectrometer. In one embodiment, a similar increase in sensitivity is realized for a DMS analyzer system such as analyzers 1800 and 1850 by employing such a detector.

Use of CCD technology for ion detection is attractive. Used as a camera, CCD sensors create high-quality, low-noise images. In an optimal configuration, some CCD imagers can detect the charge from a few as tens of ions. This type of sensor does have limitations. Compared to CMOS integrated circuit technology, they can draw much more (100×) power. The technology is specialized for imaging applications and so does not enjoy the broad, commodity level availability of traditional integrated circuits. For performance limitations, CCDs when used for photon detection have less than 100% fill factor. As a simple example, each pixel in a CCD includes a semiconduction collection region and bounded by X conductor lines for signal read out. The conductors cover part of the area that could otherwise be used for photon collection; the larger the collection area (the fill factor), the greater the sensitivity of the pixel. While fill factors can be greater than 80%, special fabrication processes are required which increases cost and or reduces the complexity and capabilities of integrated electronic circuitry. When used in an ion detection application, the fill factor limitation is greatly reduced. Rather than using semiconductor material, an ion-CCD uses a metal plate. Since the underlying semiconductor substrate does not need to be exposed, the metal plate can cover the entire pixel area. Separation from neighboring pixels and any necessary guard traces would keep an array of sensors from achieving 100% fill factor but 90% or higher can be achieved readily. Furthermore, many instruments, such as IMS or DMS, presently incorporate only one or a few large detector 'pixels'. In this case, the pixel separation and guard traces are minimal and fill factors >99% are reasonable. The continuous nature of the DMS without the shutter/gate enables simplified integration of the proposed CCD based detector with the DMS according to an illustrative embodiment of the invention.

A competing and possibly complimentary technology to CCD imagers is active pixel sensors (APS). Typically implemented in CMOS, but possible in NMOS or PMOS, APS sensors add transistor(s) into each pixel cell. This greatly simplifies pixel readout and permits each cell to be addressed independent of the entire array. Standard silicon production lines can produce APS chips making them very inexpensive and readily available. CMOS circuits traditionally consume little power and so yields a low-power sensor. The noise levels in the CMOS sensors are typically higher than CCD although this gap is continually shrinking. Similarly, while the inclusion of transistors in each pixel reduces fill factor, the minimum feature size (e.g., small wire width) available in CMOS is falling much more quickly than CCD features and with the latest 90 nm circuit technology, this gap is almost negligible.

As an ion detection technology, APS has the potential to outperform CCD sensors in real world applications. Like the ion-CCD, the ion-APS can realize near 100% fill factor by covering the entire area with the Faraday plate. Unlike the ion-CCD approach, advanced analog and digital circuits can be integrated on the same chip as the ion-APS. In one embodiment, signal detection, preconditioning, and digital signal processing are all achieved before going off chip. This permits a digital or buffered analog output that can eliminate down stream noise sources experienced in traditional Faraday plate systems. Furthermore, the Faraday plate can be directly coupled to the base of a 'sense' transistor. This permits the charge from the ions to act as a variable voltage control to the source to drain. This produces a stable, relatively large current that is readily measured. More advanced circuit implementation permit the use of sub-threshold transistor operation which can provide circuit operation over a range that is many orders of magnitude larger than tradition circuit design techniques. Certain embodiments may employ semiconductor processing, integrated chips, digital logic, algorithms, aggregation circuits, and sensors as described in "Analog VLSI and Neural Systems" (1984) by Carver Mead.

Fabrication techniques can enable improved ion-CCD and ion-APS performance according to an illustrative embodiment of the invention. Introducing trench isolation, using SOI substrates, introducing cavities, forming membranes, etching RIE and DRIE structures, minimizing parasitics, and optimizing geometries enables improved ion mobility based sensors. Microfabrication of both detector and spectrometer together further improves the system. The Faraday plate may be any conductor or semiconductor material such as a metal, polysilicon, doped silicon, carbon nanotube or the like. In certain embodiments, nanotubes are employed as the detector "transistor". In one embodiment, highly figured (quasi-3D, 3D, heavily textured, spine covered) detector plates are produced that can benefit some applications and instruments. In other embodiments, the detector plate, detector electronics, spectrometer subcomponents and additional subcomponents are integrated in a single process on a single chip, use multiple processes to produce a single chip, or produce multiple chips. Subcomponents on separate chips may be packed in many ways including ball bonding, 3D chip stacks and tradition wire and solder bonding techniques. Circuits may introduce special drive functions and set subcomponents to floating, AC and or DC potentials to enable, enhance, or limit ion attraction, detection, and identification.

FIG. 32 is a conceptual diagram of an ion mobility based analyzer 1900 including both positive and negative ion detection using Faraday based element arrays 1902 and 1904 according to an illustrative embodiment of the invention. The analyzer 1900 includes sample S inlet 1906, DMS filter 1908, flow path 1910, faraday electrodes 1912, 1914, 1916, and 1918, and outlet 1920. Although not shown, the analyzer 1900 may include an ionization source to ionize the sample S. Alternatively, the sample S may have previously been ionized.

In operation, a sample S is introduced into the analyzer 1900 via inlet 1906 which travels through the DMS filter 1908 via the flow path 1910. The flow path 1910 includes two micro faraday element arrays 1902 and 1904 that act as positive and negative ion detectors respectively. Detector electrodes 1912, 1914, 1916, and 1918 may function as detector plates, but also a directing and/or attraction electrodes. For example, electrodes 1912 and 1914 may attract positive ions toward the array 1902 while deflecting negative ions toward the array 1904 and/or electrodes 1916 and 1918. The detected positive and/or negative signals may then be provided to a controller, such as controller 30 of FIG. 1, to enable signal readout for further processing and control of the analyzer 1900. The neutrals are then exhausted from the analyzer 1900 via the outlet 1920.

FIG. 33 is a conceptual diagram of an ion mobility based analyzer 1950 including both positive and negative ion detection using Faraday based element arrays 1952 and 1954 along with focusing gas inlets 1972 and 1974 according to an illustrative embodiment of the invention. The analyzer 1950 includes sample S inlet 1956, DMS filter 1958, flow path 1960, faraday electrodes 1962, 1964, 1966, and 1968, and outlet 1970. Although not shown, the analyzer 1950 may include an ionization source to ionize the sample S. Alternatively, the sample S may have previously been ionized.

In operation, a sample S is introduced into the analyzer 1950 via inlet 1956 which travels through the DMS filter 1958 via the flow path 1960. The focusing gas inlets 1972 and 1974 direct the ions exiting the DMS filter 1958 toward the center of the flow path 1960 into a concentration region for more efficient transfer to the detection region and enhanced detection. The flow path 1960 includes two micro faraday element arrays 1962 and 1964 that act as positive and negative ion detectors respectively. Detector electrodes 1962, 1964, 1966, and 1968 may function as detector plates, but also as directing and/or attraction electrodes. For example, electrodes 1962 and 1964 may attract positive ions toward the array 1952 while deflecting negative ions toward the array 1954 and/or electrodes 1966 and 1968. The detected positive and/or negative signals may then be provided to a controller, such as controller 30 of FIG. 1, to enable signal readout for further processing and control of the analyzer 1950. The neutrals are then exhausted from the analyzer 1950 via the outlet 1970.

Enhanced control of ion behavior in ion mobility based systems, devices and/or analyzers can be realized by enhanced control of the electric fields applied to the devices and enhanced methods of generating of the voltages to create these fields. In addition to controlling, or filtering, the ions within an ion mobility based device, minimizing the amount of power required for their generation and control can be critical for portable, hand held devices and/or systems.

Existing ion mobility based systems, such as DMS or FAIMS, employ relatively inefficient, large form-factor, and high power-consuming power supplies to generate, for example, the asymmetric radio frequency (Vrf) and compensation (Vc or Vcomp) voltages that filter ions of a sample. In one example, a differential ion mobility spectrometer (DMS) may utilize over 13 watts to generate around a 1500 volt peak of Vrf. Thus, there is a need for enhanced generation and control designs which result in reduced system power consumption.

In certain embodiments, the generation of the Vrf and Vc voltages of the filter of a DMS can be enhanced to reduce system power consumption by using one or more differentially-driven amplifier circuits and transformers which may include substrate-embedded transformers for ultra low power and high efficiency. Thus, where higher voltage magnitudes are required, a substrate-embedded, e.g., printed circuit board (PCB), transformer is employed that utilizes about 3 watts of power or less to generate a 1500 volt peak asymmetric waveform, e.g., Vrf. The advantages of certain embodiments of the invention include:

1. reduced interwinding capacitances
2. lower parasitic capacitances
3. higher dielectric capabilities to withstand breakdown
4. lower overall voltage levels in transformers to reduce possibility of voltage breakdown
5. more efficient step up to asymmetric voltage
6. for 2 transformer configuration (series), inductance increase linearly with turns as opposed to by the square of the turns in a single transformer. (results in higher turns ratio for given inductance).
7. By reducing inductance, enabling high frequency, enabling detection of lighter ions, enabling reducing the gap between the filter electrodes and miniaturizing the DMS further.
8. Series transformer configuration significantly reduces complexity of adding compensation voltage.
9. Employing differential voltage across filter electrodes enables less complex transformer and differential amplifier circuitry—reduces voltage by factor of 2 in comparison with prior art DMS voltage generators.
10. Differential drive circuit reduces spurious voltage effects on sensor/detector by reducing stray capacitances.
11. differential drive op amps (high slue rate, lower power, lower cost). Power approximately 2 mWatts as opposed to 400 mWatts in prior art amplifiers.
12. highly resistant core to reduce core losses (eddy currents).
13. small form factor IC-based drive circuit.

Accordingly, more efficient, more compact, and less power-consuming control designs and electronics can be implemented to enable the use of compact, portable DMS analyzers and other ion mobility based analyzers with longer portable use times, e.g., longer battery lifetimes. Examples of applications include toxic chemical monitoring in the field where detectors with long operating life times can be operated by people in the field to notify them of dangerous chemical exposures. If the instruments are sufficiently small, they can even be worn on the person, so as to enable the person full freedom of movement.

In certain embodiments, a PCB Transformer with the first side of the PCB including primary windings and the second side of PCB including secondary windings is employed for ion mobility based, and more particularly DMS, applications.

FIG. 34A is a top view of a PCB transformer 2000 including primary windings 2002 according to an illustrative embodiment of the invention. FIG. 34B is a perspective view of the PCB transformer 2000 according to an illustrative embodiment of the invention. The transformer 2000 including a first side 2006 with primary windings 2002 and a second side 2008 with secondary windings 2004. The primary 2002 and secondary windings 2004 are separated by a substrate 2010 while the transformer core is clamped around the PCB. FIG. 34B shows one embodiment where the primary windings 2002 are relatively close to the first side surface 2006 and the secondary windings are relatively close to the second side 2008 which reduces the potential adverse effects of parasitic or inter-winding capacitances between the windings.

Planar or PC Board transformer construction has been used for power applications for a number of years. This technique results in a transformer that is highly efficient, cost effective and has very tight coupling between windings resulting in low leakage inductance and therefore lower transient coupling to the output. Planar transformer designs for power applications utilize all of the layers of the PC board to maximize copper volume to reduce resistive and skin effect losses.

Under certain circumstances, the utilization of multiple layers and the large copper area may result in large parasitic or inter-winding capacitance. While this is acceptable in power applications, it results in very marginal performance for a radio frequency (RF) design. Planar PC board transformers though, if constructed properly, can be designed to accommodate the needs of high frequency, high voltage and low parasitic elements that are required for an RF application. In particular, the generation of a time varying, periodic, or asymmetric high voltage high frequency waveform (Vrf) for an ion mobility based analyzer such as a DMS is accommodated advantageously through the use of planar construction techniques.

The required characteristics of the transformer for this ion mobility based device application are high turns ratio, low inter-winding capacitance, high dielectric withstand and tight magnetic coupling between primary and secondary. The first of the requirements, high turns ratio, may be achieved through the use of fine trace geometries (at about or less than 6 millimeters). Because the load on the RF transformer 2000 is strictly capacitive, there is no need to deliver power to the load and, therefore, the trace resistance is non-critical. In one embodiment, low inter-winding capacitance is achieved by maximizing the separation of the windings within the FR4 PC stack of the substrate 2010 and by minimizing the copper area.

FR4 is a superior insulator and, therefore, supports the high dielectric withstand characteristic necessary to allow a large voltage differential between the primary 2002 and secondary 2004 windings. FR4 PCB materials are typically made of epoxy resin that saturates woven fiberglass and, therefore, are considered a general grade laminate. FR4 may be used for multilayer base materials and double sided materials. FR4 has superior electrical, thermal and physical characteristics compared to other laminates for many PCB applications. In one embodiment, tight magnetic coupling is intrinsic to the planar design due to the windings effectively occupying the same area in the X and Y axis.

Other embodiments of the invention include a PCB Transformer with first side of PCB including primary windings and second side of PCB including secondary windings for DMS applications where the primary and secondary are separated by an air gap.

FIGS. 35A-D provide various views of one embodiment of the PCB transformer 2000 including an exploded view in FIG. 35A, a closed side view in FIG. 35B, another side view FIG. 35C, and a top view in FIG. 35D. The core 2200 may include two halves that are combined to enclose at least a portion of the substrate 2010 as shown in FIG. 35B. In certain embodiments, the PCB transformer 2000 includes a first side having primary windings and a second side having secondary windings where the primary and secondary are separated by an air gap. Separators may be employed that are, for example, sandwiched between primary and secondary winding substrates.

Figure 36:
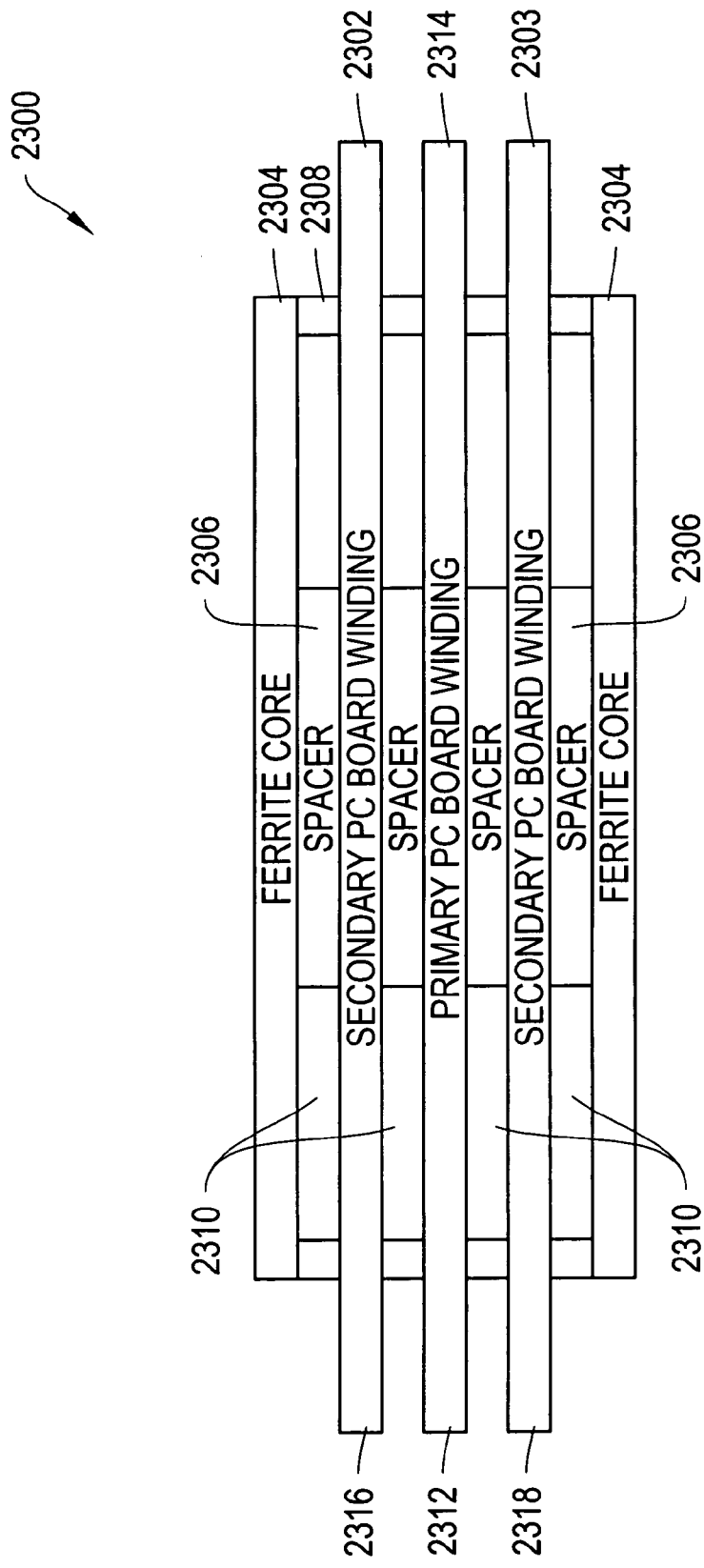
FIG. 36 shows one embodiment of a PCB transformer including multiple substrate layers and air gaps, according to an illustrative embodiment of the invention.

FIG. 36 shows one embodiment of a PCB transformer 2300 including multiple substrate layers (2312, 2316, 2318) and air gaps 2310. The air gaps 2310 are created by spacers 2306 and 2308 embedded between the substrates 2312, 2316, and 2318. The substrate 2312 includes primary windings 2314. The substrates 2316 and 2318 include the secondary windings 2302 and 2303 respectively.

In certain embodiments, the substrates 2312, 2316, and 2318 include FR4 PC board (PCB) material. One of the characteristics of FR4 PCB material that make it less than ideal for high frequency transformer construction is it's high dielectric constant. This dielectric constant (>4) results in high inter-winding capacitance which tends to reduce the self resonant frequency of the transformer. In a resonant design such as the RF driver for the time varying, periodic, or asymmetric waveform generator of an ion mobility based filter or DMS filter, high self resonant frequency is critical to the operation. One embodiment includes a technique to dramatically improve this parameter by constructing the transformer using multiple laminates separated by air gaps. Because the dielectric constant of air (1) is much lower than the PC material, the inter-winding capacitance is substantially reduced while still maintaining the necessary magnetic coupling between the windings.

Figure 37:
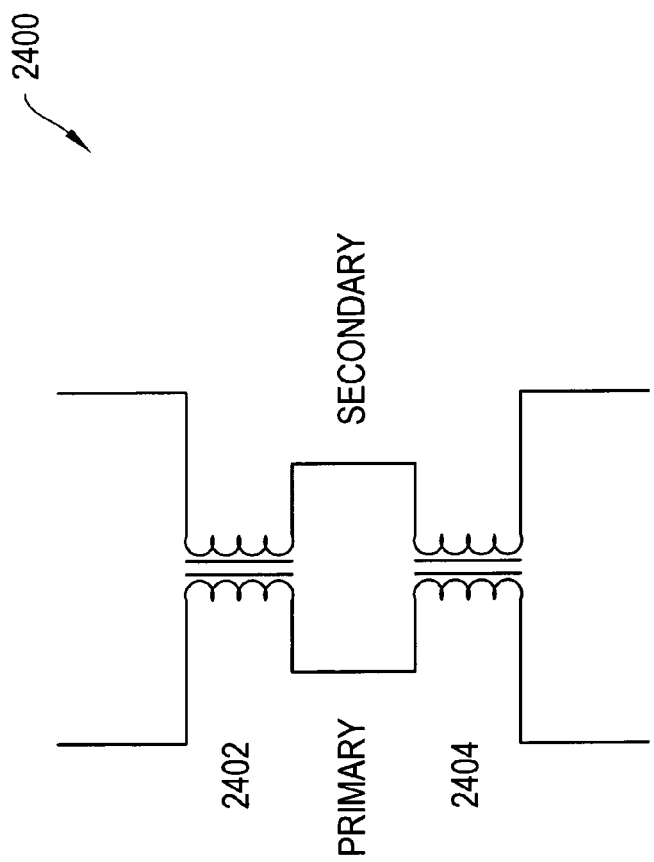
FIG. 37 is a schematic diagram of a circuit including two PCB transformers in series, according to an illustrative embodiment of the invention.

FIG. 37 is a schematic diagram of a circuit 2400 including two PCB transformers 2402 and 2404 in series to enable the advantages as described above.

In constructing a planar transformer for high voltage RF applications, two (2) parameters, e.g., turns ratio and self resonant frequency, are critical to the performance. Under certain conditions, these tend to be non-complimentary in that increasing turns ratio tends to decrease the self resonant frequency by increasing the parasitic winding capacitance and the magnetizing inductance of the transformer. In one embodiment, this effect is mitigated by distributing the windings over multiple cores, resulting in lower capacitance and inductance for a given turns ratio. This occurs because inductance goes up as the square of the turns on the same core but adds linearly between uncoupled cores. Another advantage of multiple cores is reduced core losses due to reduction of flux density. By distributing the high voltage waveform over multiple cores in certain embodiments, the flux density in any one core gets divided by the number of cores. Because the eddy current losses are a highly non-linear function of flux density, large gains in efficiency are achieved by reducing the flux density in each of the cores.

In certain embodiments, the same advantages with respect to the embodiment including two (2) transformers in series may be applied to multiple transformers in series. For example, four (4) transformers are advantageous for the same reason that two (2) transformers are advantageous. Additional transformers may be employed in series such as 6, 8, 10, and so on.

Figure 38:
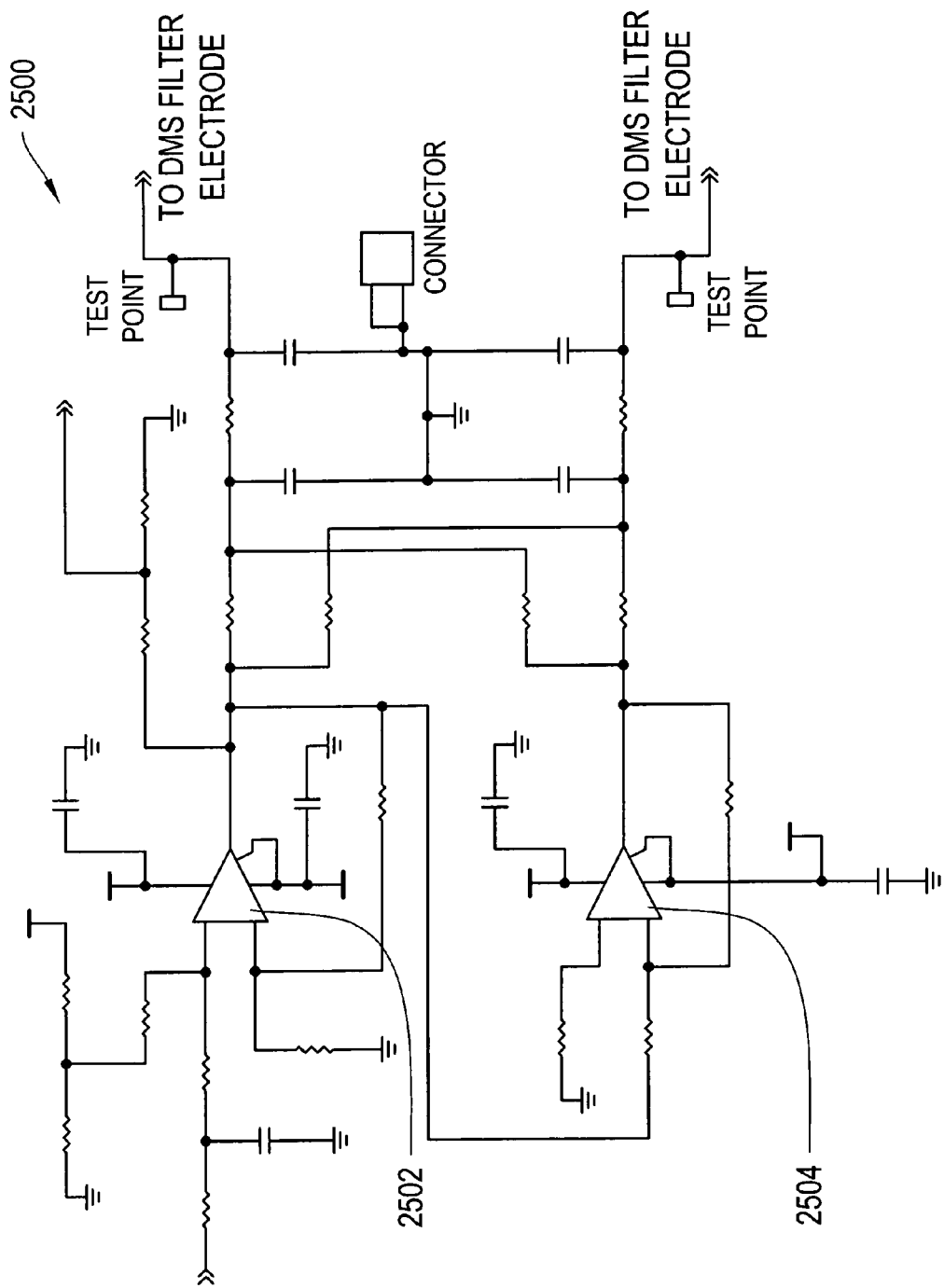
FIG. 38 provides an exemplary schematic diagram of a differential circuit 5200 that provides a differential Vc for a DMS device, according to an illustrative embodiment of the invention.

FIG. 38 provides an exemplary schematic diagram of a differential circuit 5200 that provides a differential Vc for a DMS device according to an illustrative embodiment of the invention. The output of amplifier 2502 is combined with the output of amplifier 2504 to provide a differential Vc to, for example, filter electrodes of a DMS filter.

The operation of a DMS sensor, e.g., DMS filter and detector, requires, in certain embodiments, the generation of two unique signals: 1) an asymmetric RF waveform voltage (Vrf) and 2) a compensation voltage (Vc). The Vc may be a signal of relatively low bandwidth with ranges in voltage between 15 and −50 volts. The large voltage swing make the generation of this signal difficult. Most operational amplifier (OP-AMPs) cannot accept the large supply rails necessary to cover this range of output voltage. The OP-AMPs that can support the relatively wide range require large supply currents, resulting in low efficiency. Another approach is to generate this signal with discrete transistors. However, this can be complicated and requires a large number of components.

According to one embodiment, it is recognized that if the Vc signal is generated differentially, the voltage requirements placed on the OP-AMPS is reduced by a factor of 2. Because the ion's are only affected by the electric field strength between the filter electrodes (where Vrf and Vc may be applied) and not the voltage relative to any reference, it does not matter if either of the filter plates is connected to reference ground. This makes a differential circuit possible and results in a simple, low power and inexpensive circuit with which to generate the compensation voltage.

Figure 39:
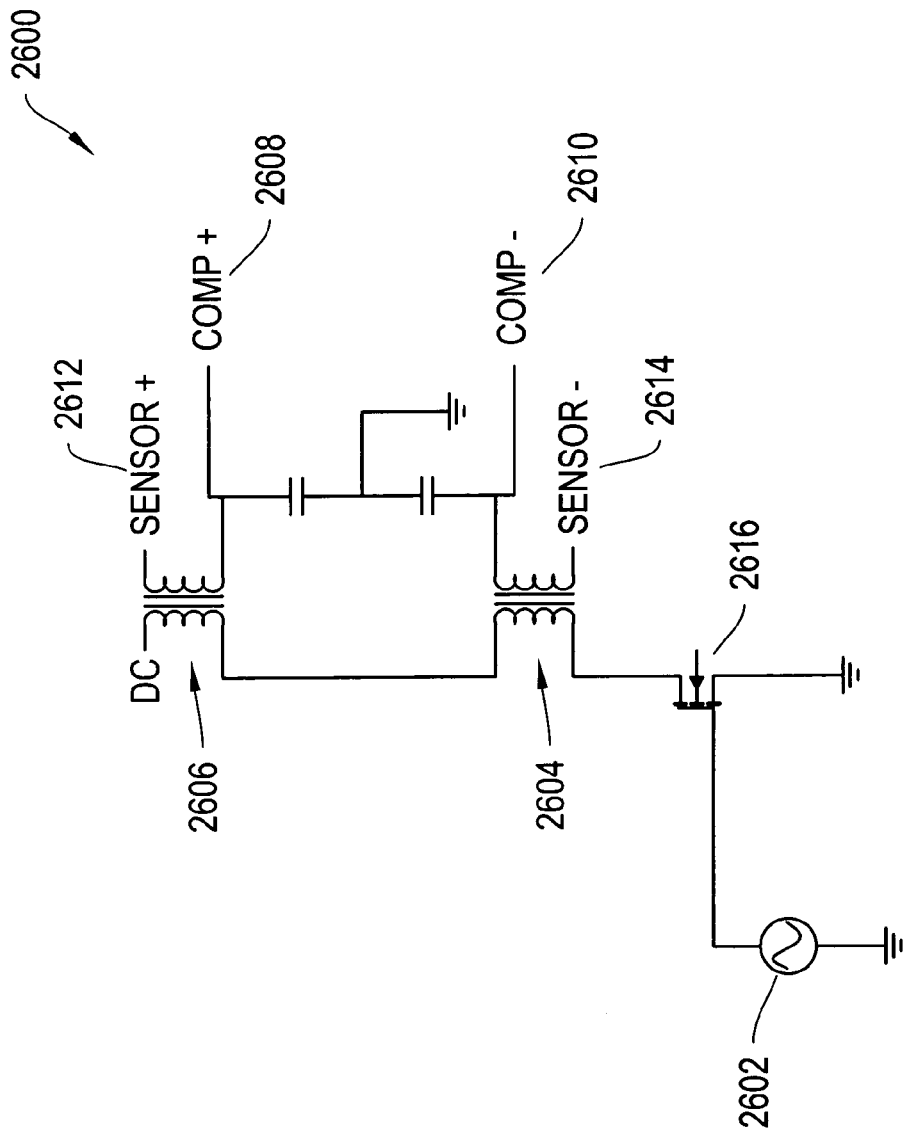
FIG. 39 shows an exemplary circuit that combines a differential Vrf with a differential Vc to be applied to the filter electrodes of a DMS device, according to an illustrative embodiment of the invention.

FIG. 39 shows an exemplary circuit 2600 that combines a differential Vrf with a differential Vc to be applied to the filter electrodes of a DMS device according to an illustrative embodiment of the invention. The asymmetric RF voltage source 2602 provides AC voltage to the primary windings of PCB transformers 2604 and 2606 via isolation amplifier 2616. The AC voltage is stepped up to the required high voltage asymmetric RF voltage (Vrf). The Vrf is combined with the differential Vc provided from, for example, the differential amplifier circuit 2500 via connections 2608 and 2610. The Vrf and Vc are combined at the secondary windings of PCB transformers 2606 and 2604 and output via connections 2612 and 2614 to, for example, the filter electrodes of a DMS filter.

The advantages to using multiple transformers for the generation of the DMS asymmetric waveform (Vrf) are discussed above to enable improved performance and efficiencies. Another advantage to multiple transformers beyond those mentioned above for generation of the signals necessary for the DMS sensor is the availability of a perfect summing node for the compensation voltage (Vc) and the time varying, periodic, or asymmetric RF signal (Vrf). In a single transformer solution, it is difficult to sum in the DC compensation voltage (Vc) as all nodes of the RF transformer secondary have a large AC excitation. Unintended coupling of this high frequency excitation into the compensation (Vc) circuit can result in unpredictable behavior and DC offsets in the output, resulting in reduced sensor and/or device accuracy.

In certain embodiments, this problem is solved through the use of a differential drive approach and multiple transformers to generate the Vc signal as shown in FIG. 39. By using any even number of transformers and 2 capacitors, which may be ceramic, it is possible to create an AC null point that is directly DC coupled to the controller and/or power supply output to the filter electrodes for the compensation signal (Vc). By creating an AC null at the center junction of the transformers, a balanced differential drive is established that creates a perfect summing point at the same time. The differential balance assures that no point on the circuit sustains more than ½ of the peak output voltage to the DMS filter. This simplifies the printed circuit design, connectors, and cabling to the sensor and/or filter because of the reduction in voltage withstand necessary.

In certain embodiments, the ion mobility based analyzer drive electronics reside on a printed circuit (PC) board of less than about: 15 in$^2$, 12 in$^2$, 8 in$^2$, 5 in$^2$, 2.5 in$^2$, 2 in$^2$, 1 in$^2$, and 0.5 in$^2$ in area. In certain embodiments, the ion mobility based analyzer drive electronics resides on a PC board including dimensions of less than about: 3 in×5 in, 2 in×4 in, 1 in×3 in, and 0.5×2 in. The ion mobility based analyzer drive electronics printed circuit board may contain integrated transformers of sizes of about and less than: 15 in$^2$, 12 in$^2$, 8 in$^2$, 5 in$^2$, 2.5 in$^2$, 2 in$^2$, 1 in$^2$, 0.5 in$^2$, 0.25 in$^2$, and 0.125 in$^2$ in area. The DMS drive electronics residing on a PC board may contain integrated transformers of dimensions of less than about: 3 in×5 in, 2 in×4 in, 1 in×3 in, and 0.5×2 in, 0.25 in×1 in, and 0.125×0.5 in, 0.25 in×0.25 in, and 0.125×0.125 in.

In certain embodiments, the ion mobility based drive electronics board, having an ion mobility based filter integrated into board, includes sizes of less than about: 15 in$^2$, 12 in$^2$, 8 in$^2$, 5 in$^2$, 2.5 in$^2$, 2 in$^2$, 1 in$^2$, and 0.5 in$^2$ in area. In another embodiment, the ion mobility based analyzer drive electronics residing on a PC board, having an ion mobility based filter integrated into board, includes dimensions of less than about: 3 in×in, 2 in×4 in, 1 in×3 in, and 0.5×2 in. In one embodiment, at least one electrode of a ion mobility based filter is formed on an ion mobility based drive electronics board. The PC board material may be: Peek, Teflon, Liquid Crystal Polymer (LCP), FR4, ceramic alumina, or silicon oxide or a dielectric deposited on the surface of silicon. In certain embodiments, the ion mobility based analyzer drive electronics printed circuit board, containing a ion filter region mounted on the pc board, includes a total PC board volume of less than 10 in$^3$, 8 in$^3$, 6 in$^3$, 4 in$^3$, 2 in$^3$, 1 in$^3$, 0.5 in$^3$. In one embodiment, an enhanced pre-amplifier (preamp) may be accomplished through careful PC board layout and through the use of a picket fence technique. The picket fence, may be accomplished by improving the electrical isolation of the pre-amplifier from the ion filter region. It may be accomplished by incorporating grounding electrodes into the PCB at various layer depth and locations. The electrodes form a "picket fence" around the detector electrodes so that stray noise from, for example, field lines from the ion filter electrodes are terminated on these picket fence electrodes rather than on the detector electrode. In certain embodiments, core configurations are enhanced using core material from standard off-the-shelf cores and materials. In another embodiment, an OP-AMP with capacitive feedback including low capacitance monolithic construction is employed in combination with the above circuits to enhance voltage generation designs In addition to the above described dimensions for ion mobility based analyzer systems, an ion mobility based analyzer including a compact DMS analyzer system may include, without limitation, filter capacitances of less than about 20 Pico Farads, less than about 15 Pico Farads, less than about 10 Pico Farads, less than about 5 Pico Farads, less than about 2 Pico Farads, less than about 1 pico Farad. In certain embodiments, the RF drive (field voltage—Vrf) and field compensation voltage (Vc) may introduce less than about 30 Pico Farads, less than about 20 Pico Farads, less than about 15 Pico Farads, less than about 10 Pico Farads, less than about 5 Pico Farads, less than about 2 Pico Farads, and less than about 1 Pico Farad of stray capacitance.

In certain embodiments, the surface area of the electrodes, including the filter electrodes that bound the DMS or ion mobility based analyzer flow channel, may have, without limitation, a surface area of less than about 250 mm$^2$, less than about 225 mm$^2$, less than about 200 mm$^2$, less than about 150 mm$^2$, less than about 125 mm$^2$, less than about 100 mm$^2$, less than about 75 mm$^2$, less than about 50 mm$^2$, less than about 25 mm$^2$, less than about 15 mm$^2$, less than about 10 mm$^2$, less than about 5 mm$^2$, less than about 2.5 mm$^2$, less than about 1 mm$^2$, and less than about 0.5 mm$^2$. In certain embodiments, the DMS or ion mobility based analyzer filter electrode surface area dimensions are, without limitation, less than about 15 mm×15 mm, less than about 15 mm×10 mm, less than about 15 mm×5 mm, less than about 15 mm×3 mm, less than about 15 mm×1 mm, less than about 10 mm×10 mm, less than about 10 mm×5 mm, less than about 10 mm×1 mm, less than about 5 mm×5 mm, less than about 5 mm×3 mm, less than about 5 mm×2 mm, less than about 5 mm×1 mm, less than about 1 mm×1 mm, less than about 1 mm×0.5 mm. In certain embodiments, the analytical gap distance are, without limitation, less than about 250 microns, less than about 200 microns, less than about 175 microns, less than about 150 microns, less than about 125 microns, less than about 100 microns, less than about 75 microns, less than about 50 microns, less than about 25 microns, and less than about 10 microns.

Such plate, surface, and/or electrode dimensions and capacitance ranges enable a compact ion mobility based analyzer and/or DMS analyzer system to operate with low power consumption in a hand held or portable. As evidenced by the foregoing discussion and illustrations, compact ion mobility based analyzers such as DMS analyzers of the invention are useful in a wide range of systems and applications.

In summary for certain embodiments, a longitudinal electric field is generated by the ion flow generator propels ionized sample received from an ionization region through a compensated, periodic electric field of the ion filter, with a desired species passing through the filter and flowing toward a detector region. Various options are possible. In one embodiment, a low volume gas flow carries the sample to the filter. In other embodiment, there is no need for gas flow and ion steering, or the longitudinal field itself, propels ions into the filter region, where the ions are further propelled by the ion flow generator.

In another embodiment, a supply of clean filtered air or some other gas is flowed in the negative longitudinal direction opposite the desired direction of ion flow to keep the ion filter and detector regions free of neutrals and to help remove solvent, reduce clustering, and minimize the effects of humidity.

A further embodiment of the present invention features an ion mobility spectrometer having a housing structure that defines a flow path (also known as a drift tube) that begins at a sample inlet for receipt of sample (i.e., sample molecules to be analyzed) and brings the sample to an ionization region. Once ionized, the sample passes to the ion filter, with desired ion species passing through the filter in the flow path, as propelled by the ion flow generator.

In one embodiment, the ion filter is provided with a plurality of high frequency, high voltage filter electrodes for creation of the asymmetric electric field transverse to the longitudinal ion flow direction along the flow path. In a preferred embodiment, this field is compensated, to pass only a desired ion species for downstream detection. In another embodiment, filtering is trajectory based without requiring compensation.

The ion flow generator creates a longitudinal electric field along the flow path (transverse to the asymmetric electric field) for propelling or transporting the ions through the asymmetric electric field toward the output region to enable detection and analysis. The ionization source may include a radiation source, an ultraviolet lamp, a corona discharge device, electrospray nozzle, plasma source, or the like.

In one embodiment, an electric controller supplies a compensation bias and an asymmetric periodic voltage to the ion filter. The ion filter typically includes a pair of spaced electrodes for creating the asymmetric electric field between the electrodes. The ion flow generator typically includes a plurality of spaced discrete electrodes proximate to the filter electrodes for creating a longitudinal direction electric field which propels the ions through the transverse asymmetric electric field, and onward for detection. The ion filter and flow generator may share none, some or all electrodes.

In another embodiment, the ion flow generator includes spaced resistive layers and a voltage is applied along each layer to create the longitudinally directed electric field which propels the ions through the filter's compensated asymmetric electric field and to the detector.

In another embodiment, the ion filter includes a first plurality of discrete electrodes electrically connected to an electric controller which applies the asymmetric periodic voltage to them. The ion flow generator includes a second plurality of discrete electrodes dispersed among the electrodes of the ion filter and connected to a voltage source which applies a potential gradient along the second plurality of discrete electrodes. Compensation voltage applied to the filter opens the filter to pass a desired ion species if present in the sample. If the compensation voltage is scanned, then a complete spectrum of the compounds in a sample can be gathered.

In one embodiment, the ion filter includes electrodes on an inside surface of the housing and the ion flow generator includes electrodes proximate to the ion filter electrodes. The housing may be formed using planar substrates. The ion detector also includes electrodes on an inside surface of the housing proximate to the ion filter and the ion flow generator.

In another embodiment, the ion filter may include electrodes on an outside surface of the housing and the ion flow generator then includes resistive layers on an inside surface of the housing. A voltage is applied along each resistive layer to create a longitudinal electric field. Alternatively, the ion filter and the ion flow generator are combined and include a series of discrete conductive elements each excited by a voltage source at a different phase.

In another embodiment, both the longitudinal and transverse fields and voltages are applied or generated via the same electrodes or via members of a set of electrodes. Because of the flexibility of the electronic drive system of the invention, all or part of the electrode set may be used for a given function or more than one function in series or simultaneously.

In yet a further embodiment of the invention, filtering is achieved without compensation of the filter field. In one practice, the spectrometer has a single RF (high frequency, high voltage) filter electrode on a first substrate, and a plurality of multi-function electrodes on a second substrate that are formed facing the filter electrode over the flow path. The plurality of electrodes forms a segmented detector electrode. Ions are filtered and detected by trajectory, being controlled by the asymmetric field and landing on an appropriate one of the detector electrode segments. Thus filtering is achieved without compensation of the filter field in a very compact package. The detector electrodes are monitored, wherein a particular species can be identified based on its trajectory for a given detection and given knowledge of the signals applied, the fields generated, and the transport (whether gas or electric field).

In practice of the invention, prior art pumps used to draw a sample, such as a gas containing compounds to be analyzed, into a ion mobility based analyzer, and to provide a flow of carrier gas, can be made smaller or even eliminated in practice of the invention. This is enabled in practice of the invention by incorporation of an ion flow generator which creates a longitudinal electric field in the direction of the intended ion travel path to propel the ions toward a detector region after passing through a transversely directed asymmetric electric field which acts as an ion filter.

The result is the ability to incorporate lower cost, lower flow rate, and smaller, even micromachined pumps and/or solid state flow generators, in embodiments of the invention; a decrease in power usage; the ability to apply clean filtered gas (e.g., dehumidified air) in a direction opposite the direction of ion travel to eliminate ion clustering and the sensitivity of the spectrometer to humidity. Separate flow paths for the source gas and the clean filtered gas may not be required, thus reducing the structure used to maintain separate flow paths taught by the prior art. Moreover, if an electrospray nozzle is used as the ionization source, the electrodes used to create the fine droplets of solvent can be eliminated because the electrodes which create the longitudinal and transverse electric fields can be used to function both to transport the ions and to create the fine spray of solvent droplets.

In a practice of the invention, an extremely small, accurate and fast ion mobility based analyzer filter and detection system can be achieved by defining an enclosed flow path between a sample inlet and an outlet using a pair of spaced substrates and disposing an ion filter within the flow path, the filter including a pair of spaced electrodes, one electrode associated with each substrate and a controller for selectively applying a bias voltage and an asymmetric periodic voltage across the electrodes to control the path of ions through the filter. In a further embodiment of the invention, it is possible to provide an array of filters to detect multiple selected ion species.

Alternative filter field compensation in practice of embodiments of the invention may be achieved by varying the duty cycle of the periodic voltage, with or without a bias voltage. Furthermore, in an embodiment of the invention, it is possible that by segmenting the detector, ion detection may be achieved with greater accuracy and resolution by detecting ions spatially according to the ions' trajectories as the ions exit the filter.

It will be further understood that while ion travel within the ion filter is determined by the compensated asymmetric filter field and the ion transport field, the invention may also include an ion concentrating feature for urging ions toward the center of the flow path. In one embodiment this concentrating is achieved where fields between electrodes on each substrate work together to urge the ions toward the center of the flow path as they pass there between approaching the ion filter.

In other embodiments, ion filtering is achieved without the need for compensation of the filter field. In one illustrative embodiment, a spectrometer of the invention has preferably a single RF (high frequency, high voltage) filter electrode. A segmented filter-detector electrode set faces the first electrode over the flow path, with the filter-detector electrode set having a plurality of electrodes in a row maintained at virtual ground. The asymmetric field signal is applied to the filter electrode and the asymmetric field is generated between the filter electrode and the filter-detector electrode set. Ions flow in the alternating asymmetric electric field and travel in oscillating paths that are vectored toward collision with a filter electrode, and in absence of compensation, favorably enables driving of the ions to various electrodes of the filter-detector electrode set. These collisions are monitored.

In a further embodiment, upstream biasing effects which ions flow to the filter. For example, a sample flows into an ionization region subject to ionization source, and electrodes are biased to deflect and affect flow of the resulting ions. Positive bias on a deflection electrode repels positive ions toward the filter and attracting electrodes being negatively biased attract the positive ions into the central flow of the ion filter, while negative ions are neutralized on the deflection electrode and which are then swept out of the device. Negative bias on the deflection electrode repels negative ions toward the filter and attracting electrodes positively biased attract the negative ions into the central flow path of the filter, while positive ions are neutralized on the deflection electrode.

In an embodiment, the path taken by a particular ion in the filter is mostly a function of ion size, cross-section and charge, which will determine which of the electrodes of the filter-detector electrode set that a particular ion species will drive into. This species identification also reflects the polarity of the ions and the high/low field mobility differences ("alpha") of those ions. Thus a particular ion species can be identified based on its trajectory (i.e., which electrode is hit) and knowledge of the signals applied, the fields generated, and the transport characteristics (such as whether gas or electric field).

In practice of the filter function of the invention, where the upstream biasing admits positive ions into the filter, those positive ions with an alpha less than zero will have a mobility decrease with an increase of a positively offset applied RF field. This will affect the trajectory of these ions toward the downstream detector electrodes. However, a positive ion with an alpha greater than zero will have a mobility increase with an increase of a negatively offset applied RF field, which in turn will shorten the ion trajectory toward the nearer detector electrodes.

Similarly, where the filter received negative ions, a negative ion with an alpha less than zero will have a mobility increase with an increase of a positively offset applied RF field; this will tend to affect the ion trajectory toward the downstream detector electrodes. However, a negative ion with an alpha greater than zero will have a mobility increase with an increase of a negatively offset applied RF field, which in turn will tend to shorten the ion trajectory toward the nearer detector electrodes. Thus, ions can be both filtered and detected in a spectrometer of the invention without the need for compensation.

In various embodiments of the invention, a spectrometer is provided where a plurality of electrodes are used to create a filter field and a propulsion field, in a cooperative manner that may be feature simultaneous, iterative or interactive use of electrodes. Where a plurality of electrodes face each other over a flow path, the filter field and the propulsion field may be generated using the same or different members of the electrode plurality. This may be achieved in a simple and compact package.

In practice of the invention, a spectrometer is provided in various geometries where a plurality of electrodes are used to create a filter and a propulsion field, in a cooperative manner that may be simultaneous or interactive. Where a plurality of electrodes face each other over a flow path, the filter field and the propulsion field may be generated using the same or different members of the electrode plurality to pass selected ion species through the filter.

It will be appreciated that in various of the above embodiments, a spectrometer can be provided in any arbitrarily shaped geometry (planar, coaxial, concentric, cylindrical) wherein one or more sets of electrodes are used to create a filtering electric field for ion discrimination. The same or a second set of electrodes, which may include an insulative or resistive layer, are used to create an electric field at some angle to the filtering electric field for the purpose of propelling ions through the filtering field to augment or replace the need for pump-driven propulsion such as with a carrier gas.

It will now be appreciated that a compact ion mobility based analyzer has been provided with e-field ion propulsion. Benefits of the invention include provision of a stable, easily controlled ion flow rate without the need for gas flow regulation. Elimination of the need for gas flow regulation reduces complexity and cost and improves reliability. Dramatic reduction of gas flow substantially reduces power consumption. Operation of the invention can reduce the amount of sample neutrals entering the analysis region between the filter electrodes. If only ions are injected into the filter, then it is easier to keep the ion filter in a controlled operating state, such as control of moisture level. The result is very reproducible spectra in a low power analytical system.

In one embodiment, the present invention provides an ion filter and detection system which does not require the high flow rate, high power consumption pumps normally associated with ion mobility based analyzers.

In another embodiment, the present invention provides a method and apparatus for highly efficient conveyance of ions into and through a high field ion mobility filter.

In a further embodiment, the present invention provides a method and apparatus for efficient conveyance of ions into and through a high field ion mobility filter without the use of a carrier gas.

In another embodiment, the present invention provides a ion mobility based analyzer filter and detection system which can quickly and accurately control the flow of selected ions to produce a sample spectrum.

The present invention may provide a ion mobility based analyzer filter and detection system which has a sensitivity of parts per billion to parts per trillion. The present invention may provide a ion mobility based analyzer filter and detection system which may be packaged in a single chip or chip assembly. The present invention may also provide a ion mobility based analyzer filter and detection system which is cost effective to implement, produce and operate.

The examples disclosed herein are shown by way of illustration and not by way of limitation. Although specific features of the invention are shown in some drawings and not in others, this is for convenience only as various features may be combined with any or all of the other features in accordance with the invention.

What is claimed is:

1. A system for analyzing a sample comprising:
a multilayered chip assembly including:
a gas chromatograph layer including a micromachined GC column,
a first ion mobility filter layer including a plurality of ion filter flow channels, each ion filter flow channel including a time-varying electric field applied to the moving ions for discriminating between ions of the sample, and
a detector layer including a detector for detecting at least a portion of the ions exiting the ion mobility filter layer, wherein the detector layer includes a plurality of flow channels, each flow channel including at least one detector element for detecting a portion of ions exiting the ion mobility filter layer.

2. The system of claim 1, wherein the gas chromatograph layer includes a micromachined GC column outlet on a surface in fluid communication with another layer of the multilayered chip assembly.

3. The system of claim 1, wherein the time-varying electric field includes an asymmetric electric field.

4. The system of claim 3, wherein the asymmetric electric field includes a superimposed compensation field.

5. The system of claim 1, wherein the time-varying electric field includes a substantially symmetric electric field.

6. The system of claim 1, comprising a MEMS-based pump flow generator for flowing a carrier gas through the ion mobility based filter layer, the flow generator being outside of the ion mobility based filter layer.

7. A system for analyzing a sample comprising:
a multilayered chip assembly including:
a gas chromatograph layer including a micromachined GC column,
a first ion mobility filter layer including a plurality of ion filter flow channels, each ion filter flow channel including a time-varying electric field applied to the moving ions for discriminating between ions of the sample, and a detector layer including a detector for detecting at least a portion of the ions exiting the ion mobility filter layer, wherein the detector layer includes a plurality of flow channels, each flow channel including first and second detector elements for detecting a portion of ions exiting the ion mobility filter layer.

8. The system of claim 7, wherein the first detector element is biased to detect positive ions and the second detector element is biased to detect negative ions.

9. The system of claim 1, wherein the first ion mobility based filter layer includes:

a first pair of opposing electrodes for generating the time varying electric field therebetween, a second pair of opposing electrodes, the second pair of electrodes being biased in relation to the first pair of electrodes to generate an ion flow along a flow path including the first and second pair of electrodes.

10. The system of claim 1, comprising a second ion mobility based filter layer in communication with at least one of the first ion mobility based filter layer and the detector layer.

11. The system of claim 10, wherein the second ion mobility based filter includes at least one of an IMS, DMS, hybrid IMS/DMS analyzer.

12. The system of claim 7, comprising a second ion mobility based filter layer in communication with at least one of the first ion mobility based filter layer and the detector layer.

13. The system of claim 12, wherein the second ion mobility based filter includes at least one of an IMS, DMS, hybrid IMS/DMS analyzer.

14. A method for analyzing a sample using a multilayered chip assembly comprising:

eluting a sample from a gas chromatograph layer including a micromachined GC column, filtering a portion of the sample from a first ion mobility filter layer including a plurality of ion filter flow channels by applying a time-varying electric field to the ions of the sample to discriminate between ions of the sample in each of the ion filter flow channels, and detecting the portion of sample within a detector layer, wherein the detector layer includes a plurality of flow channels, each flow channel including at least one detector element for detecting a portion of ions exiting the ion mobility filter layer.

15. The method of claim 14, comprising eluting the sample from a micromachined GC column outlet on a surface of the gas chromatograph layer in fluid communication with another layer of the multilayered chip assembly.

16. The method of claim 14, wherein the time-varying electric field includes an asymmetric electric field.

17. The method of claim 16, wherein the asymmetric electric field includes a superimposed compensation field.

18. The method of claim 14, wherein the time-varying electric field includes a substantially symmetric electric field.

19. The method of claim 14, comprising flowing a carrier gas through the ion mobility based filter layer using a MEMS-based pump flow generator that is outside of the ion mobility based filter layer.

20. The method of claim 14, wherein the first ion mobility based filter layer includes:

a first pair of opposing electrodes for generating the time varying electric field therebetween, a second pair of opposing electrodes, the second pair of electrodes being biased in relation to the first pair of electrodes to generate an ion flow along a flow path including the first and second pair of electrodes.

21. The method of claim 14, comprising using a second ion mobility based filter layer in communication with at least one of the first ion mobility based filter layer and the detector layer.

22. The method of claim 21, wherein the second ion mobility based filter includes at least one of an IMS, DMS, hybrid IMS/DMS analyzer.

23. A method for analyzing a sample using a multilayered chip assembly comprising:

eluting a sample from a gas chromatograph layer including a micromachined GC column, filtering a portion of the sample from a first ion mobility filter layer including a plurality of ion filter flow channels by applying a time-varying electric field to the ions of the sample to discriminate between ions of the sample in each of the ion filter flow channels, and detecting the portion of sample within a detector layer, wherein the detector layer includes a plurality of flow channels, each flow channel including first and second detector elements for detecting a portion of ions exiting the ion mobility filter layer.

24. The method of claim 23, wherein the first detector element is biased to detect positive ions and the second detector element is biased to detect negative ions.

25. The method of claim 23, comprising using a second ion mobility based filter layer in communication with at least one of the first ion mobility based filter layer and the detector layer.

26. The method of claim 25, wherein the second ion mobility based filter includes at least one of an IMS, DMS, hybrid IMS/DMS analyzer.

* * * * *